United States Patent [19]

Snow

[11] Patent Number: 5,958,883
[45] Date of Patent: Sep. 28, 1999

[54] ANIMAL MODELS OF HUMAN AMYLOIDOSES

[75] Inventor: Alan D. Snow, Seattle, Wash.

[73] Assignee: Board of Regents of the University of Washington Office of Technology, Seattle, Wash.

[21] Appl. No.: 08/461,216

[22] Filed: Jun. 5, 1995

Related U.S. Application Data

[63] Continuation of application No. 07/969,734, Oct. 23, 1992, abandoned, which is a continuation-in-part of application No. 07/950,417, Sep. 23, 1992, abandoned.

[51] Int. Cl.[6] .............................. A61K 38/08; C07K 7/06
[52] U.S. Cl. .............................. 514/16; 514/17; 530/328; 530/329
[58] Field of Search ........................ 514/16, 17; 530/300, 530/328, 329

[56] References Cited

U.S. PATENT DOCUMENTS

| | | | |
|---|---|---|---|
| 3,000,787 | 9/1961 | Bianchini et al. | 424/551 |
| 4,956,347 | 9/1990 | Ban et al. | 514/54 |
| 5,092,876 | 3/1992 | Dhawan et al. | 530/327 |
| 5,137,873 | 8/1992 | Yankner | 514/15 |
| 5,164,295 | 11/1992 | Kisilevsky et al. | 435/7.8 |
| 5,221,607 | 6/1993 | Cordell et al. | 530/300 |

FOREIGN PATENT DOCUMENTS 450 508 A2  9/1991  European Pat. Off. .

OTHER PUBLICATIONS

Bitter, T. and H. Muir. 1966. Mucopolysaccharides of whole human spleens in generalized amyloidosis. *J. Clin Invest* 45:963–975.

Dalferes, E.R., B. Radhakrishnamurthy and G.S. Berenson. 1968. Glycosaminoglycans in experimental amyloidosis. *Proc Soc Exp Biol Med* 127:925–929.

Okuyara, T. and K. Turumi. Acid mucopolysaccharides from a spleen of primary amyloidosis. *Clin Chim Acta* 8:140–142, 1963.

Pennock, C.A. Association of acid mucopolysaccharides with isolated amyloid fibrils. *Nature* 217:753–754, 1968.

Snow, A.D. and R. Kisilevsky. 1985. Temporal relationship between glycosaminoglycan accumulation and amyloid deposition during experimental amyloidosis. A histochemical study. *Lab. Invest.* 53:37–44.

Snow, A.D., R. Kisilevsky, C. Stephens, and T. Anastassiades. 1987. Characterization of tissue and plasma glycosaminoglycans during experimental AA amyloidosis and acute inflammation. Qualitative and quantitative analysis. *Lab. Invest.* 56:665–675.

Snow, A.D., H. Mar, D. Nochlin, K. Kimata, M. Kato, S. Suzuki, J. Hassell, and T.N. Wight. 1988a. The presence of heparan sulfate proteoglycans in the neuritic plaques and congophilic angiopathy in Alzheimer's disease. *Am. J. Path.* 133:456–463.

Snow, A.D., R. Kisilevsky, and T.N. Wight. 1988b. Immunolocalization of heparan sulfate proteoglycans to AA amyloid deposition sites in spleen and liver during experimental amyloidosis. In *Amyloid and Amyloidosis*. T. Isobe, S. Araki, F. Uchino, S. Kito and E. Tsubura, editors. Plenum Publishing Corp., New York, 87–93.

(List continued on next page.)

*Primary Examiner*—Jeffrey E. Russel
*Attorney, Agent, or Firm*—Steve T. Zelson; Elias J. Lambiris; Carol E. Rozek

[57] ABSTRACT

In vivo assays for selecting candidate therapeutics for inhibiting amyloidoses, such as congophilic and fibrillar β/A4 amyloid deposition in brain. A candidate reagent is administered to a first rat in a first infusate comprising β/A4 peptide and perlecan by continuous infusion into the hippocampus for at least one week. The candidate reagent is selected as a candidate therapeutic for inhibiting congophilic and fibrillar β/A4 amyloid deposition in brain if the first infusate diminishes congo red and thioflavin S staining indicative of amyloid deposition adjacent to the infusion site, as compared with a second rat receiving a second infusate consisting essentially of β/A4 peptide and perlecan.

14 Claims, 45 Drawing Sheets

OTHER PUBLICATIONS

Snow, A.D., M.G. Kinsella, R.T. Sekiguchi, D. Nochlin, and T.N. Wight. Binding by a high molecular weight heparan sulfate proteoglycan to the extracellular domain of the beta–amyloid protein of Alzheimer's disease. *Soc. Neurosc. 21st Ann. Meet.*, New Orleans, Nov. (1991) abstract 439.12.

Snow, A.D., H. Mar, D. Nochlin, R.T. Sekiguchi, K. Kimata, Y. Koike, and T.N. Wight. 1990a. Early accumulation of heparan sulfate in neurons and in the beta–amyloid protein containing lesions of Alzheimer's disease and Down's syndrome. *Am. J. Path.* 137:1253–1270.

Snow, A.D., M.G. Kinsella, P.B. Prather, D. Nochlin, M.B. Podlisny, D.J. Selkoe, R. Kisilevsky, and T.N. Wight. 1989. A characteristic binding affinity between heparan sulfate proteoglycans and the A4 amyloid protein of Alzheimer's disease. *J. Neuropath. Exp. Neurol.* 48:352, (abstract).

Abraham, C.R., D.J. Selkoe and H. Potter. 1988. Immunochemical identification of the serine protease inhibitor alpha1–antichymotrypsin in the brain amyloid deposits of Alzheimer's disease. *Cell* 52:487–501.

Esch, F.S., P.S. Keim, E.C. Beattie, R.W. Blancher, A.R. Culwell, T. Oltersdorf, D. McClure, and P.J. Ward. 1990. Cleavage of amyloid beta peptide during constitutive processing of its precursor. *Science* 248:1122–1124.

Noonan, D.M., A. Fulle, P. Valente, S. Cai, E. Horigan, M. Sasaki, Y. Yamada, and J.R. Hassell. 1991. The complete sequence of perlecan, a basement membrane heparan sulfate proteoglycan, reveals extensive similarity with laminin A chain, low density lipoprotein–receptor, and the neural cell adhesion molecule. *J. Biol. Chem.* 266:22939–22947.

Kallunki, P., and K. Tryggvason. 1992. Human basement membrane heparan sulfate proteoglycan core protein: A 467–kD protein containing multiple domains resembling elements of the low density lipoprotein receptor, laminin, neural cell adhesion molecules, and epidermal growth factor. *J. Cell Biol.* 116:559–571.

Murdoch, A.D., G.R. Dodge, I. Cohen, R.S. Tuan, and R.V. Iozzo. 1992. Primary structure of the human heparan sulfate proteoglycan from basement membrane (HSPG2/perlecan): A chimeric molecule with multiple domains homologous to the low density lipoprotein receptor, laminin, neural cell adhesion molecules and epidermal growth factor. *J. Biol. Chem.,* in press.

Coria, R., Castano, E., Prelli, R., Larrondo–Lillo, M., Van Duinen, S., Shelanski, M.L., Grangione, B. 1988. Isolation and characterization of amyloid P component from Alzheimer's disease and other types of cerebral amyloidosis. *Lab. Invest.* 58: 454–458.

Snow, A.D. and Wight, T.N. Review: Proteoglycans in the pathogenesis of Alzheimer's disease and other amyloidoses. *Neurobiol. Aging* 10: 481–497, 1989.

Katz, E.P., Watchel, E.J., Maroudas, A. 1986. Extrafibrillar proteoglycans osmotically regulate the molecular packing of collagen in cartilage. *Biochim. Biophys. Acta* 882: 136–139.

Mathews, M. B. and Decker, L. The effect of acid mucopolysaccharides and acid mucopolysaccharide–proteins on fibril formation from collagen solutions. *Biochem. J.* 109: 517–524, 1968.

Obrink, B. The influence of glycosaminoglycans on the formation of fibers from monomeric tropocollagen in vitro. *Eur. J. Biochem.* 31: 129–137, 1973.

Vogel, K.G., M. Paulsson, and D. Heinegard. 1984. Specific inhibition of type I and type II collagen fibrillogenesis by the small proteoglycan of tendon. *Biochem. J.* 223:587–597.

McCubbin, W.D., Kay, C.M., Narindrasorasak, S., Kisilevsky, R. Circular dichroism and fluorescence studies on two murine serum amyloid A proteins. *Biochem. J.* 256: 775–783, 1988.

Snow, A.D., S. Lara, D. Nochlin, and T.N. Wight. 1989. Cationic dyes reveal proteoglycans structurally integrated within the characteristic lesions of Alzheimer's disease. *Acta Neuropath.* 78:113–123.

Young, I.D., Willmer, J.P., Kisilevsky, R. 1989. The ultrastructural localization of sulfated proteoglycans is identical in the amyloids of Alzheimer's disease and AA, AL, senile cardiac and medullary carcinoma associated amyloidosis. *Acta Neuropathol.* (Berl.) 78: 202–209.

Hyman, B.T., G.W. Van Hoesen, A.R. Damasio, and C.L. Barnes. 1984. Alzheimer's disease: cell specific pathology isolates the hippocampal formation. *Science* 225: 1168–1170.

Geddes, J.W., K.J. Anderson, and C.W. Cotman. 1986. Senile plaques as aberrant sprouting–stimulating structures. *Exp. Neurol.* 94: 767–776.

Ishihara, T., T. Gondo, M. Takahashi, F. Uchino, S. Ikeda, D. Allsop, and K. Imai. 1991. Immunohistochemical and immunoelectron microscopic characterization of cerebrovascular and senile plaque amyloid in aged dogs' brains. *Br. Res.* 548: 196–205.

Selkoe, D.J., D.S. Bell, M.B. Podlisny, D.L. Price, and L.C. Cork. 1987. Conservation of brain amyloid proteins in aged mammals and humans with Alzheimer's disease. *Science* 235: 873–877.

Martin, L.J., S.S. Sisodia, E.H. Koo, L.C. Cork, T.L. Dellovade, A. Weidemann, K. Beyreuther, C. Masters, and D.L. Price. 1991. Amyloid precursor protein in aged nonhuman primates. *Proc. Natl. Acad. Sci.* 88: 1461–1465.

Cork, L.C., R.E. Powers, D.J. Selkoe, P. Davies, J.J. Geyer, and D.L. Price. 1988. Neurofibrillary tangles and senile plaques in aged bears. *J. Neuropath. Exp. Neurol.* 47: 629–641.

Vaughan, D.W. and A. Peters 1981. The structure of neuritic plaques in the cerebral cortex of aged rats. *J. Neuropath. Exp. Neurol.* 40: 472–487.

Wirak, D.O., R. Bayney, T.V. Ramabhadran, R.P. Fracasso, J.T. Hart, P.E. Hauer, P. Hsiau, S.K. Pekar, G.A. Scangos, B.D. Trapp. 1991. Deposits of amyloid beta protein in the central nervous system of transgenic mice. *Science* 253: 323–325.

Quon, D., Y. Wang, R. Catalano, J.M. Scardina, K. Murakami, and B. Cordell. 1991. Formation of beta–amyloid protein deposits in brains of transgenic mice. *Nature* 352: 239–241.

Kawabata, S., G.A. Higgins, and J.W. Gordon. 1991. Amyloid plaques, neurofibrillary tangles and neuronal loss in brains of transgenic mice overexpressing a C–terminal fragment of human amyloid precursor protein. *Nature* 354: 476–478.

Jucker, M., L.C. Walker, L.J. Martin, C.A. Kitt, H.K. Kleinman, D.K. Ingram, and D.L. Price. 1992. Age–associated inclusions in normal and transgenic mouse brain. *Science* 255: 1443–1445.

Richards, S.J., J.J. Waters, K. Beyreuther, C.L. Masters, C.M. Wischik, D.R. Sparkma, C.L. White, C.R. Abraham, and S.B. Dunnett. 1991. Transplants of mouse trisomy 16 hippocampus provide a model of Alzheimer's disease neuropathology. *EMBO J.* 10: 297–303.

Alvarado, M.V., Castejon, H.V. 1984. Histochemical demonstration of cytoplasmic glycosaminoglycans in the macroneurons of the human central nervous system. *J. Neurosci. Res.* 11: 13–26.

Anderson, M.J., Fambrough, D.M. 1983. Aggregates of acetylcholine receptors are associated with plaques of a basal lamina heparan sulfate proteoglycan on the surface of skeletal muscle fibers. *J. Cell Biol.* 97: 1396–1411.

Clausen, J., Christensen, H.E. 1964. Paraproteins and acid mucopolysaccharides in primary amyloidosis. *Acta Pathol. Microbio. Scand.* 60: 493–510.

Narindrasorasak, S., D. Lowery, P. Gonzalez–DeWhitt, R.A. Poorman, B. Greenberg, and R. Kisilevsky, 1991. High affinity interactions between the Alzheimer's beta–amyloid precursor proteins and the basement membrane form of heparan sulfate proteoglycan. *J. Biol. Chem.* 266:12878–12883.

Snow, A.D., H. Mar, D. Nochlin, H. Kresse, and T.N. Wight. 1992. Peripheral distribution of dermatan sulfate proteoglycans (decorin) in amyloid–containing plaques and their presence in neurofibrillary tangles of Alzheimer's disease. *J. Histochem. Cytochem.* 40:105–113.

Snow, A.D. 1990c. The possible involvement of specific proteoglycans in the pathogenesis of Alzheimer's disease, Down's syndrome and other amyloidoses. In *Aging of the Brain: Cellular and Molecular Aspects of Brain Aging and Alzheimer's Disease.* T. Nagatsu, O. Hayaishi, editors. Japan Scientific Societies Press, Tokyo, 185–204.

Axelrad, M.A., R. Kisilevsky, J. Willmer, S.J. Chen, and M. Skinner. 1982. Further characterization of amyloid–enhancing factor. *Lab. Invest.* 47:139–146.

Cardin, A.D., and H.J.R. Weintraub. 1989. Molecular modeling of protein–glycosaminoglycan interactions. *Arteriosc.* 9:21–32.

Schubert, D., R. Schroeder, M. Lacorbiere, T. Saitoh, and G. Cole. 1988. Amyloid beta protein precursor is possibly a heparan sulfate proteoglycan core protein. *Science* 241:223–226.

Dwulet, F.E. and M.D. Benson. 1987. Primary structure of amyloid fibril protein AA in azocasein–induced amyloidosis of CBA/J mice. *J. Lab. Clin. Med.* 110:322–329.

Westermark, P., K.H. Johnson, G.T. Westermark, K. Sletten and D.W. Hayden. 1986. Bovine amyloid protein AA: isolation and amino acid sequence analysis. *Comp. Biochem. Physiol.* 85:609–614.

1984. Amyloid A proteins in different species. *Appl. Path.* 2:316–327, Hol, et al.

Snow, A.D., R. Kisilevsky and T.N. Wight. Immunolocalization of heparan sulfate proteoglycans to AA amyloid deposition sites in spleen and liver during experimental amyloidosis. In: *Amyloid and Amyloidosis*, edited by I Isobe, New York, Plenum Press, New York, pp. 87–93. 1988.

Snow, A.D., M. Raskind, and T.N. Wight. The potential significance for the presence of glycosaminoglycans in the cerebrospinal fluid of normal and aged Alzheimer's patients. *Alz. Dis. Assoc. Dis.* 2(3): p. 182, 1988 (abstract).

Snow, A.D., J. Willmer and R. Kisilevsky. A close ultrastructural relationship between sulfated proteoglycans and AA amyloid fibrils. *Lab Invest* 57:687–698, 1987.

Pennock, C.A. J. Burns and G. Massarella. 1968. Histochemical investigation of acid mucosubstances in secondary amyloidosis. *J Clin Path* 21:578–581.

Snow, A.D., R. Bramson, H. Mar, T.N. Wight, and R. Kisilevsky, 1991. A temporal and ultrastructural relationship between heparan sulfate proteoglycans and AA amyloid in experimental amyloidosis. *J. Histochem. Cytochem.* 39: 1321–1330, 1991.

Kisilevsky, R. From arthritis to Alzheimer's disease: current concepts on the pathogenesis of amyloidosis. *Can. J. Physiol. Pharmacol.* 65: 1805–1815, 1987.

Marx, J. Major setback for Alzheimer's models. *Science* 255: 1200–1202, 1992.

Conti, L., Lazzerini, F., Re, F., and Santini, V. Sulfomucopolysaccharides in the treatment of primary degenerative and multi–infarct dementias: preliminary results of a placebo–controlled clinical trial. In: *Senile dementias. II.International Symposium.*, Eds. A. Agnoli, J. Cohn, N. Lassen, and R. Mayeux, John Libbey Eurotext, Paris, 1988, pp. 445–448.

Ban, T.A., Modafferi, A, Morey, L., Placidi, G.F., Postiglione, A., Re, F., and Santini, V. Global changes with glycosaminoglycan polysulfate in primary degenerative and multi–infarct dementia. *Current Therap. Res.* 41: 631–636, 1977.

Ban, T.A., Morey L.C., Aguglia, E., Batista, R. Campanella, G., Conti, L., Dreyfus, J–F., Fjetland, O.K., Grossi, D., Modaferri, A., Marin–Perez, G.A., Postiglione, A., Santini, V., Torres–Ruiz, A., and Vergara, L.E. Glycosaminoglycan polysulfate in the treatment of old age dementias. *Prog. Neuro. Psychopharmacol. & Biol. Psychiat.* 15: 323–342, 1991.

Ban, T.A., Morey, L.C., Fjetland, O.K., Rengo, F., Ferrara, N., Agnetti, V., D'Onofrio, M., Facchini, G., Anzivino, F., Perego, M.A., Danese, C., Capurso, A., Tommasi, A., Scardigli, G., Jans, G., Parnetti, L., Senin, U., and Bergamasco, B. Early manifestations of dementing illness: Treatment with glycosaminoglycan polysulfate. *Prog. Neuro. Psychopharmacol. & Biol. Psychiat.* 16: 661–676, 1992.

Kisilevsky, R. and A. Snow. The potential significance of sulphated glycosaminoglycans as a common constituent of all amyloids: or, perhaps amyloid is not a misnomer. *Medical Hypotheses* 26: 231–236, 1988.

Snow, A.D., J. Willmer, and R. Kisilevsky. Sulfated glycosaminoglycans: A common constituent of all amyloids? *Lab. Invest.* 56: 120–123, 1987.

Snow, A.D. and R. Kisilevsky. The time relationship between amyloid deposition and glycosaminoglycan accumulation during experimental amyloidosis. In: *Amyloidosis*, Eds. G.G. Glenner, E.F. Osserman, E.P. Benditt, E. Calkins, A.S. Cohen, and D. Zucker–Franklin, pp. 149–156, Plenum Press, N.Y., 1986.

Snow, A.D., H. Mar, D. Nochlin, H. Kresse, and T.N. Wight. Unique distribution of a dermatan sulfate proteoglycan (decorin) in the amyloid plaques and neurofibrillary tangles of Alzheimer's disease. 1990 Amer. Soc. Clin. Biochem. Meeting. (abstract).

Snow, A.D., R. Sekiguchi, D. Nochlin, K. Kimata, W.A. Schreier, and D.G. Morgan. A rat model to study the effects of BAP–containing amyloid in brain. 22nd. Annual Meeting Soc. Neurosci., Anaheim, CA. Oct. 25–30, 1992.

Snow, A.D., R. Sekiguchi, D. Nochlin, K. Kimata, W.A. Schreier, and D.G. Morgan. Brain amyloid accumulation in rats within 1 week of continuous infusion of a beta–amyloid protein (1–40) and an amyloid plaque co–component. 3rd. Intl. Conf. on Alzheimer's Dis. and Rel. Dis., Padova, Italy, Jul. 1992. *Neurobiol. Aging* 13(1): p. S101, 1992.

Snow, A.D., Mar, H., Nochlin, D., Kresse, H., and Wight, T.N. Peripheral distribution of dermatan sulfate proteoglycans in amyloid–containing plaques and their presence in the neurofibrillary tangles of Alzheimer's disease. VIth Intl. Symp. on Amyloidosis, Oslo, Norway, Aug. 1990 (abstract).

Snow, A.D., Mar, H., Nochlin, D., Sekiguchi, R., Kimata, K., Koike, Y., and Wight, T.N. Heparan sulfate accumulation in the beta–amyloid protein containing lesions of Alzheimer's disease and Down's syndrome is an early event. VIth Intl. Symp. on Amyloidosis, Oslo, Norway, Aug. 1990. (abstract).

Kowall et al, "An in vivo model for the neurodegenerative effects of β amyloid . . . ", *PNAS 88*: 7247–7251 (Aug. 1991).

Kisilevsky, "Heparan sulfate proteoglycans in Amyloidogenesis . . . " *Lab. Invest.* 63(5):589–591.

Sorimachi et al. Structure determination of extracellular fragments of amyloid proteins. Eur. J. Biochem. 1994, vol. 219, pp. 237–251.

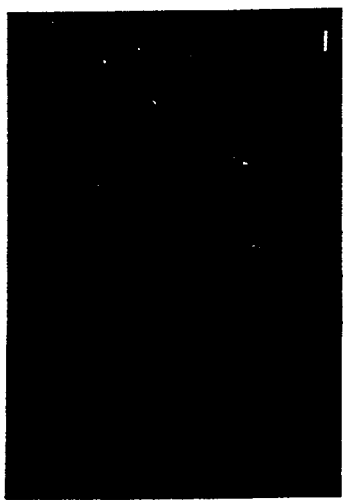
FIG. IA
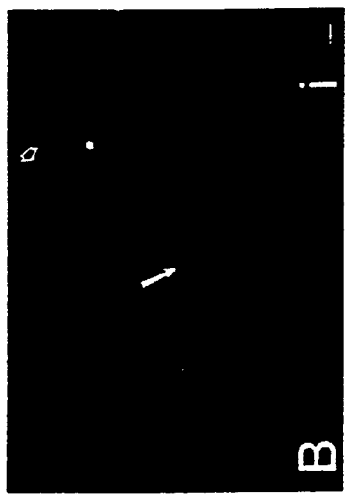
FIG. IB
FIG. IC
FIG. ID
FIG. IE
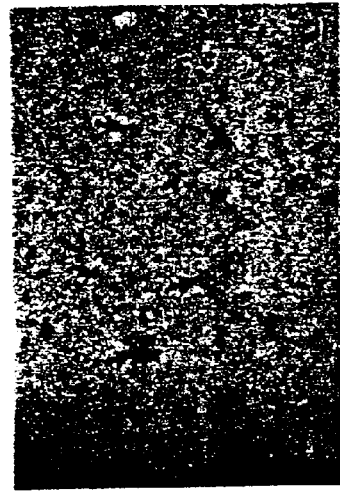
FIG. IF

FIG. 4A  α AA amyloid
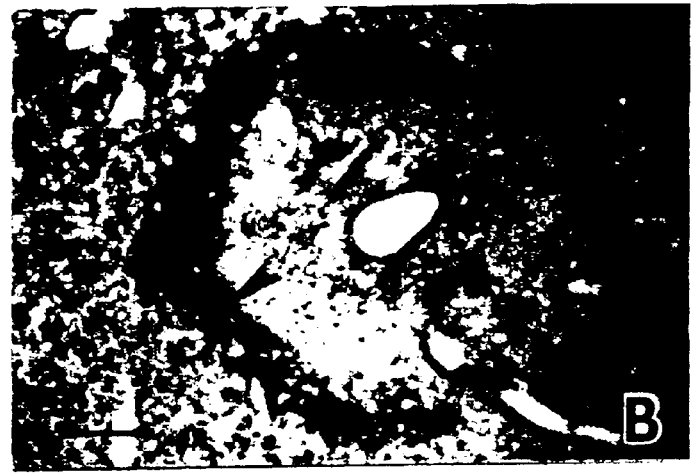
FIG. 4B  αHSPG
FIG. 4C  α BAP

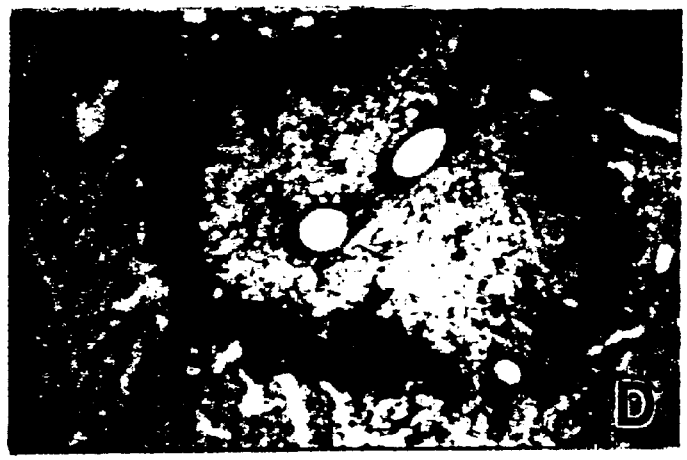
FIG. 4D  BAP peptide → αBAP
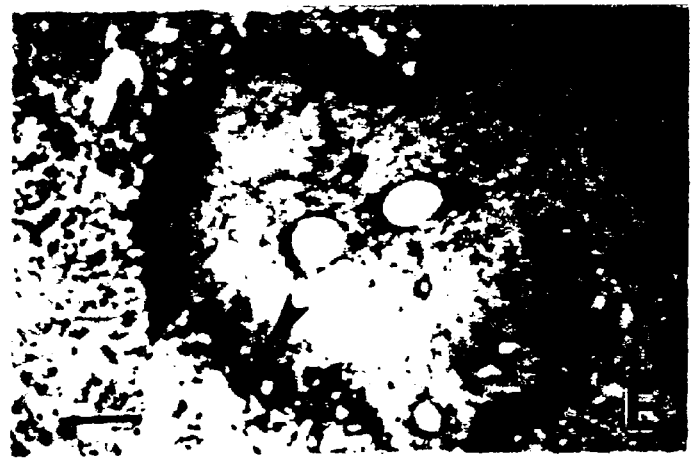
FIG. 4E  Ch ABC → BAP peptide → αBAP
FIG. 4F  nitrous acid → BAP peptide → αBAP

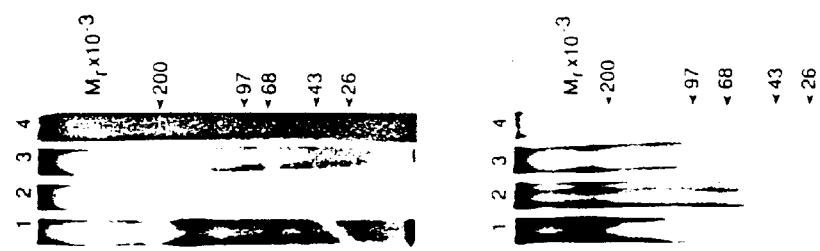
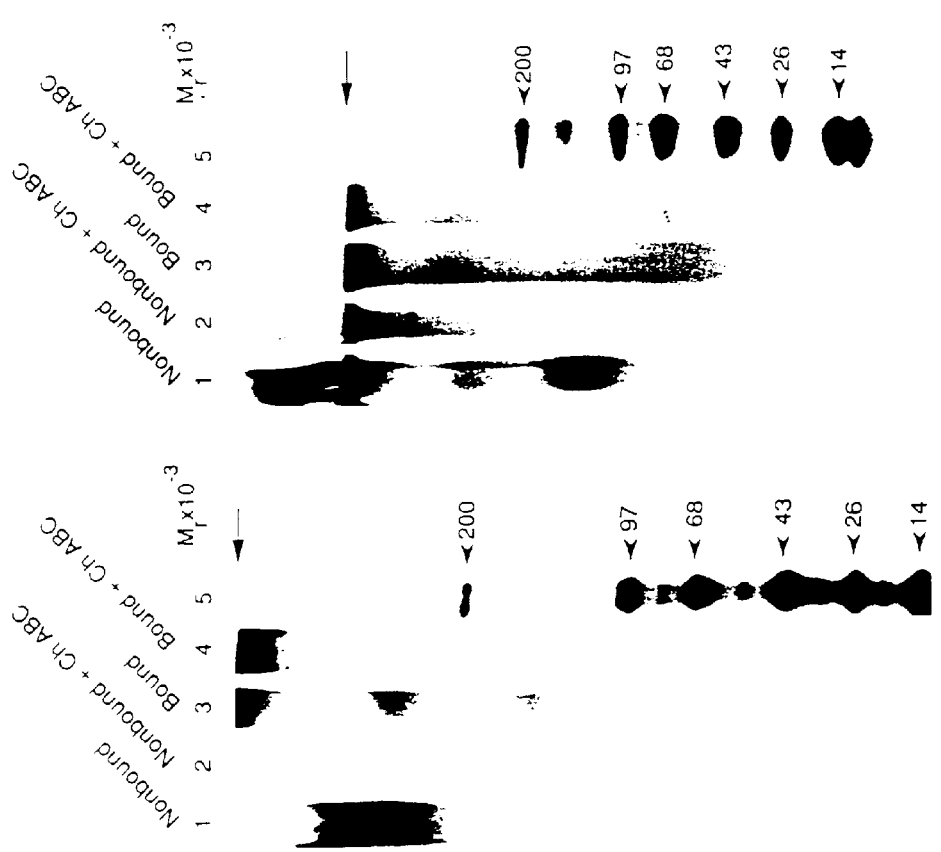
FIG. 7B
FIG. 7D
FIG. 6B
Smooth Muscle Cell PGs
FIG. 6A
Endothelial Cell PGs

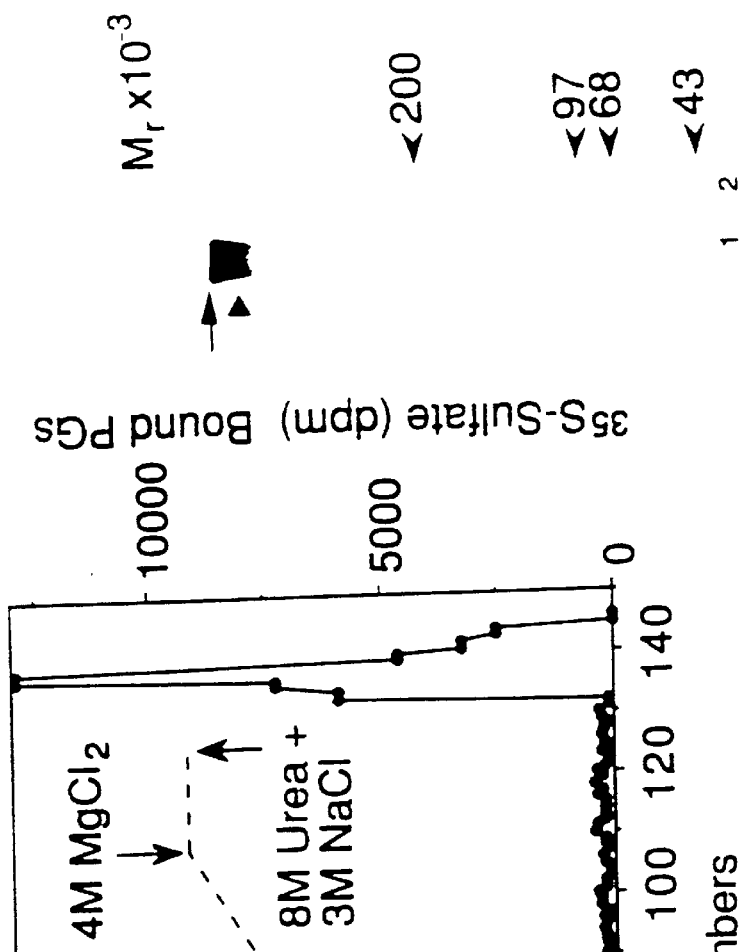
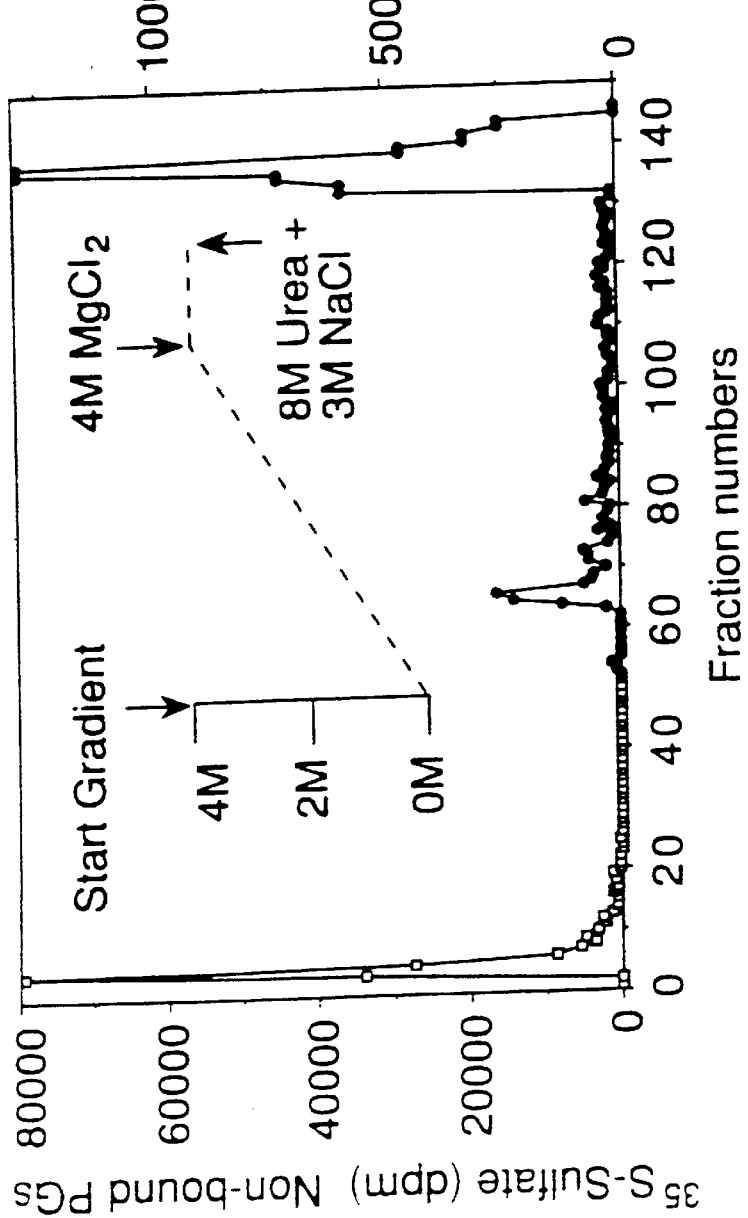
FIG. 9A
FIG. 9B

Endogenous Heparan Sulfate Proteoglycan Accumulation at β/A4 Infusion Site
FIG. 12A — Thioflavin S
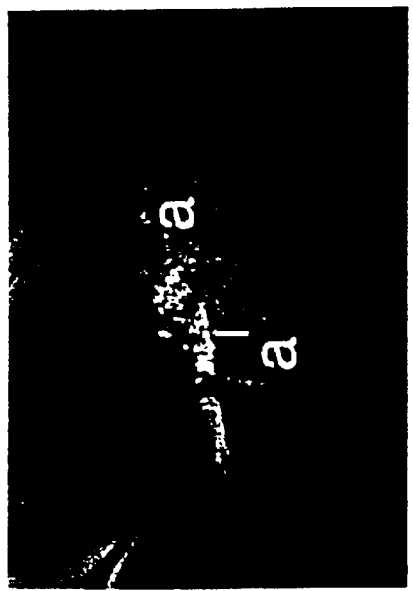
FIG. 12C — αHSPG (core protein)
FIG. 12B — Congo Red
FIG. 12D — αHSPG + HSPG antigen
1 week infusion of β/A4 (1-40) into rat hippocampus

Lack of Congo Red Staining at β/A4 Infusion Site Correlates with a Lack of Endogenous HSPG Accumulation
αβ/A4
(1-40)
*FIG. 13A*
Congo Red
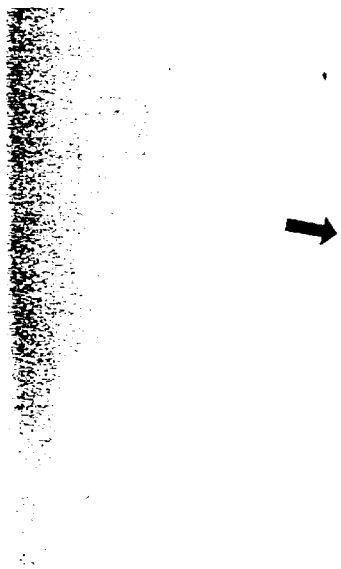
*FIG. 13B*
αHSPG
(core protein)
*FIG. 13C*
1 week infusion of β/A4 (1-40) into rat hippocampus

Co-infusion of Heparan Sulfate Glycosaminoglycans with β/A4 (1-40) Abolishes Congo Red Staining

αβ/A4 (1-40)

αHK-249 (HS GAGs)

Congo Red 1 week co-infusion of β/A4 (1-40) + HS GAGs into rat hippocampus

Alzheimer's Disease

αβ/A4 (1-40)

Thioflavin S

αβ/A4 (1-40)

Thioflavin S 1 week co-infusion of β/A4 (1-40) and heparan sulfate proteoglycans into rat hippocampus

Co-Deposition of β/A4 (1-40) & Heparan Sulfate Proteoglycans
FIG. 18A
α β/A4 (1-40)
A
α HK-249
(Heparan
Sulfate
GAGs)
FIG. 18B B
Rat Infusion Model
(1 week)

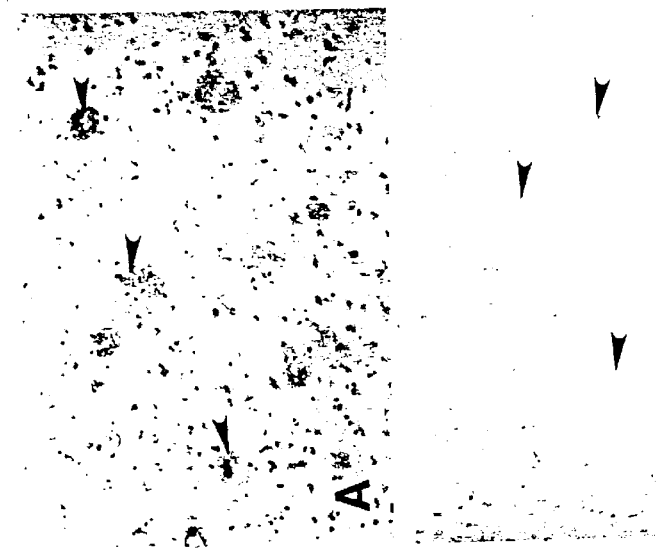
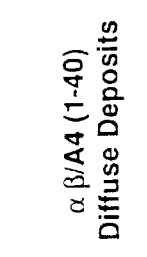
FIG. 19A  α β/A4 (1-40) Diffuse Deposits — Alzheimer's Disease
FIG. 19B  α β/A4 (1-40) Diffuse Deposits — Rat Infusion Model 1 week co-infusion of β/A4 (1-40) & Heparan Sulfate Proteoglycans
FIG. 19C  α β/A4 (1-40) + β/A4 (1-40)

Alz-50 Immunostaining

FIG. 20A

Human Brain

Alzheimer's Disease

FIG. 20B

Rat Hippocampus 1 week Co-infusion of β/A4 (1-40) & HSPGs

FIG. 20C

Rat Hippocampus 1 week infusion of only HSPGs

Alz-50 Immunostaining in Rat Infusion Model 1 week co-infusion of β/A4 (1-40) & HSPGs 1 week infusion of HSPGs only 1 week infusion of HS GAGs only

FIG. 22A — Bielchowsky Silver Staining of Dystrophic Neurites &/or Degenerating Neurons; Alzheimer's Disease; Human Brain

Astrocyte and Macrophage/Microglia Localization in Rat Infusion Model

α GFAP
(astrocytes)

α ED1
(macrophage/
microglia)

1 week co-infusion of β/A4 (1-40) and heparan sulfate proteoglycans into rat hippocampus

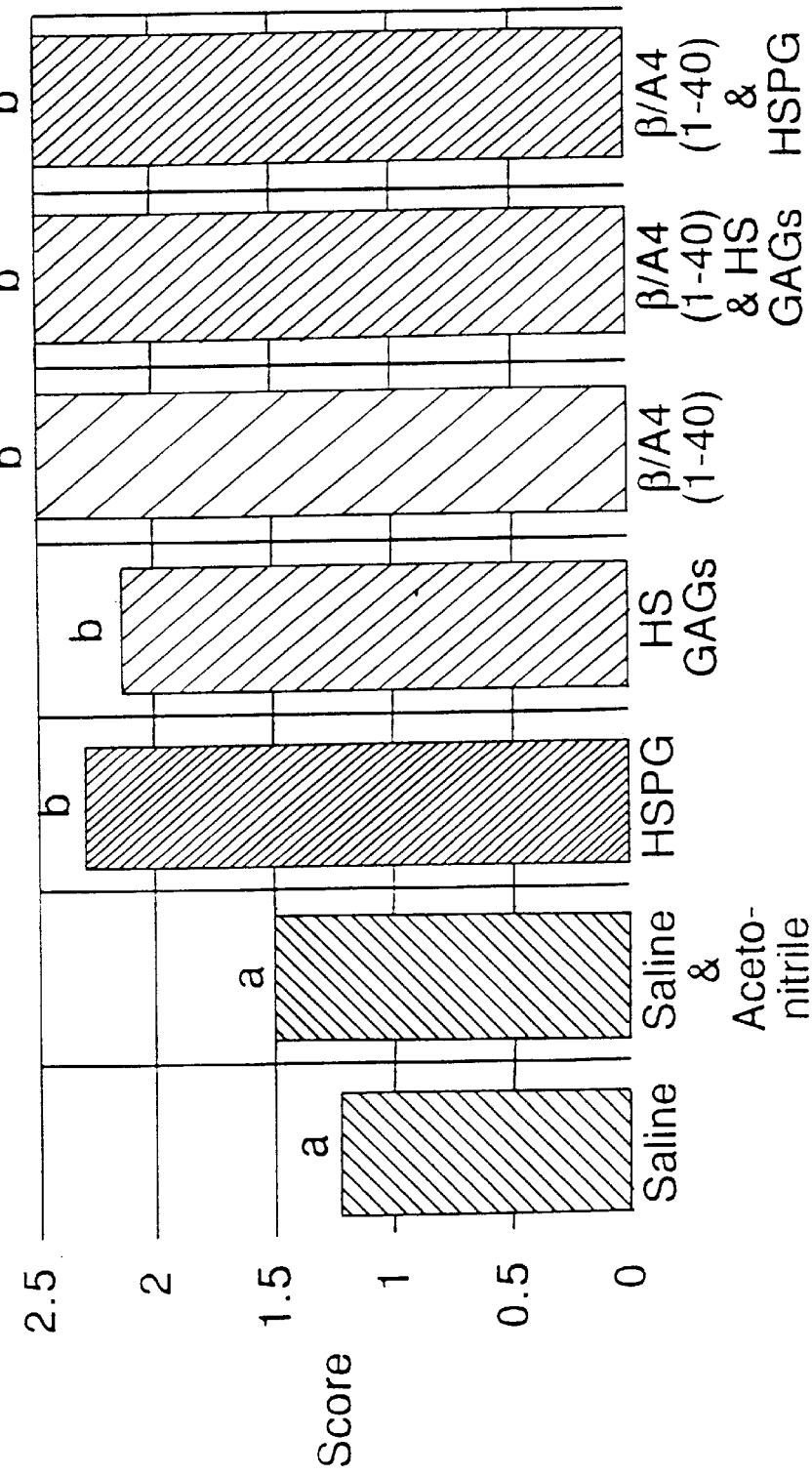

Alzheimer's Disease

Neurofibrillary Tangles

Amyloid Plaques 1 week 7 weeks

Congo Red

Co-infusion of β/A4 (1-40) and heparan sulfate proteoglycans into rat hippocampus

Co-Infusion of β/A4 (1-40) and Heparan Sulfate Proteoglycans into Rat Hippocampus (7 weeks)

Congo Red

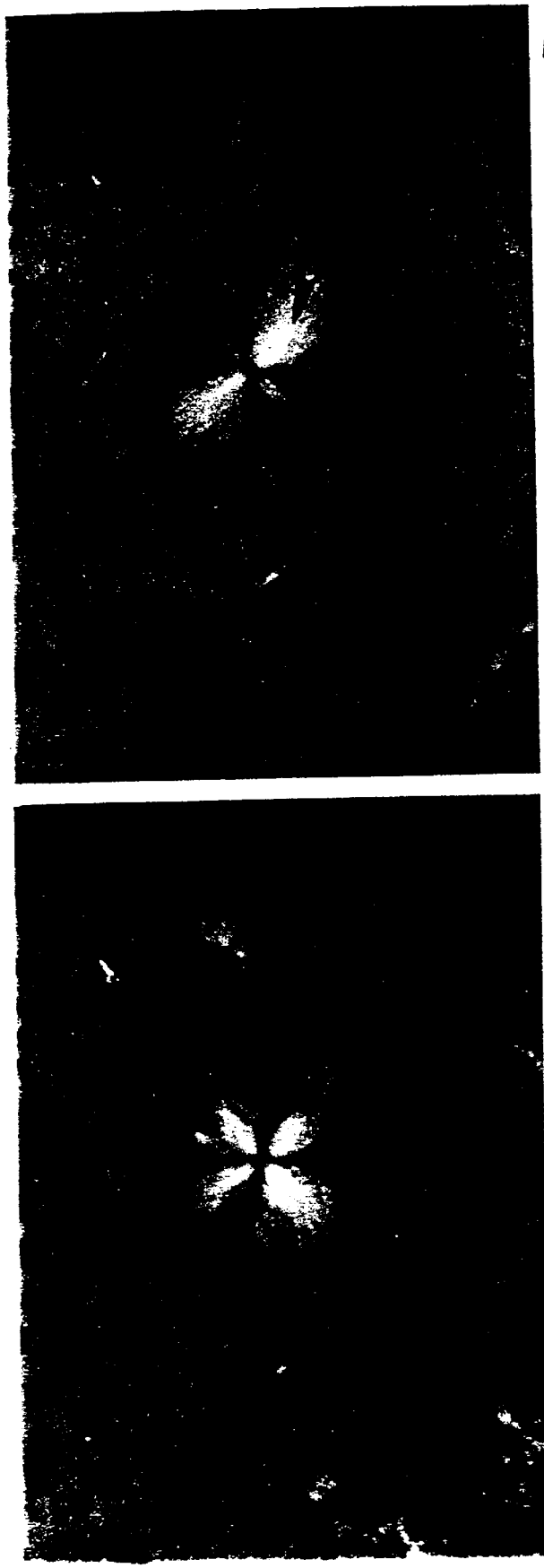

| CURRENT CLASSIFICATION MAJOR PROTEIN IDENTIFIED | PRECEDING OR ASSOCIATED DISEASE | CLINICAL CLASSIFICATION |
|---|---|---|
| AL | NONE | PRIMARY |
| AL | MULTIPLE MYELOMA, B-CELL DYSCRASIA | SECONDARY |
| AA | RHEUMATOID ARTHRITIS, OSTEOARTHRITIS, ANKYLOSING SPONDYLITIS, TB, ABSCESSES, OSTEOMYELITIS, I.V. DRUG USERS, HODGKIN'S DISEASE, RENAL CELL CARCINOMA | |
| AA | FAMILIAL MEDITERRANEAN FEVER | FAMILIAL |
| PREALBUMIN | FAMILIAL AMYLOIDOTIC POLYNEUROPATHY | |
| CYSTATIN-C | HEREDITARY AMYLOID ANGIOPATHY-ICELANDIC | |
| AL | PULMONARY NODULES | ISOLATED |
| PREALBUMIN | CARDIAC | |
| CALCITONIN VARIANT | ISLETS OF LANGERHANS | |
| PROCALCITONIN | MEDULLARY CARCINOMA OF THYROID | |
| BETA2-MICROGLOBULIN | CHRONIC HEMODIALYSIS | |
| B/A4 | ALZHEIMER'S DISEASE; DOWN'S SYNDROME; | |
| PrP | CJD; GSS; SCRAPIE; | |

THE PRESENCE OF PROTEOGLYCANS AND/OR
GLYCOSAMINOGLYCANS IN DIFFERENT TYPES OF AMYLOID

| Type of Amyloid | Evidence for Presence of PGs and/or GAGs |
|---|---|
| AA amyloid | (12‡, 32‡, 33‡, 70‡, 101‡, 118*, 125†, 134*, 139‡, 163‡, 168*, 169‡, 170*, 178†) |
| AL amyloid | (12‡, 32‡, 118*, 170*) |
| Endocrine amyloid (AE) | (170*) |
| Beta$_2$-microglobulin | Snow and Kisilevsky§ |
| Senile cardiac amyloid (prealbumin) | (170)* |
| Familial amyloidotic polyneuropathy (prealbumin) | Snow, Wight & Saraiva§ |
| Beta-amyloid (Alzheimer's) neuritic plaques congophilic angiopathy neurofibrillary tangles | (170*, 171*, 173†) |
| Beta-amyloid (Down's Syndrome) neuritic plaques congophilic angiopathy | Snow, Nochlin, Mar, Kimata, Kato, Hassell and Wight§ |
| Beta-amyloid (aged mammals) neuritic plaques congophilic angiopathy | Snow, Wight, Cork and Price§ |
| Cerebral hemorrhage related CA Icelandic CA (cystatin C) Dutch familial cerebral hemorrhage with congophilic angiopathy (beta-amyloid) | Snow, Wight & Vinters§ |
| PrP protein (amyloid plaques) CJD GSS kuru hamster scrapie | (175†, 177*, 182†) |

Histochemical, immunocytochemical and/or biochemical data suggest that PGs and/or GAGs are present in a variety of different types of amyloid.

*Alcian blue—MgCl$_2$ staining according to the "critical electrolyte concentration" method (156).

†Verified by immunocytochemistry with specific probes to PGs/GAGs.

‡Verified by biochemical analysis.

§Unpublished data.

Testing of Glycosaminoglycans and Related Macromolecules as Potential Inhibitors of β/A4 Amyloid Deposition Stage 1: Potential Inhibitors of HSPG Binding to β/A4

Methodology:
a) slot blot assays
b) affinity column chromatography
c) solid phase binding assays

FIG. 36

Testing of Glycosaminoglycans and Related
Macromolecules as Potential Inhibitors of
β/A4 Amyloid Deposition Stage 2: Influence of Potential Inhibitors
on β/A4 Conformation Methodology:
a) in vitro-congo red assays
b) conformational effects-analyzed
   by electron microscopy
c) conformational effects-analyzed
   by circular dichroism spectroscopy

FIG. 37

Testing of Glycosaminoglycans and Related Macromolecules as Potential Inhibitors of β/A4 Amyloid Deposition Stage 3: Influence of Potential Inhibitors on β/A4 Amyloid Deposition in Rat Infusion Model a) prevent β/A4 amyloid deposition when co-infused
b) diminish β/A4 amyloid accumulation after it has deposited in brain

FIG. 38

Testing of Glycosaminoglycans and Related Macromolecules as Potential Inhibitors of β/A4 Amyloid Deposition Stage 4: Demonstrating Non-Toxicity of Potential Inhibitors Methodology:
a) in vitro assays
b) in vivo assays

FIG. 39

Testing of Glycosaminoglycans and Related Macromolecules as Potential Inhibitors of β/A4 Amyloid Deposition Stage 5: Human Clinical Trials at University of Washington Alzheimer's Disease Research Center Methodology:
a) short term studies-cognitive improvement?
b) long term studies-cognitive improvement?
β/A4 amyloid in brain at autopsy?

| | SALINE | SALINE & ACETONITRILE | HSPG | HS GAGs | β/A4 (1-40) | β/A4 (1-40) & HS GAGs | β/A4 (1-40) & HSPG |
|---|---|---|---|---|---|---|---|
| 1) Congo Red Staining | $0^a$ | $0^a$ | $0^a$ | $0^a$ | $1.95^c$ | $0.70^b$ | $2.48^c$ |
| 2) Thioflavin S Staining | $0^a$ | $0^a$ | $0^a$ | $0^a$ | $2.30^c$ | $0.90^b$ | $2.55^c$ |
| 3) β/A4 (1-40) immunostaining | $0^a$ | $0^a$ | $0.5^a$ | $0^a$ | $2.50^b$ | $2.33^b$ | $2.50^b$ |
| 4) HSPG core protein (polyclonal) immunostaining | $0.40^a$ | $0.50^a$ | $2.83^b$ | $0.25^a$ | $2.50^b$ | $0.50^a$ | $2.75^b$ |
| 5) HS GAG (HK-249) immunostaining | $0.75^a$ | $0^a$ | $2.00^b$ | $2.50^b$ | $2.38^b$ | $2.50^b$ | $3.00^b$ |
| 6) Alz-50 immunostaining | $1.00^a$ | $1.50^a$ | $0.75^a$ | $0.75^a$ | $2.68^b$ | $2.50^b$ | $2.70^b$ |
| 7) ED1 immunostaining | $1.25^a$ | $1.50^a$ | $2.33^b$ | $2.17^b$ | $2.50^b$ | $2.50^b$ | $2.50^b$ |
| 8) Number of Silver Positive Neurons | $4.00^a$ | $3.75^a$ | $15.50$ | $11.00^a$ | $11.83$ | $3.27^a$ | $24.25^b$ |

Scoring Legend for Staining or Immunostaining (Rows 1-7): 0 = negative; 1 = slightly positive; 2 = moderately positive; 3 = strongly positive Statistical significance: Groups with different letters (a, b or c) are significantly different from each other ($p<0.05$-$0.01$). Groups with the same letter are not significantly different. Groups with no letters are not significantly different from any of the other groups.

SEQUENCE LISTING (1) GENERAL INFORMATION:

(iii) NUMBER OF SEQUENCES:7

(2) INFORMATION FOR SEQ ID NO:1:

(i) SEQUENCE CHARACTERISTICS:
      (A) LENGTH:40 amino acids (B) TYPE:amino acid (C) STRANDEDNESS:single (D) TOPOLOGY:linear (ii) MOLECULE TYPE:peptide
      (A) DESCRIPTION: /A4(1-40); FIGURES 23-29

(ix) SEQUENCE DESCRIPTION: SEQ ID NO:1:

Asp Ala Glu Phe Arg His Asp Ser Gly Tyr Glu Val His His Gln
                 5                10               15

Lys Leu Val Phe Phe Ala Glu Asp Val Gly Ser Asn Lys Gly Ala
              20                25              30

Ile Ile Gly Leu Met Val Gly Gly Val Val
              35               40

(2) INFORMATION FOR SEQ ID NO:2:

(i) SEQUENCE CHARACTERISTICS:
      (A) LENGTH:28 amino acids (B) TYPE:amino acid (C) STRANDEDNESS:single (D) TOPOLOGY:linear (ii) MOLECULE TYPE:peptide
      (A) DESCRIPTION: /A4(1-28); page 83, line 31

(ix) SEQUENCE DESCRIPTION: SEQ ID NO:2:

Asp Ala Glu Phe Arg His Asp Ser Gly Tyr Glu Val His His Gln
                 5                  10                  15

Lys Leu Val Phe Phe Ala Glu Asp Val Gly Ser Asn Lys
                20                  25

(2) INFORMATION FOR SEQ ID NO:3:

(i) SEQUENCE CHARACTERISTICS:
        (A) LENGTH:6 amino acids (B) TYPE:amino acid (C) STRANDEDNESS:single (D) TOPOLOGY:linear (ii) MOLECULE TYPE:peptide
        (A) DESCRIPTION: /A4(12-17); page 60,
                        line 4-5; page 83, line 33 and (ix) SEQUENCE DESCRIPTION: SEQ ID NO:3:

Val His His Gln Lys Leu
                 5

(2) INFORMATION FOR SEQ ID NO:4:

(i) SEQUENCE CHARACTERISTICS:
        (A) LENGTH:28 amino acids (B) TYPE:amino acid (C) STRANDEDNESS:single (D) TOPOLOGY:linear (ii) MOLECULE TYPE:peptide
        (A) DESCRIPTION: /A4(1-28) mutant; page
                        83, lines 27-28

(ix) SEQUENCE DESCRIPTION: SEQ ID NO:4:

Asp Ala Glu Phe Arg His Asp Ser Gly Tyr Glu Val Gly Gly Gln
                 5                  10                  15

Lys Gly Val Phe Phe Ala Glu Asp Val Gly Ser Asn Lys
                20                  25

(2) INFORMATION FOR SEQ ID NO:5:

(i) SEQUENCE CHARACTERISTICS:
        (A) LENGTH:7 amino acids (B) TYPE:amino acid (C) STRANDEDNESS:single (D) TOPOLOGY:linear (ii) MOLECULE TYPE:peptide
        (A) DESCRIPTION: APP(98-104); page 84, lines 8-13

(ix) SEQUENCE DESCRIPTION: SEQ ID NO:5:

Cys Lys Arg Gly Arg Lys Gly
                 5

(2) INFORMATION FOR SEQ ID NO:6:

(i) SEQUENCE CHARACTERISTICS:
        (A) LENGTH:11 amino acids (B) TYPE:amino acid (C) STRANDEDNESS:single (D) TOPOLOGY:linear (ii) MOLECULE TYPE:peptide
        (A) DESCRIPTION: /A4(176-186); page 84,
                    lines 8-13

(ix) SEQUENCE DESCRIPTION: SEQ ID NO:6:

Leu Arg Val Ile Tyr Glu Arg Met Asn Gln Ser
              5                    10

(2) INFORMATION FOR SEQ ID NO:7:

(i) SEQUENCE CHARACTERISTICS:
        (A) LENGTH:8 amino acids (B) TYPE:amino acid (C) STRANDEDNESS:single (D) TOPOLOGY:linear (ii) MOLECULE TYPE:peptide
        (A) DESCRIPTION: APP(324-331); page 84, lines 8-13

(ix) SEQUENCE DESCRIPTION: SEQ ID NO:7:

Glu Ala Lys His Arg Glu Arg Met

ANIMAL MODELS OF HUMAN AMYLOIDOSES

This application is a continuation of application Ser. No. 07/969,734, filed Oct. 23, 1992, now abandoned, which is a continuation-in-part of application Ser. No. 07/950,417, filed Sep. 23, 1992, now abandoned.

TECHNICAL FIELD

The invention provides animal models for the evaluation of candidate drugs and therapies for the prevention and treatment of amyloidoses, including Alzheimer's disease. For example, a rapid animal model of congophilic and fibrillar β/A4 amyloid deposition in brain is provided for in vivo screening of candidate therapeutic agents and protocols. Heparin, heparan sulphate glycosaminoglycans, and related macromolecules, as well as heparin-binding peptides, are provided as therapeutic agents for amyloid deposition in Alzheimer's disease brain and other amyloidoses.

BACKGROUND OF THE INVENTION

Amyloid and amyloidosis. Amyloid is a generic term referring to a group of diverse, but specific extracellular protein deposits which all have common morphological properties, staining characteristics and x-ray diffraction spectra. Regardless of the nature of the amyloid protein deposited all amyloids have the following characteristics: 1) an amorphous appearance at the light microscopic level and appear eosinophilic using hematoxylin and eosin stains; 2) all stain with congo red and demonstrate a red/green birefringence as viewed under polarized light; 3) all contain a predominant beta-pleated sheet secondary structure; and 4) ultrastructurally amyloid usually consists of non-branching fibrils of indefinite length and with a diameter of 8–12 nm.

Amyloidosis: Early Historical Perspectives

Rokitansky in 1842 was the first to observe waxy, eosinophilic tissue deposits in a number of tissues from different patients. However, it wasn't until 1854 when Virchow termed these deposits as "amyloid" meaning "starch-like" since they gave a positive staining with the sulfuric acid-iodine reaction, which was used in the 1850s for demonstrating cellulose. Although cellulose is not a constituent of amyloid, nonetheless, the staining that Virchow observed is probably due to the presence of different carbohydrates, known as highly sulfated glycosaminoglycans and proteoglycans, which appear to be associated with all types of amyloid deposits (see below). The name amyloid has remained despite the fact that Freiderich & Kekule in 1859 discovered the protein nature of amyloid.

Amyloid is Not a Single Disease

For many years, based on the fact that all amyloids have the same staining and structural properties, lead to the postulate that a single pathogenetic mechanism was involved in amyloid deposition, and that amyloid deposits were thought to be composed of a single set of constituents. Current research has clearly shown that amyloid is not a uniform deposit and that amyloids may consist of different protein which are totally unrelated.

Amyloidosis is Not an "Immune Disorder"

It is interesting that the pathology textbook by Robbins has "amyloidosis" under the heading of "possible immune disorders". Obviously these authors thought like many of the predecessors studying amyloidosis in the 1960s and 1970s. This is based on a number of early observations made about amyloidosis. 1) Clinically, many types of amyloid were due to a complication of long-standing inflammatory disorders such as rheumatoid arthritis or osteomyelitis. 2) Histologically, tissue reactions in many of these disorders were characterized by the presence of immunologically competent cells (e.g. monocytes, macrophages, plasma cells. 3) Amyloid was developed in animals used for raising antisera. Repeated injections of antigens were not uncommonly followed by systemic amyloid deposits. Therefore, clinical, histological, and experimental data focused attention, not illogically, upon the immune system. However, by the mid-late 1970s, the isolation, characterization and sequencing of amyloid proteins from different clinical settings showed that a basic immunological disturbance could not account for the diversity of proteins seen as amyloids in the different diseases.

Clinical Classification of Amyloidosis

Let's look at how amyloid was classified initially in the mid to late 1970s and then compare it to the classification according to protein type which is used today. Basically, amyloid was clinically classified into 4 groups, primary amyloid, secondary amyloid, familial amyloid, and isolated amyloid.

Primary amyloid, is amyloid appearing de novo, without any preceding disorder. In 25–40% of these cases, primary amyloid was the antecedent of plasma cell dysfunction such as the development of multiple myeloma or other B-cell type malignancies. Here the amyloid appears before rather than after the overt malignancy. Regardless of which clinical element appeared first, the type of amyloid protein in primary amyloid is most often the same as that seen in amyloid secondary to a variety of B-cell dysfunctions.

Secondary amyloid, appears as a complication of a previously existing disorder. 10–15% of patients with multiple myeloma eventually develop amyloid. Patients with rheumatoid arthritis, osteoarthritis, ankylosing spondylitis can develop secondary amyloidosis as with patients with tuberculosis, lung abscesses and osteomyelitis. Intravenous drug users who self-administer and who then develop chronic skin abscesses can also develop secondary amyloid. Secondary amyloid is also seen in patients with specific malignancies such as Hodgkin's disease and renal cell carcinoma. Although these were all initially classified as secondary amyloid, once the amyloid proteins were isolated and sequenced, many of these turned out to contain different amyloid proteins.

The familial forms of amyloid also show no uniformity in terms of the peptide responsible for the amyloid fibril deposited. Several geographic populations have now been identified with genetically inherited forms of amyloid. One group is found in Israel, predominantly among Sephardic Jews, and this disorder is called Familial Mediterranean Fever and it is characterized by amyloid deposition, along with recurrent inflammation and high fever. Another form of inherited amyloid is known as Familial Amyloidotic Polyneuropathy, and it has been found in at least three nationalities, namely, Swedish, Portuguese and Japanese. Amyloid deposition in this disease occurs predominantly in the peripheral and autonomic nerves. Hereditary amyloid angiopathy of Icelandic origin is a autosomal dominant form of amyloid deposition primarily affecting the vessels in the brain, and has been identified in 128 members distributed in at least 8 families restricted to a small geographic area of western Iceland. These patients clinically have massive cerebral hemorrhages in early life which usually causes death before the age of 40.

The primary, secondary and familial forms of amyloid that I have so far described tend to involve many organs of the body including heart, kidney, liver, spleen, GI tract and skin.

Isolated forms of amyloid, on the other hand, tend to involve a single organ system. Isolated amyloid deposits have been found in the lung, and heart. Up to 90% of type II diabetic patients (non-insulin form of diabetes) have isolated amyloid deposits in the pancreas restricted to the beta cells in the islets of Langerhans. Isolated forms of amyloid have also been found in endocrine tumors which secrete polypeptide hormones such as in medullary carcinoma of the thyroid. A serious complication of long-term hemodialysis is amyloid deposited in the medial nerve and clinically associated with carpal tunnel syndrome. By far the most common type of organ-specific amyloid, and amyloid in general, is that found in the brains of patients with Alzheimer's disease. In this disorder, amyloid is predominantly restricted to the central nervous system (CNS). Similar deposition of amyloid in the brain occurs in Down's syndrome patients once they reach the age of 35 years. Other types of CNS amyloid deposition include rare but highly infectious disorders such as Creutzfeldt-Jakob disease, Gerstmann-Straussler syndrome and scrapie in animals.

Current Classification of Amyloid: By Protein Type

It was misleading to group the various amyloidotic disorders strictly on the basis of their clinical features since, as shown in FIG. 34, when the major proteins involved were isolated and sequenced, they turned out to be different. For example, amyloid seen in rheumatoid arthritis and osteoarthritis, now known as AA amyloid, was the same amyloid protein identified in patients with the familial form of amyloid known as Familial Mediterranean Fever. Not to confuse this issue, it was decided that the best classification of amyloid should be according to the major protein type found, once it was isolated, sequenced and identified.

AA Amyloid

AA amyloid is common to a host of seemingly unrelated disorders including long-standing inflammation, various forms of malignancy, and in Familial Mediterranean Fever. Also it is the type of amyloid formed in animal models which use daily repeated injections of antigens. A potent antigen used today is casein or azocasein. In these animals, amyloid deposition occurs in the spleen, liver and kidney within 7–10 days of repeated injections.

The isolated amyloid protein in these cases turns out to be approximately 76 amino acids long, and having a MW of about 8,500. These 76 amino acids correspond to the amino terminal ⅔s of a naturally occurring serum protein known as SAA (Serum amyloid A). SAA is known to be an acute phase protein whose concentration increases about a thousand-fold, usually within 24 hours, during any inflammatory disorder. It is mainly made by the liver but current research also suggests that it can be found in other tissues as well. It's normal function at this time is not really known. The AA amyloid protein that is deposited in the tissues is identical from patient to patient, regardless of the nature of the inflammatory disorder that has preceded its deposition. The AA amyloid protein is essentially the same protein found in many other species including mice, ducks, mink and monkeys. This conservation is probably due to the important, yet unknown, role that the precursor (SAA) plays during the process of inflammation.

AL Amyloid

Another major type of amyloid protein that has been identified is known as AL amyloid usually due to the deposition of the variable region of immunoglobulin light chains, either lambda or kappa chains; but it may also consist of the entire light chain. Since AL amyloid represents the variable region of light chains, AL amyloid isolated from different patients differs in its amino acid sequence. However, within a single patient the sequence of the AL amyloid protein is constant regardless of the organ from which the amyloid is isolated. This amyloid usually occurs secondary to multiple myeloma, or B-cell type malignancies (ex. immunoblastic lymphomas) and other plasma cell dyscrasias. Not all patients with multiple myeloma develop AL amyloid. Only 10–15% develop clinical problems related to these amyloid deposits, whereas a larger percent may have only microscopic deposits. Why all patients with immunoglobulin secreting abnormalities do not develop this type of amyloid is not known.

Prealbumin or Transthyretin

Another type of amyloid protein that has been identified is known as prealbumin or transthyretin. Prealbumin refers not to the precursor of circulating albumin, but to the serum protein that, in standard electrophoretic separation, migrates ahead of albumin. Prealbumin or transthyretin is normally the serum carrier of thyroxine, as well as retinol binding protein and retinoic acid. It has a normal plasma concentration of 20–40 mg/dL and is synthesized by the liver, and consists of 127 amino acids. A variant protein has been found in most types of Familial Amyloidotic Polyneuropathy (FAP) both the normal and the abnormal forms of transthyretin are found in the deposits, but the latter tend to predominate. Single amino acid substitutions have been identified at positions 30, 33, 60, 77, 84, 111 and 122 of the prealbumin molecule in the circulating plasma and in amyloid deposits of FAP patients. The most common substitution is a methionine for valine at position 30 of the prealbumin molecule. It is not clear how these amino acid substitutions allow to change the metabolic characteristics of transthyretin such that it is deposited primarily in peripheral and autonomic nerves. Immunological, chemical and direct DNA tests have been developed for detection of the specific mutations in the prealbumin variants. These assays are useful in identification of family members at risk while still in the preclinical phase of the disease.

A similar prealbumin molecule is deposited in the heart in an isolated form of myloid known as senile cardiac amyloid. This type of amyloid is a frequent postmortem finding in patients more than 80 years of age and has been generally regarded as nonspecific.

Beta$_2$-Microglobulin

Another recent type of amyloid protein which has been identified is known as beta$_2$-microglobulin. This type of amyloid has become recognized as a serious complication of long-term hemodialysis. Its most prominent clinical presentation is the carpal tunnel syndrome. Other manifestations include joint swelling, multiple spontaneous fractures and radiolucency in the wrist and hip. Its incidence correlates mainly with the number of years spent on dialysis, usually up to 50% of patients on hemodialysis over 8–10 years develop this type of amyloid. Beta$_2$microglobulin is a single polypeptide chain of 100 amino acid residues and has a MW of about 11,800. Beta$_2$-microglobulin accumulates not only in the blood of uremic patients but also in the synovial fluid and in the tissues. The pathogenesis of dialysis amyloidosis is poorly understood. Some investigators have speculated that dialysis membrane characteristics may play a role, but this is controversial.

Procalcitonin

Several forms of isolated amyloid associated with endocrine tumors have been recently described. Where there are data characterizing the protein, the amyloid is derived from a portion of the normal hormonal product secreted (or prehormone synthesized) by the cells from which the tumor arises. Medullary carcinoma of the thyroid is such an example. The tumor is related to the C-type cells of the thyroid, which normally secrete calcitonin. Immunological studies have demonstrated that the amyloid in these tumors is a fragment of procalcitonin. A variant of calcitonin has been identified as the amyloid seen in the Islets of Langerhans in patients with diabetes. Atrial natriuretic factor, or a portion thereof, is deposited in isolated atrial amyloid.

Beta Amyloid Protein or β/A4

Clinically the most common form of amyloidosis, is the type that is deposited in the brains of patients with Alzheimer's disease, as well as in Down's syndrome patients, usually over the age of 35. The amyloid protein deposited is now known as the beta-amyloid protein or β/A4 (due to its known MW of approximately 4,200). It is derived from a larger precursor molecule known as the beta-amyloid precursor protein. This latter protein may take on different forms, including proteins of 695, 714, 751 and 770 amino acids, since the BAPP gene produces at least four principal mRNAs through alternative splicing of two exons.

PrP Protein

The last type of amyloid protein which I will discuss, which has been identified is known as the PrP protein or PrP 27–30, due to its having a MW of 27,000–30,000. This protein is also known as the prion protein PrP 27–30 was found to be derived from a larger protein, known as PrP Sc.

These proteins are highly infectious and are transmissible. They are found in the amyloid deposits in rare neurological disease such as Creutzfeldt-Jakob Disease, Gerstmann Strausiler Syndrome, and kuru.

These diseases are usually rapidly progressive neurological disorders characterized by dementia, and fall into the category of subacute spongiform encephalopathies. Microscopically, the cerebral tissue is characterized by neuronal loss, gliosis, spongiform changes and extracellular amyloid deposits in the form of plaques. This type of amyloid deposition is also seen in sheep and hamsters and is known as scrapie. Recent evidence suggests that a small nucleic acid may be present, therefore, it may be regarded as a viral form of amyloidosis.

General Pathogenetic Mechanisms in Amyloidosis

Although amyloid deposits in all clinical conditions share common physical properties relating to the presence of a beta-pleated sheet conformation, it is now clear that many different chemical types exist and additional ones are likely to be described in the future. You may see that there are several common pathogenetic mechanisms that may be operating in amyloidosis in general. In most cases, a circulating precursor protein may result from overproduction of either intact or aberrant molecules (plasma cell dyscrasias), reduced degradation or excretion (SAA in some secondary amyloid syndromes and beta$_2$-microglobulin in long-term hemodialysis), or genetic abnormalities associated with variant proteins (FAP). Proteolysis of a larger protein precursor molecule occurs in many types of amyloidosis, resulting in the production of lower MW fragments that polymerize and assume a beta-pleated sheet conformation as tissue deposits, usually in an extracellular location. What are the precise mechanisms involved, and the aberrant causes leading to changes in proteolytic processing and/or translational modifications is not known in most amyloids.

Proteoglycans and glycosaminoglycans in amyloidosis: a specific component of all amyloids (FIG. 35).

The presence of PGs and/or GAGs associated with amyloid has been known for some time. Virchow (1854) first suggested the presence of carbohydrate in amyloid deposits, when he demonstrated positive iodine staining in organs infiltrated with amyloid indicating the presence of starch or cellulose. This material was termed "amyloid" meaning "starch-like". Friedrich and Kekule (1859) later demonstrated the protein nature of these deposits.

It was not until the late 1960s and early 1970s that the true nature of the carbohydrate present in amyloid deposits was determined. Increased amounts of GAGs (referred to as "acid mucopolysaccharides") were demonstrated in tissue from human autopsies which were infiltrated with amyloid (Berenson et al., 1969; Bitter and Muir, 1965; 1966; Dalferes et al., 1967; 1968; Mowry and Scott, 1967; Okuyara and Turumi, 1963; Pennock et al., 1968; see the appended Citations). Acid mucopolysaccharides were also described in the experimental induction of amyloidosis (Dalferes et al., 1968). Usually highly sulfated GAGs, such as heparan sulfate were increased in the amyloidotic liver and spleen of the AA and AL forms of amyloid (Bitter and Muir, 1966; Okuyara and Turumi, 1963; Pennock et al., 1968) whereas in cardiac tissue infiltrated with amyloid (i.e. senile cardiac amyloid) hyaluronic acid was shown to be the main GAG (Berenson et al., 1969). Since these studies only assessed the GAG composition in amyloid deposits obtained at end stages of the disease process (at autopsy), there was no indication of whether GAG accumulation was a primary, secondary or concurrent process with amyloid deposition. In addition the precise location of GAG accumulation in relation to amyloid deposition was also not known.

In 1985, Snow and Kisilevsky demonstrated that both highly sulfated GAGs and the amyloid protein were deposited in tissues (spleen, liver and kidney) at virtually the same time and in the exact same location using an experimental model of AA or inflammation-associated amyloidosis. In two different models of amyloid induction, neither the nature of the inflammatory inducing agent nor the length of time of the inflammatory reaction influenced the concurrent deposition of amyloid protein and GAGs. This initial study suggested that highly sulfated GAGs such as heparan sulfate, heparin and/or keratan sulfate were involved. These results indicated that the accumulation of GAGs was not a general reaction to an inflammatory stimulus but was specifically related to amyloid deposition itself A subsequent study (Snow et al., 1987) confirmed that heparan sulfate and/or heparin were the only GAGs accumulating in the spleen in association with the AA amyloid protein. In this latter investigation plasma GAGs were found to be elevated (2–3 fold) at the time of GAG deposition in the tissues (spleen, liver). However, since most of this increase was due to chondroitin-4-sulfate, it suggested that the heparan sulfate/heparin increase observed in the tissues was probably derived from the accumulation of GAGs synthesized at the sites of amyloid deposition. Experiments using radioactive precursors for GAG synthesis demonstrated that a significant increase in GAG synthesis occurs in amyloidotic tissue in comparison to controls (Snow, unpublished data).

Although the sites of GAG synthesis in various systemic organs during amyloid deposition has not yet been identified, light microscopic (Snow et al., 1987; Snow et al., 1988) and ultrastructural (Snow et al., 1991) studies suggest that endothelial cells and/or reticuloendothelial cells may be involved. In fact, the initial accumulation of GAGs and amyloid in experimental AA amyloidosis occurs in the perifollicular sinusoids of the spleen and the walls of the central veins in the liver, two sites having a predominance of reticuloendothelial and/or endothelial cells.

Some of the first clear evidence for an intimate relationship between AA amyloid and highly sulfated PGs (such as heparan sulfate) are derived from an ultrastructural study which demonstrates positive Ruthenium red and Cuprolinic blue staining associated with amyloid fibrils in both amyloidotic spleen and liver, as well as in isolated fibril preparations (Snow et al., 1987). These cationic dyes stain sites enriched in PGs.

Recent immunocytochemical evidence confirms the histochemical results and demonstrates that heparan sulfate is specifically localized to sites of amyloid deposition in the mouse model of AA amyloidosis (Snow et al., 1991). Both an affinity-purified polyclonal antibody and a monoclonal antibody (HK-102), each recognizing specific domains on the protein core of a basement-membrane derived heparan sulfate proteoglycan (HSPG) localized HSPG core protein to the sites of amyloid deposition in both spleen and liver in experimental AA amyloidosis. In addition, a monoclonal antibody (HK-249) directed against the GAG chains of the basement-membrane derived HSPG demonstrated that the GAG chains were also localized to these same areas of amyloid deposition (Snow, Kisilevsky, Kimata, Kato and Wight, unpublished data). Furthermore, immunogold labelling at the ultrastructural level (Snow et al., 1991) demonstrated that the protein core of the HSPG was localized primarily to the amyloid fibrils which accumulate in the spleen and liver. These latter studies suggest that the heparan sulfate accumulating in the tissue concurrent with the AA amyloid protein involves deposition of both the protein core and GAG chains and is likely in the form of a HSPG proteoglycan.

The presence of highly sulfated GAGs in amyloidotic tissue, the close temporal relationship between initial amyloid deposition and PG accumulation in experimental AA amyloidosis, and the intimate ultrastructural association between AA amyloid fibrils and heparan sulfate proteoglycans, all imply that PGs may play a role in the pathogenesis of AA amyloidosis and that this role may be common to all types of amyloid. If this were true, then we would expect highly sulfated GAGs and/or PGs to be present in all types of amyloid regardless of protein type. Studies involving histochemical staining techniques employing the Alcian blue-magnesium chloride staining technique, as well as biochemical analysis, and immunocytochemical studies were used to test this hypothesis. The types of amyloid analyzed are shown in Table 1B. The results demonstrated that sulfated GAGs and/or PGs are present in close association with all these amyloids regardless of the nature of the amyloid protein deposited, the tissue or organ involved, or the extent of deposition.

Preliminary analysis involving immunohistochemical techniques using a variety of antibodies to different PG and GAG epitopes suggests that heparan sulfate proteoglycans are present in human AA and AL amyloid deposits in a number of different organs within the same individual (Snow, Benditt, Kimata, Kato, Hassell and Wight, unpublished data) suggesting that this particular highly sulfated proteoglycan may be involved in amyloid deposition independent of the nature of the amyloid protein involved and the type of organ or tissue in which the deposition occurs. Possible role(s) of proteoglycans in the pathogenesis of amyloidosis One possible general role that the highly anionic PGs such as heparan sulfate may play in amyloidosis, is to influence different amyloidogenic proteins to form similar beta-pleated sheet structures and demonstrate similar morphological (i.e. fibrillar structure), staining (Congo red and Thioflavin S positive) and spectral characteristics. The ability of PGs/GAGs to influence amyloid fibril formation can be analogous to its role in collagen fibrillogenesis where the presence of PGs/GAGs in the early stages of collagen fibril formation determined the rate and the size of the fibril formed (Gelman and Blackwell, 1974a; 1974b; 1974c). Further studies are needed to determine which GAGs and/or PGs (if any) influence the conformation of other amyloidogenic proteins such as the beta-amyloid precursor in Alzheimer's disease, the PrP protein in the prion diseases, or the immunoglobulin light chains in AL amyloid.

Although it is feasible that highly sulfated PGs may play a role in the conformational folding of precursor amyloidogenic proteins into amyloid fibrils, many investigators would argue that PGs have nothing to do with amyloid fibril formation. This is due to the fact that a number of studies have shown that intact amyloid proteins (i.e. beta2-microglobulin) and/or synthetic peptides to portions of amyloid proteins (i.e. A4) can adopt a beta-pleated sheet conformation and polymerize as fibrils in vitro (Conners et al., 1985; Glenner et al., 1971). These studies include the formation of amyloid-like fibrils in vitro from immunoglobulin light chains (AL amyloid) (Glenner et al., 1971), $beta_2$-microglobulin (Conners et al., 1985) and synthetic peptides corresponding to portions of the A4 amyloid protein (Castano et al., 1986; Gorevic et al., 1987; Kirschner et al., 1987). However, diverse conditions and treatments appeared necessary for amyloid fibril formation to occur, including a progressive decrease in salt concentration for $beta_2$-microglobulin (Conners et al., 1985) and enzymatic digestion in an acidic environment for light chains of immunoglobulins (Glenner et al., 1971). In addition, in some instances, properties of the formed synthetic amyloid fibrils were somewhat different that those found in vivo. For example, the synthetic amyloid fibrils formed from synthetic peptides to various regions of the A4 protein could be completely solubilized whereas isolated amyloid fibrils from brain tissue is known to be very insoluble and tends to aggregate. Further studies are needed to determine whether the type of self-aggregation which can occur in vitro under a number of different conditions with various amyloidogenic proteins and synthetic analogues is actually the mechanism operating in vivo at the sites of amyloid formation.

A second possible role of highly sulfated proteoglycans in amyloidosis may be in determining the anatomical location of amyloid deposition. During the experimental induction of amyloid (i.e. AA amyloidosis, amyloid plaque formation in the scrapie hamster model), it is not known why the deposition of amyloid always occurs in precise anatomical sites (i.e. perifollicular area of spleen and in walls of central veins in liver; subependymal localization in scrapie hamster model). Likewise, clinically, certain types of amyloid are always found in specific organs or locales as opposed to other types of amyloid. Examples include senile cardiac amyloid in the heart, amyloid plaques in the hippocampal region in Alzheimer's disease and amyloid confined to the peripheral and autonomic nervous system in familial amyloidotic polyneuropathy. If highly sulfated PGs and/or GAGs are important in determining the location of amyloid deposits then it is possible that the PGs and/or GAGs are present in tissue locations prior to the deposition of amyloid to these sites. Although it is difficult to determine whether the association of PGs/GAGs to areas of amyloid deposits occurs as a primary or secondary event, evidence to suggest that they are deposited early during amyloid formation comes from a number of studies. In experimental AA amyloidosis, time course studies have demonstrated that highly sulfated GAGs (now identified as HSPGs) and the AA amyloid protein are deposited at virtually the same time and in the same locale (Snow and Kisilevsky, 1985; Snow et al., 1991). In Alzheimer's disease, immunocytochemical studies have demonstrated that HSPGs are present in "primitive plaques" (Snow et al., 1988). These plaques, containing essentially no amyloid component, are believed to be the precursor form of the mature plaque which contains an abundance of amyloid localized to a central core. Time-sequence analysis of initial β/A4 and HSPG deposition in different aged patient's with Down's syndrome indicate that HSPG accumulation in association with β/A4 may occur prior to the formation of fibrillar amyloid (Snow et al., 1990a), suggesting an important early role for HSPGs in the pathogenesis of β/A4 formation and/or deposition.

Another possibility that may be important in determining the location of amyloid deposits is that PGs have a strong binding affinity with possible amyloidogenic precursor proteins and/or the amyloid proteins themselves. As previously discussed, HSPGs appear to have a strong binding affinity for both the AA amyloid protein and the β/A4 amyloid protein (Snow et al., 1989) which may be important in the ultimate deposition of these amyloidogenic proteins to specific sites containing increased amounts of HSPGs. The preferential binding of PGs to specific proteins is not a new concept. For example, it has been known for some time that particular PGs interact with the protein moiety of beta-lipoproteins (Camejo, 1982).

A third possible role of highly sulfated PGs in the pathogenesis of amyloidosis, regardless of whether the accumulation of PGs in amyloid deposits occurs as a primary or secondary event, may involve PGs contributing to the insolubility of amyloid and its inaccessibility to proteolytic degradation in tissues. Amyloid deposits once established in various organs and tissues are very stable and usually stay in these sites over long periods of time without significant change (Franklin, 1972; Glenner and Page, 1976). Both experimentally and clinically, few methods have been successful for the removal of amyloid deposits once formed. In this same context, the association of PGs and/or GAGs with the amyloid protein in the neuritic plaques and the components of neurofibrillary tangles in Alzheimer's disease may contribute to the insolubility problems investigators have had in trying to isolate and sequence amyloid proteins (Gorevic et al., 1986; Iqbal et al., 1984). The presence of PGs at the sites of amyloid deposition may also be involved by interacting with proteases and/or protease inhibitors (i.e. alphal-antichymotrypsin) (Abraham et al., 1988) which may lead to the prevention of amyloid degradation once formed. An analogous situation has been recently reported (Saksela et al., 1988) in which endothelial cell-derived heparan sulfate was found to protect basic fibroblast growth factor from proteolytic degradation.

It is interesting to speculate that in Alzheimer's disease specific alterations in PG metabolism (i.e. synthesis and/or degradation) may occur in the brains of patients afflicted with this disease. It is even possible that the primary defect in Alzheimer's disease may actually be a defect directly or indirectly affecting PG metabolism which is only apparent in some individuals with aging and/or the presence of an unknown environmental stimulus. This PG defect could be residing in a subpopulation of cells and may contribute to the accumulation of PGs only within specific areas of the brain (i.e. in pyramidal neurons in the hippocampus). This may help explain the "selective vulnerability" of neurons that are affected in Alzheimer's disease. It is important to note that changes in the sulfation and/or polymerization of neuronal GAGs may occur in the brain as a function of aging. This may be necessary for the formation and/or accumulation of plaques and/or tangles that are observed even in aged non-demented individuals.

Alzheimer's Disease, amyloid precursor proteins and the β/A4 peptide.

The characteristic and diagnostic feature of brains of individuals with AD is the deposition and accumulation of a 39–43 amino acid peptide ($M_r$~4,200) termed the beta-amyloid protein (Glenner and Wong, 1984; Wong et al., 1985), A4 (Masters et al., 1985) or β/A4 (Beyreuther and Masters, 1990). This small peptide is a major component within the amyloid deposits of neuritic plaques and in the walls of blood vessels (i.e. congophilic angiopathy) in the brains of patients with AD, and is derived from larger precursor molecules (termed beta-amyloid precursor protein or APP) by an unknown pathogenic mechanism. APP is composed of 3 major isoforms, APP695, $APP_{751}$, and $APP_{770}$, which arise by alternative splicing of a single gene (Kang et al., 1987; Kitaguchi et al., 1988; Ponte et al., 1988). $APP_{751}$ and $APP_{770}$ contain a protease inhibitor domain (Ponte et al., 1988; Kitaguchi et al., 1988). The normal function of the APP is not known but some have speculated that it may play a role in neuronal adhesion (Kang et al., 1987), and/or neuronal growth and regulation (Whitson et al., 1989; Saitoh et al., 1989). APP contains an extracellular amino-terminal domain, a single transmembrane domain, and a short cytoplasmic segment. The sequence of β/A4 includes the first 28 residues of the extracellular domain and 11–14 residues of the proposed transmembrane domain. Recent studies (Sisodia et al., 1990; Esch et al., 1990) indicate that during normal APP catabolism the intact amyloidogenic fragment containing the β/A4 is not generated, due to proteolytic cleavage at or near position 612 of APP (Lys-16 of β/A4), resulting in the release of a soluble secreted protein of undefined function. These latter studies also suggest that altered APP processing is required to release the β/A4 domain found as a major component of fibrillar amyloid deposits.

Proteoglycans and Glycosaminoglycans

Proteoglycans are a group of complex macromolecules which are found in all organs and tissues, intracellularly in a variety of different cell types, or extracellularly in the matrix where they are exported for a variety of functions (Gallagher et al., 1986; Hascall and Hascall, 1981; Poole, 1986; Ruoslahti, 1988). Proteoglycans consist of a protein core to which one or more GAG chains are covalently linked through o-glycosidic linkage to serine residues in the core protein (Hascall and Hascall, 1981; Hassell et al., 1986). The highly anionic GAG chains consist of repeating disaccharide units, containing 1) hexosamine (either D-glucosamine or D-galactosamine) and 2) hexuronic acid (either D-glucuronic acid or L-iduronic acid) (Muir, 1969). Specific disaccharide repeat patterns give rise to 7 different types of GAGs. These are hyaluronic acid, chondroitin-4-sulfate, chondroitin-6-sulfate, dermatan sulfate, heparan sulfate, heparin and keratan sulfate. Usually one type of GAG predominates on a single core protein, giving rise to four major families including chondroitin sulfate proteoglycan (CSPG), dermatan sulfate proteoglycan (DSPG), heparan sulfate proteoglycan (HSPG) and keratan sulfate proteoglycan (KSPG). However, more than one type of GAG can be inserted on the same core protein giving rise to "hybrid PGs". The core proteins of the PGs have been the least well studied. However, a number of cDNAs have been cloned and the partial or complete amino acid sequence of some of these have been deduced (Bourdon et al., 1985; Day et al., 1987; Doegle, 1986; 1987; Krusius et al., 1987) including the complete amino acid sequence for the BM-HSPG (known as "perlecan") in both mouse (Noonan et al., 1988; 1991) and human (Kallunki and Tryggvason, 1992; Murdoch et al., 1992).

The diversity of PGs largely derives from the number of different protein cores within each PG family and from the polydiversity produced by a number of post translational modifications required to construct the final molecules. This structural diversity may account for the multiple properties of these complex molecules.

Specific Proteoglycans in Amyloidogenesis

Specific PGs such as the HSPG, together with the amyloid P component (Coria et al., 1988; Holck et al., 1979) are the only macromolecules consistently associated with all varieties of amyloid irrespective of the type of amyloid protein present or its location (Snow and Wight, 1989b). It is likely that some components involved in amyloid formation, deposition and accumulation are not unique to only one type of amyloidosis (i.e. the β/A4 of AD), but play a role in the pathogenesis of other types of amyloid as well (i.e. AA or inflammation-associated amyloid, AL amyloid involving the deposition of immunoglobulin light chains; transthyretin in familial amyloidotic polyneuropathy). A common mechanism may help explain why different types of amyloid (i.e. consisting of different amyloid proteins) all form similar beta-pleated sheet structures with similar morphological (i.e. fibrillar structure), staining (Congo red and Thioflavin S positive), and spectral characteristics.

One general role that the highly anionic PGs may play in amyloidosis is to influence different amyloidogenic proteins to form similar beta-pleated sheet structures. The ability of PGs and GAGs to influence amyloid fibril formation might be analogous to their role in collagen fibrillogenesis where the presence of PGs and GAGs determines the rate and the size of the fibril formed (Katz et al., 1986; Mathews and Decker, 1968; Obrink, 1973; Vogel et al., 1984). Evidence that highly sulfated GAGs can influence protein folding comes from in vitro circular dichroism studies which demonstrated that different GAGs can exert a direct influence on the conformational folding of various mixed and homologous polypeptides (Gelmann and Blackwell, 1973; 1974). Recent studies (McCubbin et al., 1988) demonstrate that heparan sulfate (and not heparin or chondroitin-6-sulfate) influences the specific AA amyloid precursor, known as $SAA_2$ to form a predominant beta-pleated sheet structure. This study implicates heparan sulfate in conformational alterations of amyloidogenic precursors which may be important in the ultimate formation of the beta-pleated sheet structure characteristic of all amyloids.

The distribution of particular proteoglycans may also specifically direct the anatomical location of amyloid deposition. If so, then PGs and/or GAGs may be present in tissue locations prior to the deposition of fibrillar amyloid at these sites. Although it is difficult to establish definitively whether the association of PGs/GAGs with amyloid deposits occurs as a primary or secondary event, evidence to suggest that PGs/GAGs are deposited early or concurrent with amyloid formation comes from a number of studies (Snow et al., 1988b; Snow et al., 1990). For example, in experimental AA amyloidosis, time course studies have demonstrated that HSPGs and the AA amyloid protein are deposited at virtually the same time and in the same locale (Snow and Kisilevsky, 1985; Snow et al., 1988b).

Regardless of whether the accumulation of PGs in amyloid deposits occurs as a primary or secondary event, PGs may contribute to the stability of amyloid and its inaccessibility to removal or proteolytic degradation in tissues. The presence of PGs at the sites of amyloid deposition may inactivate proteases and/or activate protease inhibitors (i.e. alpha 1-antichymotrypsin) (Abraham et al., 1988), which may prevent amyloid degradation. Recent studies have demonstrated that endothelial cell-derived heparan sulfate protects basic fibroblast growth factor from proteolytic degradation (Saksela et al., 1988). It is postulated that the basement membrane derived HSPG once bound to β/A4 prevents its normal degradation by proteases.

Heparan sulfate proteoglycans and their potential role in β/A4 amyloidogenesis

Although there are potentially many different types of PGs and/or GAGs that can be synthesized by cells, both within and outside the CNS, accumulating evidence suggests that only the HSPG class is localized to a variety of different amyloids (Snow et al., 1988a; 1988b; 1989). The specific association of HSPGs with a variety of different amyloids suggests that the HSPG-amyloid association is more than simply a charge effect since similarly charged PGs such as keratan sulfate do not appear to be present in association with different amyloid proteins (Snow and Wight, 1989). Immunocytochemical evidence indicates that it is the basement membrane derived HSPG (i.e. perlecan) which is associated with a variety of different amyloids (Snow et al., 1988a; 1988b; Snow and Wight, 1989). The deduced amino acid sequence of the core protein of this particular PG is known from the analysis of corresponding cDNA sequences in both mouse (Noonan et al., 1988; 1991) and human (Kallunki and Tryggvason, 1992; Murdoch et al., 1992), and the gene for this HSPG is localized to chromosome 1 in both of these species (Wintle et al., 1990).

As described above, recent studies (Esch et al., 1990; Sisodia et al., 1990) imply that other amyloid components may be necessary and involved in post-translational modifications of the APP, ultimately leading to the accumulation of the β/A4 fragment. One such component may be the basement membrane derived HSPG. Our previous studies have shown the accumulation and co-localization of a specific HSPG to the amyloid deposits containing β/A4 in neuritic plaques and amyloidotic blood vessels in AD and Down's syndrome brain (Snow et al., 1988a; 1989; 1990). Immunohistochemical (Snow et al., 1988; Snow and Wight, 1989) and cationic dye studies (Snow et al., 1989; Young et al., 1989) indicate an intimate ultrastructural association between this particular PG and amyloid fibrils containing the β/A4.

In Down's syndrome, evaluation of brains from patients aged 1 day to 51 years demonstrated initial co-accumulation of both HSPG and β/A4 in diffuse cortical deposits in 18 and 24 year old patients. These deposits were congo red and thioflavin S negative and were believed to be the precursor to fibrillar amyloid formation which was observed in Down's syndrome patients over the age of 35 years (Snow et al., 1990). This observation rules against the possibility that PGs accumulate in amyloid simply as a common response to the presence of amyloid fibrillar deposits.

Potential Animal Models of Alzheimer's Disease

Early animal models of AD focused upon the neurochemical and anatomic pathology of the disease and attempted to mimic this pathology with lesions in animals. One of the first models focused on the cortical cholinergic system which is profoundly affected in AD (Perry et al., 1977; Davies and Maloney, 1978). Whitehouse et al. (1982) reported that the cells of origin of the cortical cholinergic fibers, located in the nucleus basalis, were substantially depleted in AD. This led to a large number of studies examining the effects of nucleus basalis lesions in rats and other species on behavioral and neurochemical indices. These lesions were widely reported to induce memory deficits for a number of tasks (Flicker et al., 1983; Helper et al., 1985; Kesner et al., 1986). Some normally aged rats have spontaneous loss of nucleus basalis cholinergic neurons, and this loss is correlated with memory dysfunction (Bartus et al., 1982). Fisher et al. (1987) found that intraventricular nerve growth factor infusions could reverse the cholinergic neuron atrophy and restore memory function in these aged rats. This finding, among others, has led to the suggestions that nerve growth factor (NGF) may be therapeutically beneficial in AD (Hefli et al., 1989). Arendash et al. (1987) reported that the long term effects (14 months postlesion) of nucleus basalis lesions caused the formation of plaque-like and fibrillar structures in rat brain, and resulted in neuron loss in cortex, hippocampus and amygdala. Surprisingly, additional reports characterizing this model of AD have not appeared over the last 5 years.

In spite of the Andendash et al. (1987) report, most view the cholinergic deficits as a critical component, but not the major dysfunction in AD. Some researchers have raised doubts about the role of basal forebrain cholinergic neurons in memory dysfunction (Wenk et al., 1986). Others suggest that the nucleus basalis neuron atrophy in AD may be secondary to cortical degeneration, because cortical lesions in rats and monkeys can lead to shrinkage of these cells (Sofroniew et al., 1983; Pearson et al., 1983). A second lesion model receiving some attention is lesions in entorhinal cortex. Hyman et al. (1984) recognized that loss of projection neurons from the entorhinal cortex to the hippocampus was a prominent feature in AD, which, together, with the subicular neuron loss, functionally isolated the hippocampus from the rest of the brain. Entorhinal lesions in rats have long been studied as a model system for synaptic sprouting within the denervated hippocampus. Geddes et al. (1986) have reported remarkable similarities in the hippocampus between neurochemical and anatomical changes in AD and those following entorhinal lesions in rats, and suggest that reactive synaptogenesis may play a critical role in amyloid plaque formation. However, one problem with most lesion models of AD is that they ultimately may mimic some of the end stage pathology of the disease, and not the pathogenesis of the disease.

Another potential animal model of AD is normal aging. Several species develop β/A4 immunoreactive amyloid plaques including dogs (Ishihara et al., 1991), non-human primates (Selkoe et al., 1987; Martin et al., 1991), and polar bears (Cork et al., 1988). One problem with these models is that the amyloid plaques usually occur in late life in these animals, precluding rapid screening of potentially therapeutic substances or interventions. One advantage of the rat model described in this patent application is the rapid production (within 1 week) of β/A4 amyloid deposits in brain. Interestingly, Vaughan and Peters (1981) reported that aged Sprague-Dawley rats (28 and 30 months old) possess congophilic amyloid plaques that ultrastructurally resemble the material found in AD. Surprisingly, these data have not been widely discussed in other reports.

More recently, transgenic mice have been produced as potential models of AD. The rationale for these models is that overproduction of an APP transgene (containing all or part of the APP sequence) could lead to the eventual development of β/A4 deposits in mouse brain and subsequent plaque formation. Wirak et al. (1991) generated transgenic mouse lines containing the β/A4 sequence under the control of the human APP promoter. After 1 year, these mice developed β/A4 deposits within hippocampal neurons and formed aggregates of amyloid-like fibrils. Quon et al. (1991) used a full length $APP_{751}$ (Kunitz protease inhibitor containing form) sequence linked to a neuron-specific enolase promoter. Transgenic mice with this construct displayed extracellular β/A4 immunoreactive deposits, which were infrequently stained with thioflavin S, but not by congo red, suggesting a pre-amyloid like composition. Kawabata et al. (1991) developed transgenic mouse lines massively overexpressing a construct encoding the C-terminal 100 amino acids of APP under control of a Thy-1 element. These mice displayed pathology remarkably similar to that observed in AD including amyloid plaques, neurofibrillary tangles and neurodegeneration in hippocampus, neocortex and even cerebellum. While extremely promising, the report by Kawabata et al. (1991) has been retracted whereas the study by Wirak et al. (1991) has been questioned (Jucker et al., 1992). Additional research will determine if the overexpression of APP is sufficient to produce the neuropathological features of AD. While more rapid than aged animal models, these models still suffer from the requirement of several months delay before AD-like pathology may develop.

The last type of animal models all involve injecting or transplanting materials into brain parenchyma. Richards et al. (1991) grafted fetal hippocampus from trisomy 16 mice into congenic normal mice and observed intracellular staining for APP, β/A4, neurofibrillary tangles, tau protein and ubiquitin immunoreactivity, within the graft, but not in host tissues. However, no extracellular β/A4 deposits resembling amyloid plaques were reported. Trisomy 16 mice contain an additional APP gene, analogous to Down's syndrome patients (human trisomy 21), who develop amyloid plaque and neurofibrillary tangle pathology similar to that observed in AD. A second model using parenchymal injections was described by Kowall et al. (1991). These authors acutely injected β/A4 (1–40) into rat hippocampus and observed substantial neuronal loss and induction of ALZ-50 antibody immunostaining within 1 week. These effects were attenuated by coadministration of substance P either centrally or peripherally. Importantly, no apparent congophilic amyloid deposits was observed. A final animal model involved acute injections of purified AD amyloid plaque cores into rat cortex or hippocampus (Frautschy et al., 1991). At 1 month, but not 1 week, ALZ-50 and ubiquitin staining and neuronal degeneration was evident in 70% of the rats. As expected, these amyloid cores isolated from AD brain remained congophilic after residing in rat brain for 1 month. It is important to note that SDS-extracted amyloid cores from human AD brain still contain immunoreactivity for HSPGs suggesting that in this latter study, besides undefined components in the isolated plaque cores, HSPGs and β/A4 were present.

Each of the animal models described above possess specific features making them valuable for AD research. However, each has some disadvantages. The specific advantages of our model include 1) the deposition of congophilic β/A4 amyloid in rat brain at selected sites, 2) the model is rapid with some features present as early as 1 week (although neurodegenerative effects may require longer incubations as in Frautschy et al. (1991)), 3) the injected materials consists of defined components enabling one to determine the effects of each component individually (by infusing them separately or in different concentration ratios), and 4) by continuous infusion we are able to deposit into brain larger quantities of material than by acute injections.

SUMMARY OF THE INVENTION

Excessive congophilic and fibrillar amyloid deposition, containing a 39–42 amino acid peptide termed β/A4, is a characteristic and diagnostic feature observed in brains of patients with Alzheimer's disease (AD). A rapid animal model of β/A4 amyloid deposition in rat hippocampus is described after assessing continuous infusion of β/A4 (1–40) in the presence or absence of specific proteoglycans/glycosaminoglycans. 100% of animals (6 of 6) receiving infusions for 1 week of synthetic β/A4 (1–40) (SEQ ID. NO 1) plus mouse perlecan, a basement membrane-derived heparan sulfate proteoglycan (HSPG), demonstrated congo red and thioflavin S deposits indicative of amyloid adjacent to the infusion site. Similar results (100%, 4 of 4) were obtained in animals infused for 2 weeks (and sacrificed 5 weeks later) with β/A4 (1–40) plus mouse perlecan. Extracellular amyloid fibrils with a diameter of 10–12 nm were identified by electron microscopy and were specifically immunogold decorated with β/A4 antibody. β/A4 amyloid deposition also occurred in 4 of 6 animals infused with β/A4 (1–40) only when endogenous brain HSPG accumulated at the β/A4 infusion site.

Other new potential animal models of AA amyloidosis, AL amyloidosis, Prealbumin/Transthyretin amyloidosis, Beta$_2$-microglobulin amyloidosis, Endocrine type amyloidosis, and PrP protein amyloidosis are presented involving injections and/or infusions of the various amyloid proteins in combination with perlecan or derivatives thereof The disclosed animal models serve as in vivo screens for potential therapeutic intervention or agents in each of the different amloidoses.

In vitro studies demonstrate a particular high binding affinity between the high $M_r$ basement membrane derived HSPG and β/A4 (1–28) (SEQ ID. NO: 2) which could be competitively inhibited by highly sulfated GAGs such as heparin, heparan sulfate and related macromolecules (e.g., dextran sulfate). These in vitro studies indicate that highly sulfated GAGs are candidate agents for therapeutic intervention. This was confirmed by in vivo studies demonstrating that co-infusion of HS glycosaminoglycans with β/A4 inhibited congophilic and fibrillar amyloid deposition and/or its persistence in brain. Additionally, since sequence analysis suggests that a putative heparin binding domain resides at residues 12–17 of β/A4 (Cardin and Weintraub, 1989), a potential inhibitor of HSPG-β/A4 binding and/or β/A4 amyloid deposition in brain consists essentially of a small 6 amino acid peptide having the sequence of -valine-histidinehistidine-glutamine-lysine-leucine-(SEQ. ID. NO. 3).

The disclosed animal models will aid investigators in further determining the in vivo effects of β/A4 amyloid on endogenous brain components, serve as rapid in vivo screens for candidate therapeutic interventions or agents, and further implicate highly sulfated macromolecules such as heparin, heparan sulfate, and related analogues, and a 6 amino acid peptide to the putative heparin binding domain of β/A4, as inhibitors of β/A4 amyloid deposition in brain and therefore as a potential therapeutic intervention for patients with AD and/or other amyloidoses.

DESCRIPTION OF THE DRAWINGS

The file of this patent contains at least one drawing executed in color. Copies of this patent with color drawing (s) will be provided by the Patent and Trademark Office upon request and payment of the necessary fee.

Figure 1I:
FIG. 1: A Rat Model of β/A4 Amyloid Deposition in Brain and the Critical Role of Heparan Sulfate Proteoglycans.
Figure 1H:
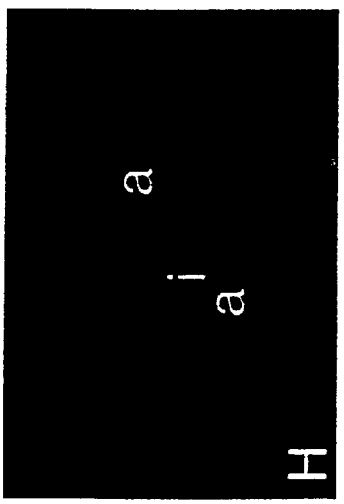

Photomicrographs were taken from animals continuously infused for 1 week with β/A4 (1–40) & HSPG (FIGS. A–D, F–G); HS GAGs only (FIG. E); β/A4 (1–40) only (FIGS. H–J); and β/A4 & HS GAGs (FIGS. K–L). In some FIGS. (C–E; G–H; K–L) the infusion site is marked "i", whereas the pyramidal layer of the hippocampus is shown by the open arrow (FIGS. B–E and G). FIGS. C–G and I–L represent use of the avidin-biotin-peroxidase method with hematoxylin counterstain.

- A: Amyloid deposition adjacent to infusion site (i) in animal infused with β/A4 & HSPG as demonstrated by positive congo red staining (arrows; red/green birefringence) as viewed under polarized light. This same area was also thioflavin S and β/A4 positive on adjacent sections.
- B: Positive thioflavin S fluorescence in exact locales of β/A4 (FIG. 1C) and HSPG (FIG. 1G) immunoreactivity, again indicating the presence of amyloid.
- C: Serial section of FIG. 1B demonstrating β/A4 (1–40) (polyclonal; 1:200 dilution) immunostaining (arrow) at amyloid deposition site.
- D: Low magnification of β/A4 (1–40) immunostaining (arrow) demonstrating the extent of β/A4 infusion (solid arrow) into hippocampus. β/A4 (1–40) deposition is directly adjacent to the pyramidal layer of the hippocampus (open arrow). The infusion site (i) cavity is formed by the catheter within the brain tissue for 1 week, and was similarly observed in all infusion groups.
- E: Lack of β/A4 (1–40) immunostaining adjacent to infusion site (i) in animal infused with HS GAGs only.
- F: β/A4 (1–40) immunopositive diffuse deposits (arrows) in thalamus of animal infised with β/A4 & HSPG. These diffuse deposits were 2.5 mm from the center of the infusion site and were congo red negative. Immunostaining was abolished when the identical β/A4 antibody was used in the presence of excess β/A4 (1–40) peptide (not shown).
- G: HSPG deposition (solid arrow) at infusion site as demonstrated using a monoclonal antibody (HK-102; undiluted hybridoma supernatant) to the core protein of perlecan. Even though HSPG was co-infused with β/A4, in brain HSPG remains specifically localized to β/A4 immunopositive sites (compare to FIG. 1C).
- H: Thioflavin S fluorescence demonstrating amyloid (a) deposition adjacent to infusion site (i) following 1 week of continuous infusion of β/A4 (1–40) only. Thioflavin S positive site was also positive with congo red and immunostained with a polyclonal antibody to β/A4 (1–40).

I: High magnification of amyloid site (a) adjacent to infusion site (i) following 1 week of continuous infusion of β/A4 (1–40) only. Positive immunostaining is observed with a polyclonal antibody (1:500 dilution) to HSPG core protein suggesting that endogenous HSPG accumulates at β/A4 amyloid site within 1 week of infusion.

J: Serial section of amyloid site (a) (from FIG. 1I) immunostained with the identical HSPG core protein polyclonal antibody in the presence of excess HSPG antigen, further demonstrating the specificity of the HSPG antibody used.

K: β/A4 (1–40) immunostaining (arrows) adjacent to infusion site following 1 week of continuous infusion of β/A4 (1–40) and HS GAGs. Serial section immunostained with an HS GAG monoclonal antibody (HK-249) shows HS GAG deposition in exact locales as β/A4 (1–40) (not shown).

L: Adjacent section (from FIG. 1K) demonstrating negative congo red staining (as viewed under polarized light) in β/A4 and HS GAG immunopositive areas. The inclusion of HS GAGs in conjunction with β/A4 (1–40) appeared to markedly diminish positive congo red and thioflavin S staining (see Table 1). Bars, μm.

FIG. 2: Electron Microscopic Confirmation of β/A4 Amyloid Fibril Deposition Within 1 Week of Continuous Infusion of β/A4 (1–40) and Heparan Sulfate Proteoglycan.

A: Area of extracellular amyloid fibril (a) deposition adjacent to infusion site 1 week following continuous infusion of β/A4 (1–40) and HSPG. In addition to fibrillar amyloid deposition occurring between microglia/macrophages (m), amorphous material (arrowheads) was also found and immunogold labeled with an antibody to β/A4 (1–40) (not shown) indicating the presence of β/A4 in a non-fibrillar form. Original Mag. X4,000.

B: Area of extracellular amyloid fibril (a) deposition adjacent to infusion site 1 week following continuous infusion of β/A4 (1–40) and HSPG. A prominent array of amyloid fibrils are observed. Measurement of amyloid fibrils at high magnification indicate fibrils on average have a diameter of 10–12 nm, very similar in appearance and dimensions to β/A4 amyloid fibrils in human AD brain. Original Mag. X10,000.

C: Immunogold labelling of extracellular amyloid fibrils with a polyclonal antibody (1:500 dilution) to β/A4 (1–40). Original Mag. X75,000.

D: Lack of immunogold labelling of extracellular amyloid fibrils using Tris-buffered saline instead of the primary β/A4 (1–40) polyclonal antibody. Similar observations were observed when the same antibody was used in the presence of excess β/A4 (1–40) peptide. Original Mag. X75,000.

FIG. 3: Effects of β/A4 Amyloid Deposition on Endogenous Brain Components.

Figure 3C:
Figure 3F:
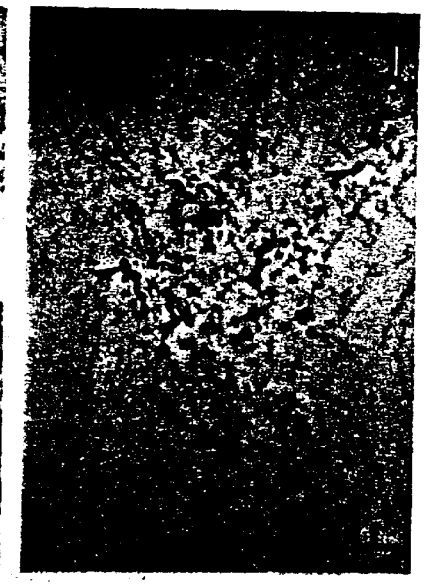
Figure 3B:
Figure 3E:

FIGS. 3A–E represent use of the avidin-biotin-peroxidase method with hematoxylin counterstain, whereas FIG. 3F represents use of the alkaline-phosphatase method with hematoxylin counterstain.

A: Modified Bielchowsky silver staining of hippocampus in animal infused with β/A4 (1–40) & HSPG. Many silver positive structures (arrows) identified as neurons (by positive Nissl staining) were observed in cerebral neocortex 2 mm from the center of the infusion site. This staining pattern mimics NFTs and/or dystrophic neurites in AD brain.

B: Modified Bielchowsky silver staining of hippocampus from same animal shown in FIG. 3A. Silver staining of small vessels (arrows) suggests the presence of amyloid deposition in the vasculature.

C: Positive Alz-50 immunostaining (monoclonal; 1:200 dilution) in exact locale (solid arrow) of β/A4 amyloid deposition (compare to FIG. 1C).

D: Lack of Alz-50 immunostaining at infusion site in animal infused with HSPG only.

E: GFAP immunostaining (polyclonal; 1:10000 dilution) of astrocytes (arrowheads) adjacent to infusion site (i) in animal infused with β/A4 and HSPG. Increased GFAP immunostaining was primarily observed surrounding the infusion site but not within the β/A4 immunopositive areas (solid arrow).

F: ED1 immunostaining (monoclonal; 1:2500 dilution) demonstrating the presence of macrophages/microglia (arrowheads) in β/A4 immunopositive and amyloid deposition areas adjacent to infusion site (i) in animal.

FIG. 4: Binding of Beta-amyloid Peptide (Residues 1–28) to HSPGs in AA Amyloidotic Mouse Spleen.

CBA/J mice were injected with amyloid enhancing factor (AEF) plus silver nitrate to produce AA amyloid and HSPG accumulation in various systemic organs including spleen (Snow and Kisilevsky, 1985). All figures are of spleen tissue, 4 days after initial AEF plus silver nitrate treatment.

A: Demonstration of AA amyloid in the perifollicular area of the spleen (arrowheads) by positive immunostaining with a polyclonal antibody (1:10 dilution) to the AA amyloid protein. Bar=15 μm.

B: Demonstration of HSPGs in the exact locale (arrowheads) of AA amyloid accumulation using a monoclonal antibody (undiluted hybridoma supernatant) directed against the GAG chains of the high MW HSPG (Koike et al., 1987). Bar=15 μm.

C: Weak to no immunostaining is observed in the perifollicular area of the spleen using a polyclonal antibody (1:100 dilution) directed against residues 1–28 of the BAP. Bar=15 μm.

D: Pretreatment of the splenic tissue section overnight (at 4° C.) with a synthetic BAP peptide (residues 1–28, concentration of 0.3 mg/ml), produces positive immunostaining (arrowheads) using the BAP polyclonal antibody (1:100 dilution). Bar=15 μm.

E. Splenic tissue was treated with chondroitinase ABC (to remove chondroitin sulfate and/or dermatan sulfate GAG chains), prior to pretreatment (concentration of 0.3 mg/ml) overnight (at 4° C.) with a synthetic peptide to residues 1–28 of BAP, followed by BAP immunostaining (polyclonal antibody, 1:100 dilution). No decrease in immunostaining in the splenic perifollicular area (arrowheads) is observed. Bar=15 μm.

F. The adjacent serial section of FIG. 1E was treated with nitrous acid (to remove heparan sulfate GAG chains), prior to pretreatment (concentration of 0.3 mg/ml) overnight (at 4° C.) with a synthetic peptide to residues 1–28 of BAP, followed by BAP immunostaining with a polyclonal antibody. A decrease in immunostaining is observed in the perifollicular area of the spleen (compare to FIG. 1E). Bar=15 μm.

Figure 5A:
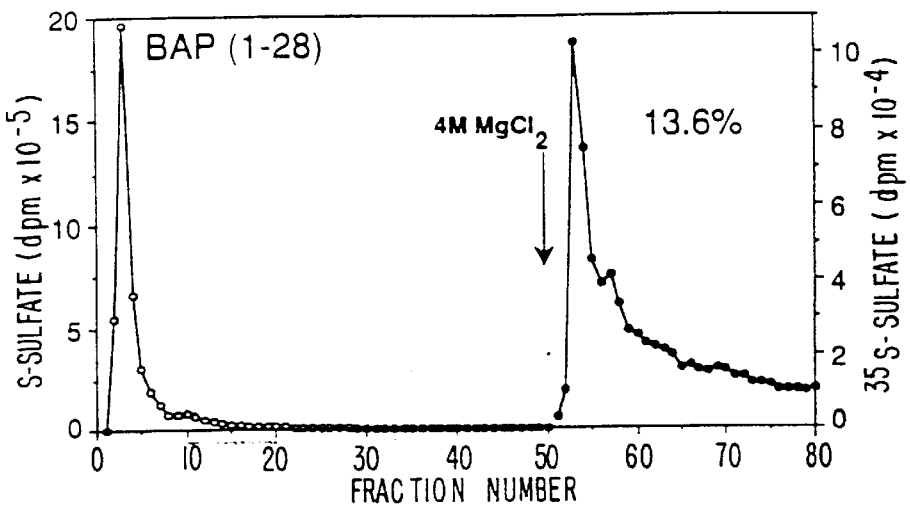
Figure 5B:
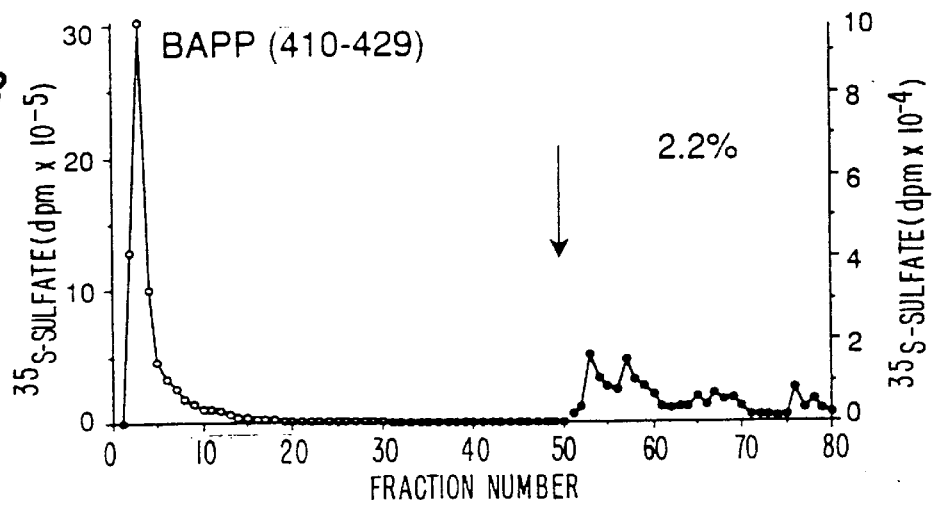
Figure 5C:
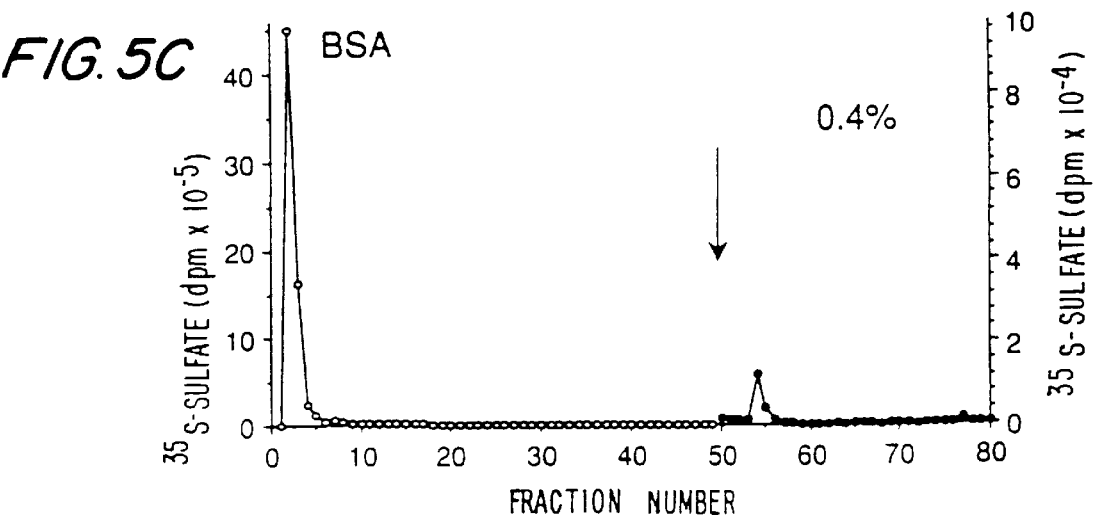

FIG. 5: Preferential Binding of Endothelial Cell Proteoglycans to an Affinity Column Containing the BAP (residues 1–28) of Alzheimer's Disease.

Approximately 500,000 dpm of $^{35}$S-sulfate labeled PGs isolated from the culture media of ECs were applied to Affi-gel 10 affinity columns containing approximately 0.45 mg of 1) residues 1–28 of BAP, 2) residues 410–429, a region of BAPP present in the extracellular domain, or 3) bovine serum albumin. The labeled PGs were left on the column for 1 hour, after which non-bound radiolabelled PGs were eluted with 25 ml (50 0.5 ml fractions) of TBS+0.1% TX-100 and collected on a fraction collector. Bound PGs were then eluted from the column with 15 mls of 4M MgCl$_2$ in TBS+0.1% TX-100. Recoveries were found to exceed 85% for each experiment. As shown, 13.6% of $^{35}$S-sulfate labeled PGs were bound to the column containing residues 1–28 of the BAP and subsequently removed with 4M MgCl$_2$ (top panel), whereas only 2.2% bound to the BAPP column (residues 410–429) (middle panel), and 0.4% bound to the affinity column containing BSA (bottom panel).

FIG. 6: Characterization of Beta-Amyloid Protein (1–28) Bound and Nonbound Endothelial Cell and Smooth Muscle Cell Proteoglycans.

$^{35}$S-sulfate labeled EC (FIG. 6A) or SMC (FIG. 6B) PGs that were bound or failed to bind to BAP (1–28) were run on SDS-PAGE (4–12% gradient gel) under reducing conditions and fluorographs were prepared. The gel-stacker interface is indicated by the arrow in each figure.

A:
  Lane 1: Non-Bound EC PGs
  Lane 2: Non-Bound EC PGs after chondroitin ABC lyase digestion. The majority of the broad band observed in lane 1 is degraded.
  Lane 3: EC PGs which bind to the BAP (1–28) contain three distinct bands.
  Lane 4: Bound EC PGs after chondroitin ABC lyase digestion. The two lower $M_r$ bands observed in lane 3 are degraded whereas the band just entering the gel in lane 3 is resistant.
  Lane 5: Molecular weight standards.

B:
  Lane 1: Non-bound SMC PGs
  Lane 2: Non-bound SMC PGs after chondroitin ABC lyase digestion. Removal of the major band in the stacking gel, as well as the two bands above and below the 200 kDa marker was achieved (compare to lane 1). A putative core protein (above the 200 kDa marker) believed to represent the large CSPG found in SMCs is observed.
  Lane 3: Bound SMC PGs consist of a band just entering the gel, and two broad bands above and below the 200 kDa marker. Note that no band is apparent in the stacking gel indicating that the high $M_r$ CSPG (observed in lane 1) did not bind BAP.
  Lane 4: Bound SMC PGs after chondroitin ABC lyase digestion. The two lower Mr bands observed in lane 3 are degraded whereas the band just entering the gel in lane 3 is resistant.
  Lane 5: Molecular weight standards.

Figure 7A:
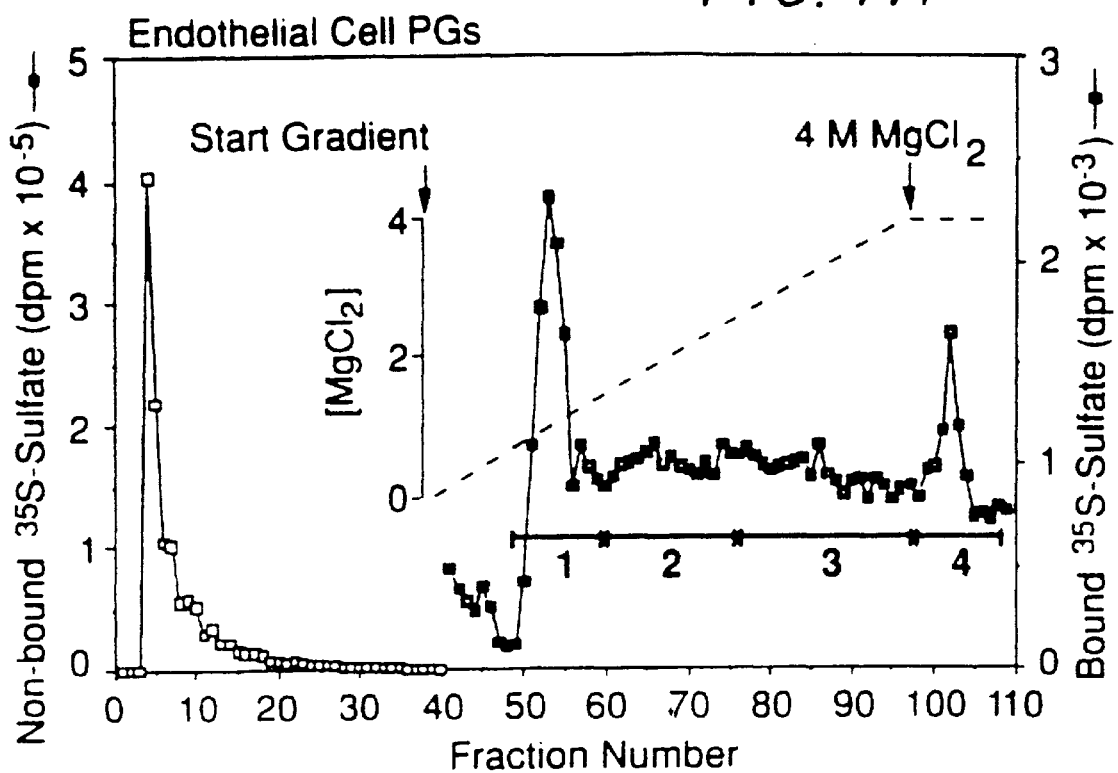

FIG. 7: Differential Affinity of Endothelial Cell and Smooth Muscle Cell Derived-Proteoglycans for Beta-Amyloid Protein (1–28).

A: $^{35}$S-sulfate labeled PGs isolated from the culture media of ECs were applied to an Affi-gel 10 column containing 0.90 mg of BAP (residues 1–28). After eluting non-bound PGs from the column with TBS+0.1% TX-100 (fractions 1–40), bound PGs were eluted from the column with a linear salt gradient of 0 to 4M MgCl$_2$ (fractions 41–110).

B: $^{35}$S-sulfate labeled PGs that were bound to BAP and eluted with a linear salt gradient (see FIG. 4A) were pooled according to increasing affinities (pooled fractions 1–4 in FIG. 4A), run on SDS-PAGE (4–12% gradient gel) under reducing conditions, and fluorographs were prepared. Approximately 20,000 dpm were loaded in each lane, except for lane 4 which had 14,000 dpm loaded.
  Lane 1: Pooled fraction 1 representing bound EC PGs eluted with <1M MgCl$_2$ (in TBS+0.1% TX-100). There is a band just entering the gel, and a band below the 200 kDa marker. Additionally, a faint band is apparent above the 200 kDa marker.
  Lane 2: Pooled fraction 2 representing bound EC PGs eluted with 1 to 2M MgCl$_2$ (in TBS+0.1% TX-100). The band just entering the gel is predominant.
  Lane 3: Pooled fraction 3 representing bound EC PGs eluted with 2 to 4M MgCl$_2$ (in TBS+0.1% TX-100). The band just entering is predominant.
  Lane 4: Pooled fraction 4 representing bound EC PGs eluted with 4M MgCl$_2$ (in TBS+0.1% TX-100). The band just entering the gel is predominant. Therefore, a relative increase in the proportion of the high Mr band just entering the gradient gel was observed with increasing concentrations of salt (lanes 1–4).

C: $^{35}$S-sulfate labeled PGs isolated from the culture media of SMCs were applied to an Affi-gel 10 column containing 0.90 mg of BAP (residues 1–28). After eluting non-bound PGs from the column with TBS+0.1% TX-100 (fractions 1–50), bound PGs were eluted from the column with a linear salt gradient of 0 to 4M MgCl$_2$ (fractions 50–110).

D: $^{35}$S-sulfate labeled PGs that were bound to BAP and eluted with a linear salt gradient were pooled according to increasing affinities (pooled fractions 1–4 in FIG. 4C), run on SDS-PAGE (4–12% gradient gel) under reducing conditions and fluorographs were prepared. Approximately 20,000 dpm were loaded in each lane, except for lane 4 which had 12,000 dpm loaded.
  Lane 1: Pooled fraction 1 representing bound SMC PGs eluted with <1M MgCl$_2$ (in TBS+0.1% TX-100). There is a band just entering the gel, a predominant band above the 200 kDa marker, and a faint band below the 200 kDa marker.
  Lane 2: Pooled fraction 2 representing bound SMC PGs eluted with 1 to 2M MgCl$_2$ (in TBS+0.1% TX-100). Similar bands are observed as in lane 1.
  Lane 3: Pooled fraction 3 representing bound SMC PGs eluted with 2 to 4M MgCl$_2$ (in TBS+0.1% TX-100). The band just entering the gel is predominant.
  Lane 4: Pooled fraction 4 representing bound SMC PGs eluted with 4M MgCl$_2$ (in TBS+0.1% TX-100). The band just entering the gel is predominant. Therefore, a relative increase in the proportion of the high $M_r$ band just entering the gradient gel was observed with increasing concentrations of salt (lanes 1–4).

FIG. 8: Binding of Isolated $^{35}$S-sulfate Labeled Dermatan Sulfate Proteoglycans to Beta-Amyloid Protein (1–28).

A: $^{35}$S-sulfate labeled DSPGs isolated from the culture media of ECs were applied to an Affi-gel 10 column containing 0.90 mg of BAP (1–28). After eluting non-bound PGs from the column with TBS+0.1% TX-100 (fractions 1–50), a linear salt gradient from 0 to 4M MgCl$_2$ (fractions 51–110) was run to elute bound PGs, followed by elution with 4M MgCl$_2$ (in TBS+0.1% TX-100) (fractions 110–130) and 8M urea +3M NaCl (fractions 130–150). As shown, most of the DSPGs bound to the BAP column weakly and were primarily eluted with low salt (<1M MgCl$_2$ in TBS+0.1% TX-100).

B: $^3$S-sulfate labeled DSPGs that were applied to the BAP column (in FIG. 5A) were run on SDS-PAGE (4–12% gradient gel) under reducing conditions and fluorographs were prepared. The arrow marks the stacking gel-gradient gel interface. The principal bands representing the two DSPGs are observed just above and below the 200 kDa marker (arrowheads).

FIG. 9: Binding of Isolated High Molecular Weight Heparan Sulfate Proteoglycans to Beta-Amyloid Protein (1–28).

A: $^{35}$S-sulfate labeled HSPGs isolated from the culture media of ECs were applied to an Affi-gel 10 column containing 0.90 mg of BAP (1–28). After eluting nonbound PGs from the column with TBS+0.1% TX-100 (fractions 1–50), a linear salt gradient from 0 to 4M MgCl$_2$ (fractions 51–110) was run to elute bound PGs from the column, followed by further elution with 4M MgCl$_2$ (in TBS+0.1% TX-100) (fractions 110–130) and 8M urea +3M NaCl (fractions 130–150. As shown, most of the isolated HSPGs bound to BAP tightly and were removed with 8M urea +3M NaCl.

B: $^{35}$S-sulfate labeled HSPGs that were applied to the BAP column (in FIG. 7A) were run on SDS-PAGE (4–12% gradient gel) under reducing conditions and fluorographs were prepared. The arrow marks the stacking gel-gradient gel interface. The principal band present just entering the gradient gel (lane 1, arrowhead), which is completely degraded with nitrous acid (lane 2), represents the high Mr HSPG.

Figure 10:
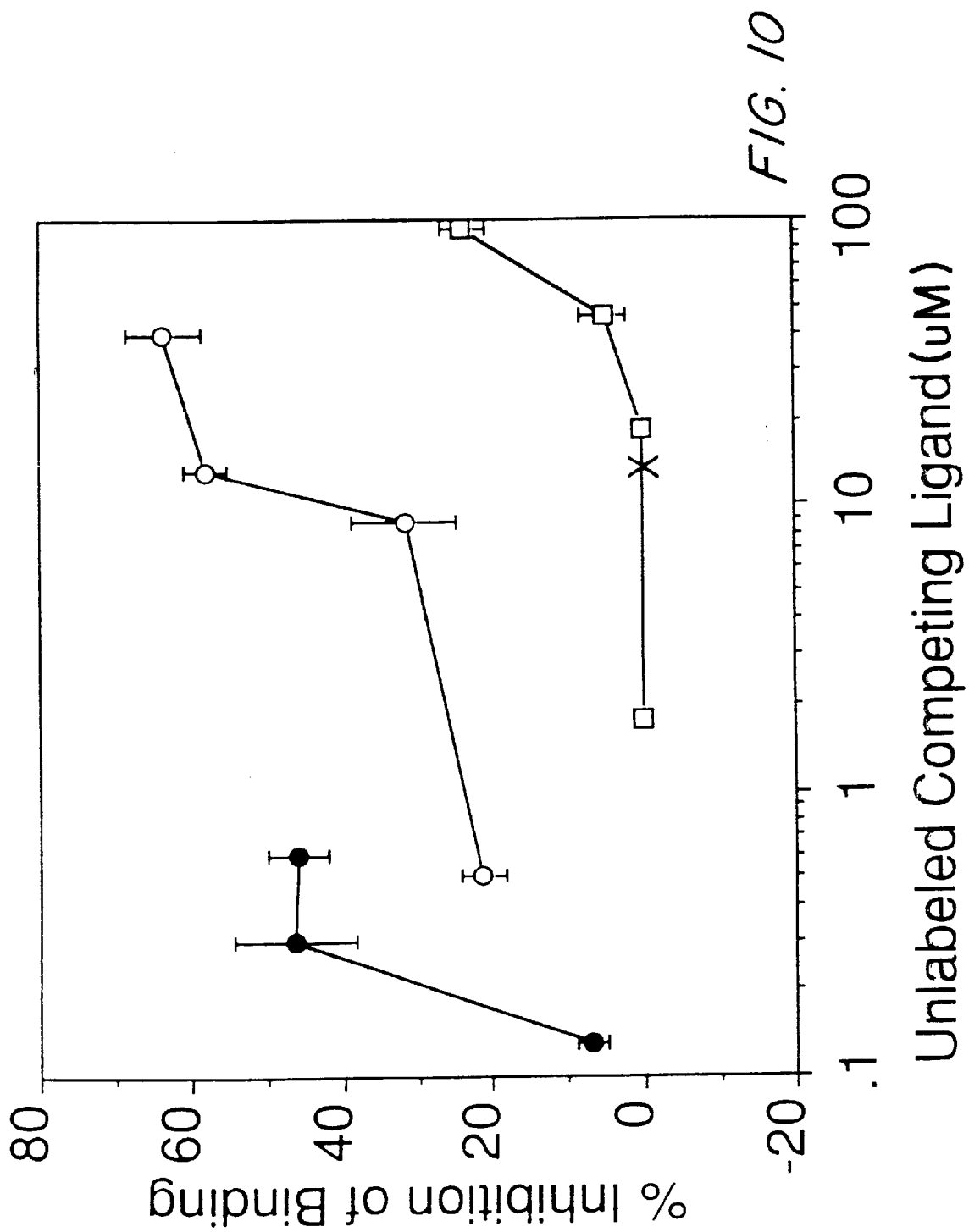

FIG. 10: Competitive Inhibition of $^{125}$I-labeled HSPG Binding to Beta-Amyloid Protein (1–28).

$^{125}$I-labeled HSPGs in the presence of increasing concentrations of unlabeled GAGs, or large low density HSPG (from EHS sarcoma) were applied to an Affi-gel 10 column containing BAP (residues 1–28). After nonbound PGs were eluted from the column using TBS+0.1% TX-100, bound PGs were eluted with a step gradient using 15 ml of 1M MgCl$_2$ in TBS+0.1% TX-100, followed by 15 ml of 4M MgCl$_2$ in TBS+0.1% TX-100, and then 10 ml of 8M urea buffer containing 3M NaCl. In the absence of unlabeled competing ligand, 21.6+/-4.4% (average of 5 separate runs) of applied $^{125}$I-labeled HSPG bound to the column. EHS HSPG (closed circles) was a more effective competitor with $^{125}$I-HSPG for binding to BAP than heparin (open circles). Chondroitin-6-sulfate (open squares) (at all concentrations except 100 uM) and unsulfated dextran sulfate (X) (at 12.3 uM) were unable to compete for binding to BAP. Bars indicate standard error of the mean.

Figure 11:
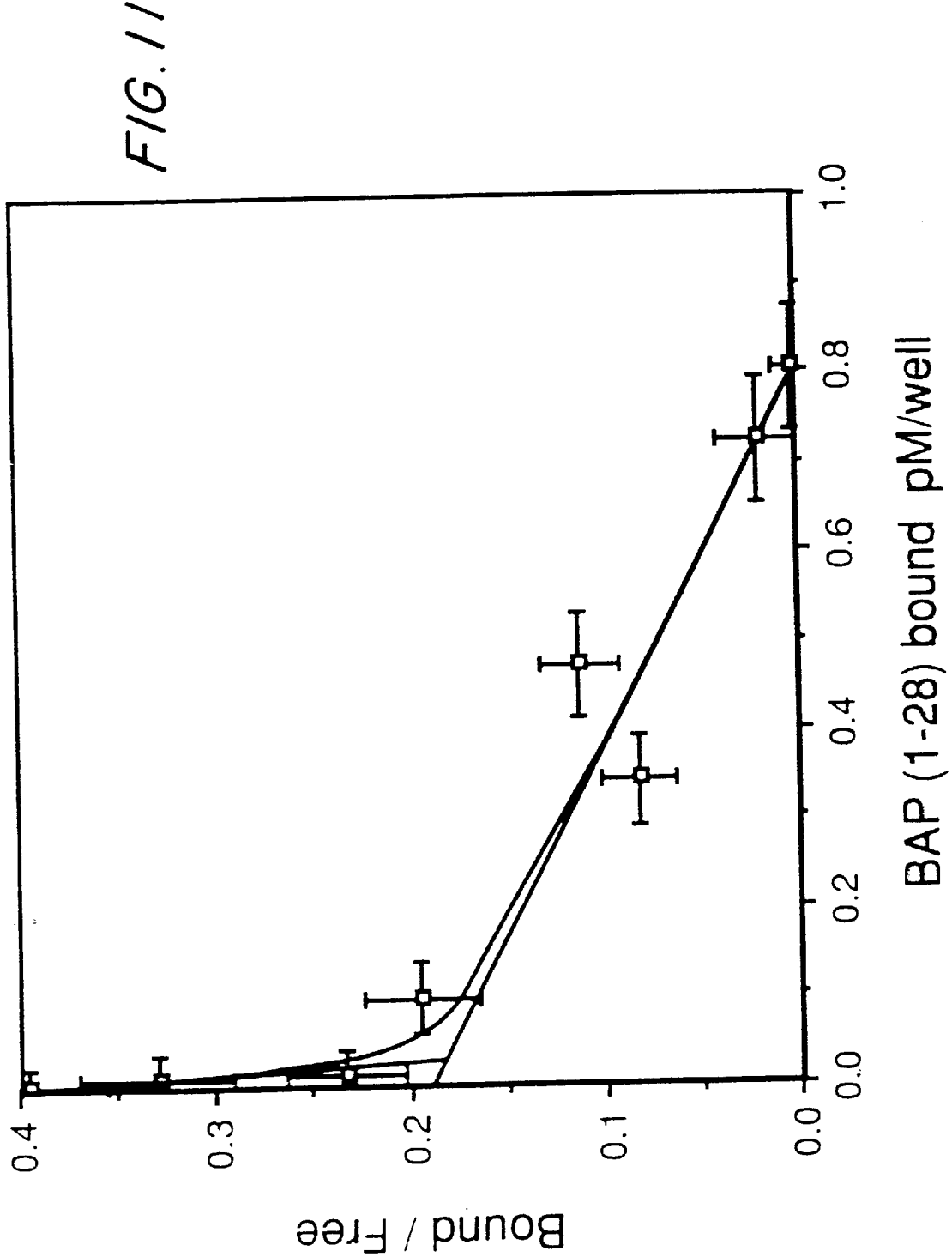

FIG. 11: Scatchard Analysis of the Binding of $^{125}$I-BAP (1–28) to High Molecular Weight HSPGs.

Nitrocellulose coated wells were incubated overnight at room temperature with 100 µl of TBS containing 1.5 µg (with 0.28 µg binding to the well) of high M$_r$ HSPG. Wells were blocked overnight at room temperature with 200 µl of 5% non-fat dried milk. After blocking, wells were rinsed 3 times with 200 µl of TBS. Various quantities of $^{125}$I-BAP (1–28) (specific activity=6,683 cpm/pm) diluted in 100 µl of TBS/0.05% Tween 20 was added in triplicate to wells and incubated for 2.5 hours at room temperature on an orbital shaker. At the end of the incubation period, free $^{125}$I-BAP was removed from each well and transferred to scintillation vials for counting. In addition, each well was washed 6 times with 200 µl of TBS/0.05% Tween 20, and the wash was added to each of the same scintillation vials described above, to determine the total "free" $^{125}$I-BAP fraction for each well. Bound $^{125}$-BAP was extracted from wells by incubation with 100 µl of 1N NaOH at room temperature for 1 hour, and quantitated by liquid scintillation counting. Recovery of $^{125}$I-BAP as free and bound radioactivity exceeded 90%. The bound radioactivity was analyzed by the Scatchard procedure and both high affinity binding sites (average $K_d$=8.3×10$^{-11}$ M) and low affinity binding sites (average $K_d$=4.2×10$^{-8}$) were found. Bars indicate standard error of the mean.

FIG. 12: Endogenous Reparan Sulfate Proteoglycan Accumulation at β/A4 Infusion Site.

Top Left: Thioflavin S fluorescence demonstrating amyloid (a) deposition adjacent to infusion site (i) following 1 week of continuous infusion of β/A4 (1–40) only.

Top Right: Thioflavin S positive site was also positive for congo red staining (arrowheads) as viewed under polarized light.

Bottom Left: High magnification of amyloid site (a) adjacent to infusion site (i) following 1 week of continuous infusion of β/A4 (1–40) only. Positive immunostaining is observed with a polyclonal antibody (1:500 dilution) to HSPG core protein suggesting that endogenous HSPG accumulates at β/A4 amyloid site within 1 week of infusion.

Bottom Right: Serial section of amyloid site (a) immunostained with the identical HSPG core protein polyclonal antibody in the presence of excess HSPG antigen, further demonstrating the specificity of the HSPG antibody used.

FIG. 13: Lack of Congo Red Staining at β/A4 Infusion Site Correlates with a Lack of Endogenous HSPG Accumulation.

Top: β/A4 (1–40) immunostaining demonstrating β/A4 (1–40) accumulation in hippocampus in animals infused with β/A4 (1–40) only.

Middle: Lack of congo red staining at β/A4 (1–40) infusion site suggesting lack of fibrillar amyloid deposition and/or persistence in brain.

Bottom: Congo red negative site is HSPG immunonegative suggesting lack of endogenous HSPG accumulation. This study suggests that endogenous HSPG accumulation is necessary for fibrillar β/A4 amyloid deposition and/or persistence in brain.

Figure 14A:
Figure 14B:
Figure 14C:

FIG. 14: Co-infusion of Heparan Sulfate Glycosaminoglycans With β/A4 (1–40) Abolishes Congo Red Staining.

Top: β/A4 (1–40) immunostaining (arrows) adjacent to infusion site following 1 week of continuous infusion of β/A4 (1–40) and HS GAGs.

Middle: Serial section immunostained with an HS GAG monoclonal antibody (HK-249) shows HS GAG deposition in exact locales as β/A4 (1–40) (arrow).

Bottom: Adjacent section (from FIG. 1, middle) demonstrating negative congo red staining (as viewed under polarized light) in β/A4 and HS GAG immunopositive areas. The inclusion of HS GAGs in conjunction with β/A4 (1–40) appeared to markedly diminish positive congo red and thioflavin S staining suggesting lack of fibrillar β/A4 amyloid deposition and/or persistence in brain.

Figures 15A, 15B:
Figure 16A:
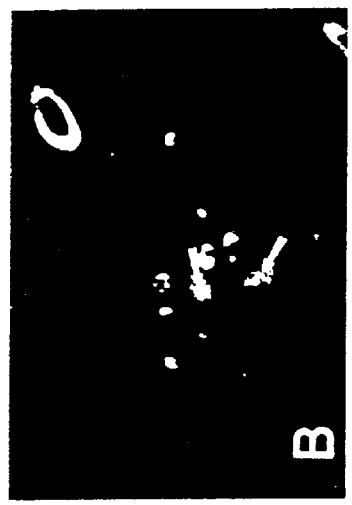
Figure 16B:
Figure 16C:
Figure 16D:

FIG. 15: The Presence of Heparan Sulfate Proteoglycans in the Characteristic Lesions of Alzheimer's Disease.

A: A monoclonal antibody (HK-249) against a specific epitope on the GAG chains of the EHS HSPG demonstrates HS GAGs in diffuse plaques (long arrows) and neurofibrillary tangles (small arrows) in Alzheimer's disease human brain.

B: A monoclonal antibody (HK-249) against a specific epitope on the GAG chains of the EHS HSPG demonstrates HS GAGs in the amyloid core protein (arrowhead) and periphery of a neuritic plaque present in Alzheimer's disease human brain.

FIG. 16: Co-Localization of β/A4 and Thioflavin S Fluorescence in Rat Infusion Model: Similarities to Alzheimer's Disease.

A: Diffuse and amyloid plaques in Alzheimer's disease brain as detected with a polyclonal antibody to β/A4 (1–40).

B: Thioflavin S fluorescence of amyloid plaques (arrows) in Alzheimer's disease brain.

C: β/A4 immunoreactivity (arrow) adjacent to infusion site in rat hippocampus following 1 week co-infusion of β/A4 (1–40) and perlecan.

D: Thioflavin S fluorescence (arrow) indicative of amyloid deposition in rat hippocampus following 1 week co-infusion of β/A4 (1–40) and perlecan. Note that thioflavin S fluorescence amyloid site is specifically co-localized to β/A4 immunoreactive site (FIG. C), a similarity to that observed in Alzheimer's disease.

Figure 17A:
Figure 17B:

FIG. 17: Extent of β/A4 Deposition in Rat Infusion Model Following 1 Week Co-infusion of β/A4 (1–40) Plus Heparan Sulfate Proteoglycans (i.e., "Perlecan").

A: Extent of β/A4 deposition in rat infusion model (arrow) as detected by positive immunostaining with a polyclonal antibody to β/A4. Infusion site is marked i.

B: Higher magnification of area shown by arrow in FIG. 17A.

FIG. 18: Co-Localization of β/A4 and Heparan Sulfate Proteoglycans Adjacent to Infusion Site Following 1 Week Co-Infusion of β/A4 (1–40) and Perlecan.

A: Deposition of β/A4 (arrows) adjacent to infusion site as detected with a polyclonal antibody against β/A4.

B: Co-localization of heparan sulfate GAGs to β/A4 deposition site as detected with a monoclonal antibody (HK-249) to a specific epitope of heparan sulfate GAGs. Co-localization of heparan sulfate to β/A4 deposition site is also observed in the brains of patients with Alzheimer's disease.

FIG. 19: Diffuse β/A4 Deposits in Rat Thalamus Following 1 Week Co-Infusion of β/A4 (1–40) and Perlecan: Similarities to Alzheimer's Disease.

A: Diffuse β/A4 deposits (arrowheads) in human Alzheimer's disease brain as detected with a polyclonal antibody to β/A4 (1–40).

B: Diffuse β/A4 deposits (arrowheads) in thalamus 2.5 mm from the center of the infusion site in rat following I week infusion of β/A4 (1–40) and perlecan. Note striking similarities to diffuse deposits in Alzheimer's disease brain (FIG. 19A).

C: Preabsorption of β/A4 immunoreactivity in thalamus when the identical β/A4 antibody was used in the presence of excess β/A4 (1–40) peptide. This demonstrates the specificity of the β/A4 antibody and the results observed in FIG. B.

FIG. 20: Alz-50 Immunostaining in Alzheimer's Disease and Rat Infusion Model.

A: Alz-50 is an antibody which recognizes the presence of abnormally phosphorylated tau protein, a specific antigen elevated in Alzheimer's disease brain. FIG. 20A demonstrates Alz-50 immunostaining of dystrophic neurites (large arrowheads) surrounding amyloid plaques, and neurofibrillary tangles (small arrowheads) in Alzheimer's disease brain.

B: Strong Alz-50 immunostaining (arrows) adjacent to infusion site (i) in rat hippocampus following 1 week co-infusion of β/A4 (1–40) and perlecan. This demonstrates that the animal model protocol also induces an Alzheimer's disease antigen.

C: Lack of Alz-50 immunostaining (arrows) adjacent to infusion site (i) in rat hippocampus following 1 week infusion of perlecan only. This observation demonstrates that the infusion of β/A4 (1–40) as part of the protocol is important for increased Alz-50 immunostaining.

Figure 21A:
Figure 21B:
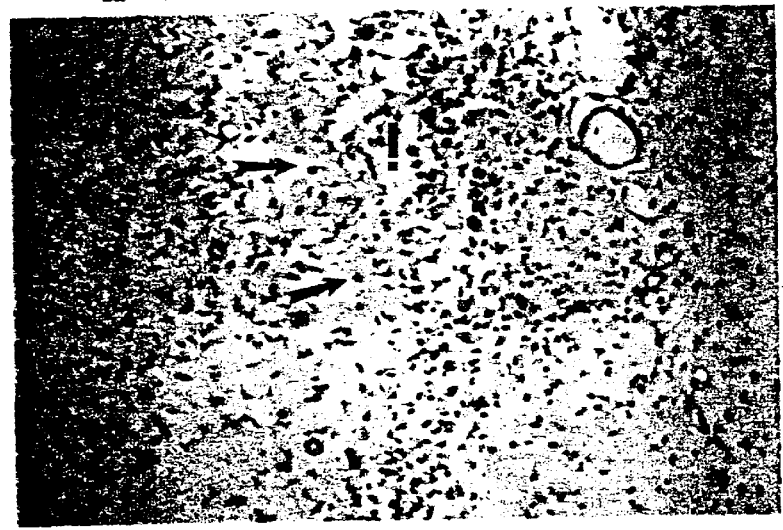
Figure 21C:

FIG. 21: Alz-50 Immunostaining in the Rat Infusion Model.

A: Alz-50 is an antibody which recognizes the presence of abnormally phosphorylated tau protein, a specific antigen elevated in Alzheimer's disease brain. FIG. 21A demonstrates Alz-50 immunostaining (arrows) adjacent to infusion site (i) following 1 week of co-infusion with β/A4 (1–40) plus perlecan.

B: Lack of Alz-50 immunostaining (arrows) adjacent to infusion site (i) following 1 week infusion of perlecan only.

C: Lack of Alz-50 immunostaining (arrows) adjacent to infusion site (i) following 1 week infusion of heparan sulfate GAGs only.

Figure 22B:

FIG. 22: Neurodegenration in Rat Brain Following 1 Week Co-infusion of β/A4 (1–40) and Perlecan: Similarities to Alzheimer's Disease.

A: Modified Bielchowsky silver staining in Alzheimer's brain demonstrating dystrophic neurites and/or degenerating neurons (arrowheads).

B: Similar dystrophic neurites and/or degenerating neurons is observed (arrowheads) in rat cerebral neocortex 2 mm from the center of the infusion site following 1 week co-infusion of β/A4 (1–40) and perlecan.

Figures 23A, 23B, 23C, 23D:

FIG. 23: Astrocyte and Microglia/Macrophage Involvement in Rat Infusion Model: Similarities to Alzheimer's Disease.

A: Low magnification of GFAP immunostaining, a specific marker of astrocytes, following 1 week co-infusion of β/A4 (1–40) and perlecan. Astrocytes surround amyloid (a) deposition areas adjacent to infusion site (i).

B: Higher magnification from FIG. 23A demonstrating GFAP immunostaining of astrocytes (arrowheads) surrounding amyloid (a) deposition sites adjacent to infusion site (i). Astrocytes surrounding amyloid deposits occur in the brains of patients with Alzheimer's disease.

C: Low magnification of ED1 immunostaining, a specific marker of microglia/macrophages, following 1 week co-infusion of β/A4 (1–40) and perlecan. Note that microglia/macrophages (red dots-alkaline phosphatase method) infiltrate amyloid deposition areas adjacent to infusion site (i).

D: Higher magnification from FIG. 23D demonstrating ED1 immunostaining (arrowheads) indicative of microglia/macrophages within areas of amyloid deposition adjacent to the infusion site (i). Microglia/macrophages are found within areas of amyloid deposition in the brains of patients with Alzheimer's disease.

Figure 24:
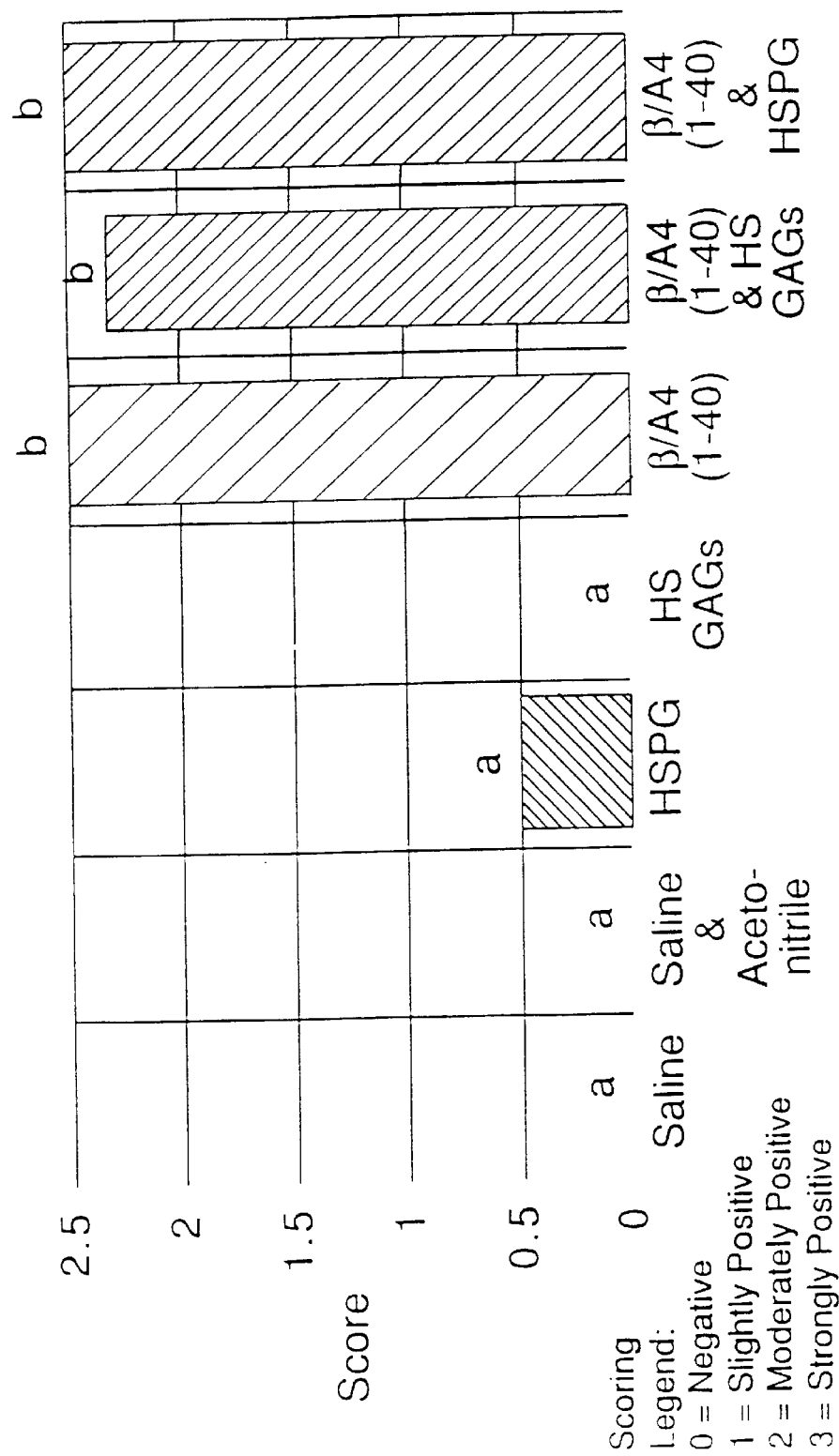

FIG. 24: Scoring of β/A4 Immunostaining in Rat Infusion Model.

Two independent investigators scored slides immunostained for β/A4 (140) in each of the seven 1-week infusion groups (see below for details of scoring criteria and statistical evaluation). All groups containing β/A4 (1–40) as part of vehicle demonstrated a significant increase (p<0.001) in β/A4 immunostaining adjacent to the infusion site.

Figure 25:
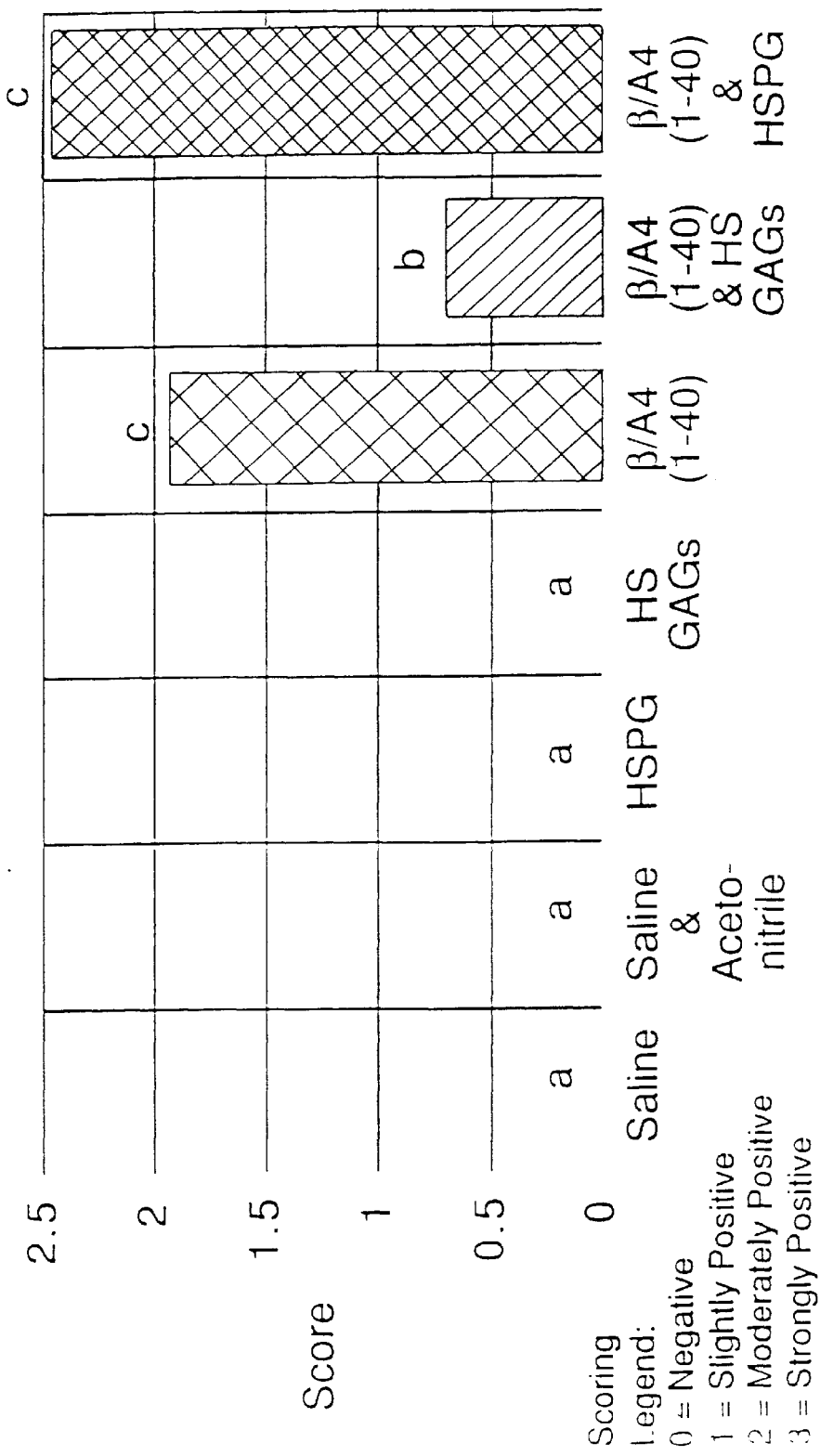

FIG. 25: Scoring of Congo Red Staining in Rat Infusion Model.

Two independent investigators scored slides stained with congo red in each of the seven 1-week infusion groups (see page of patent application for details of scoring criteria and statistical evaluation). Note that both the β/A4 (1–40) & HSPG and the β/A4 (1–40) only groups show a significant increase in congo red staining than other groups. Also the group infused with β/A4 (1–40) & HS GAGs shows a significant decrease in congo red staining indicating that HS GAGs are capable of diminishing amyloid fibril deposition and/or persistence in brain.

Figure 26:
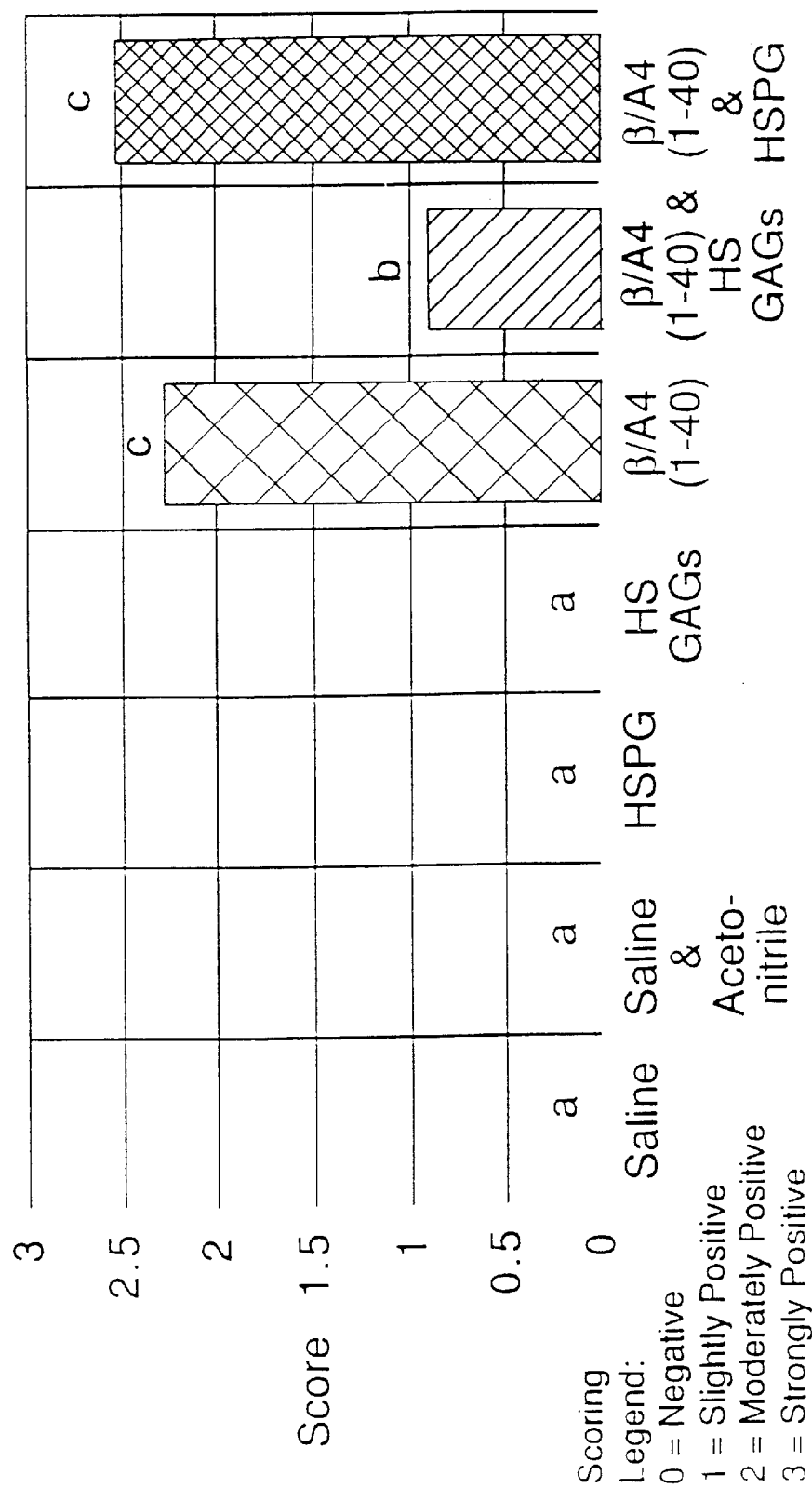

FIG. 26: Scoring of Thioflavin S Fluorescence in Rat Infusion Model.

Two independent investigators scored slides stained with Thioflavin S of patent in each of the seven 1-week infusion groups (see below for details of scoring criteria and statistical evaluation). Note that both the β/A4 (1–40) & HSPG and the β/A4 (1–40) only groups show a significant increase in thioflavin S fluorescence than other groups. Also, the group infused with β/A4 (1–40) & HS GAGs shows a significant decrease in thioflavin S fluorescence indicating that HS GAGs are capable of diminishing amyloid fibril deposition and/or persistence in brain.

Figure 27:
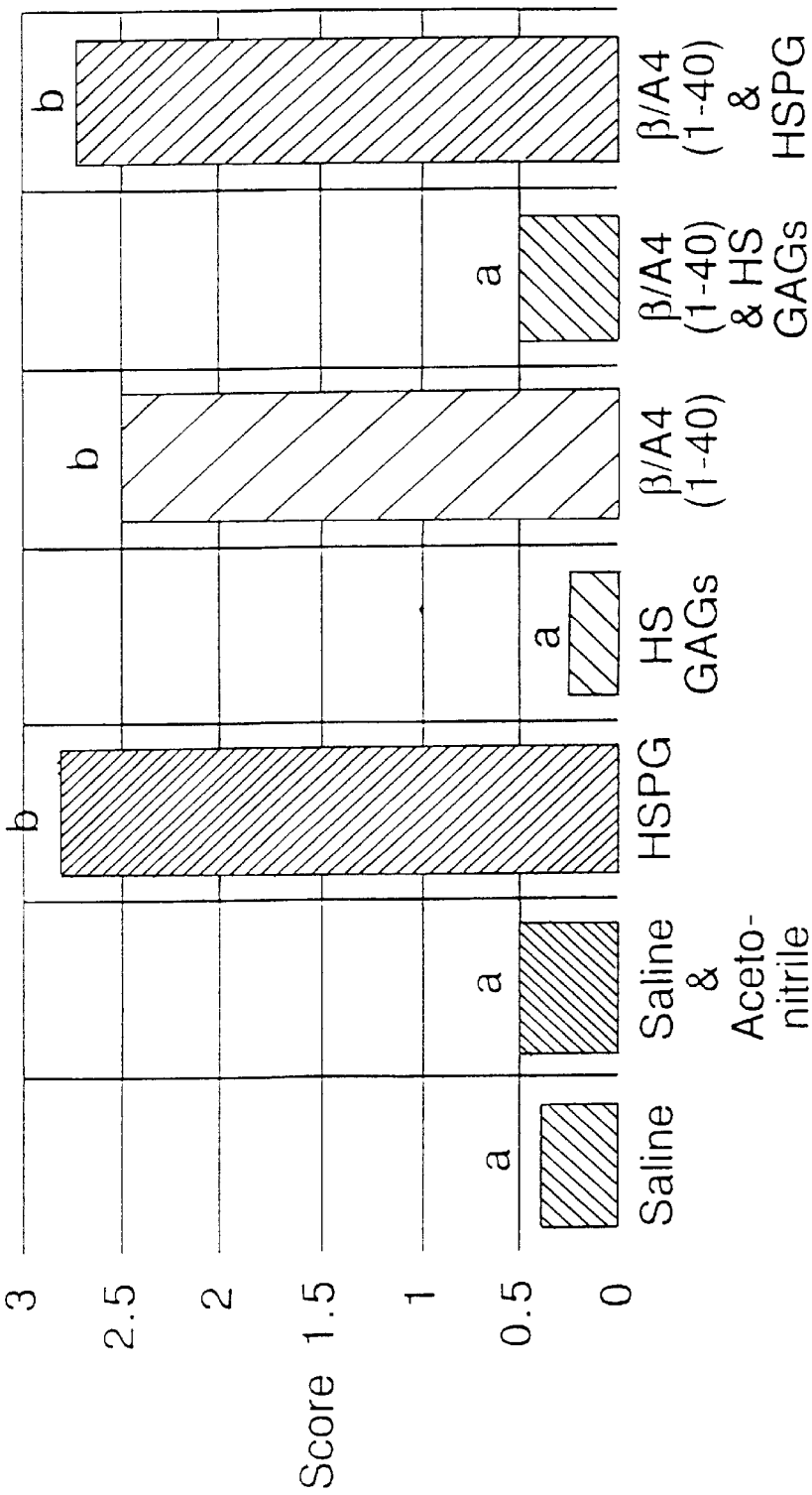

FIG. 27: Scoring of Heparan Sulfate Proteoglycan Core Protein Immunostaining in Rat Infusion Model.

Two independent investigators scored slides immunostained with a polyclonal antibody to HSPG core protein in each of the seven 1-week infusion groups (see below for details of scoring criteria and statistical evaluation). Note that even though HSPG was not infused in the group given β/A4 (1–40), HSPG immunostaining is not significantly different than groups where HSPG was part of the infusate. This implies that when β/A4 (1–40) in infused alone, endogenous brain HSPG accumulation occurs at infusion site.

Figure 28:
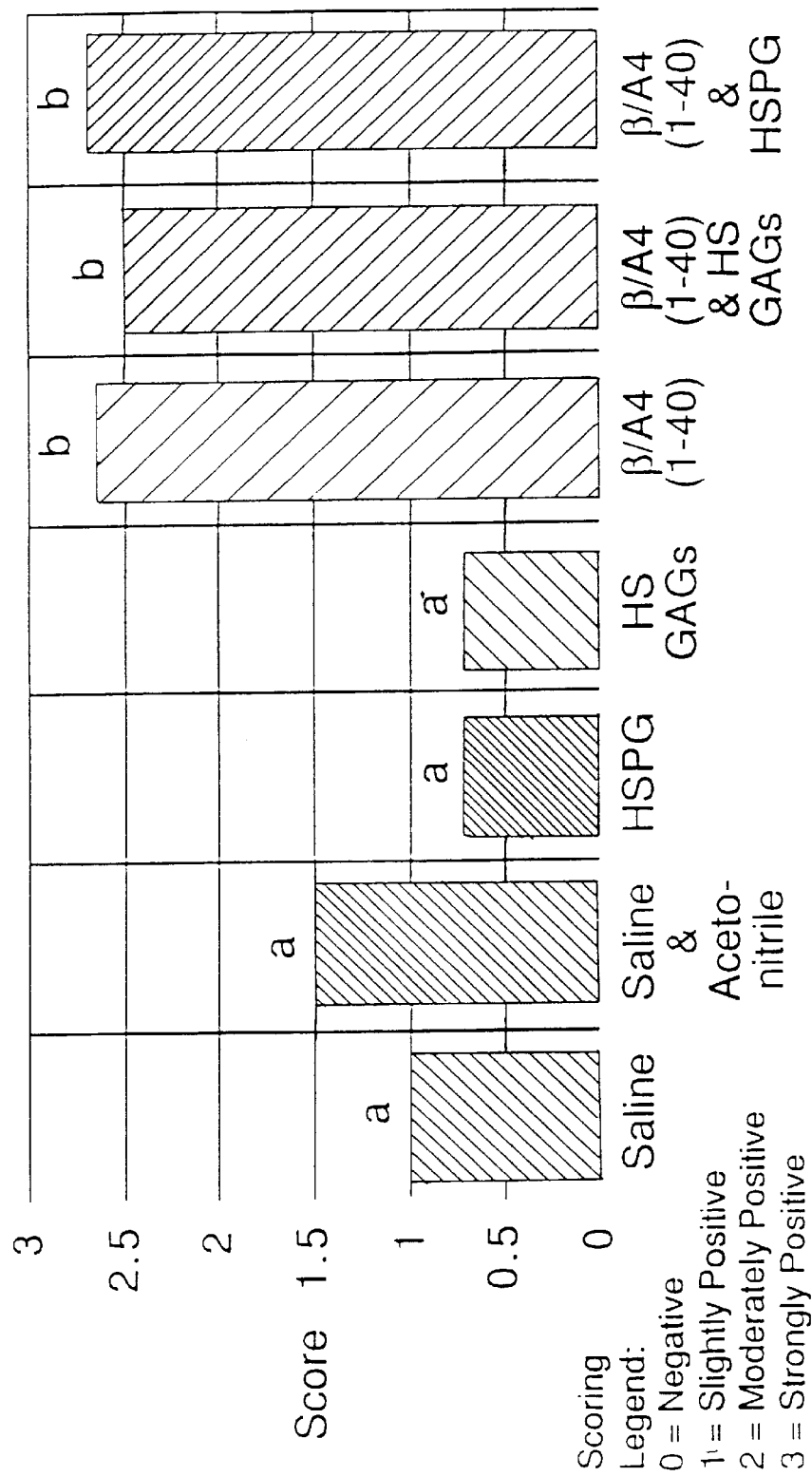

FIG. 28: Scoring of Alz-50 Immunostaining in Rat infusion Model.

Two independent investigators scored slides immunostained with a Alz-50 antibody in each of the seven 1-week infusion groups (see below for details of scoring criteria and statistical evaluation). Note that all groups infused with β/A4 (1–40) as part of the infusate demonstrate a significant increase in Alz-50 immunostaining.

Figure 29:
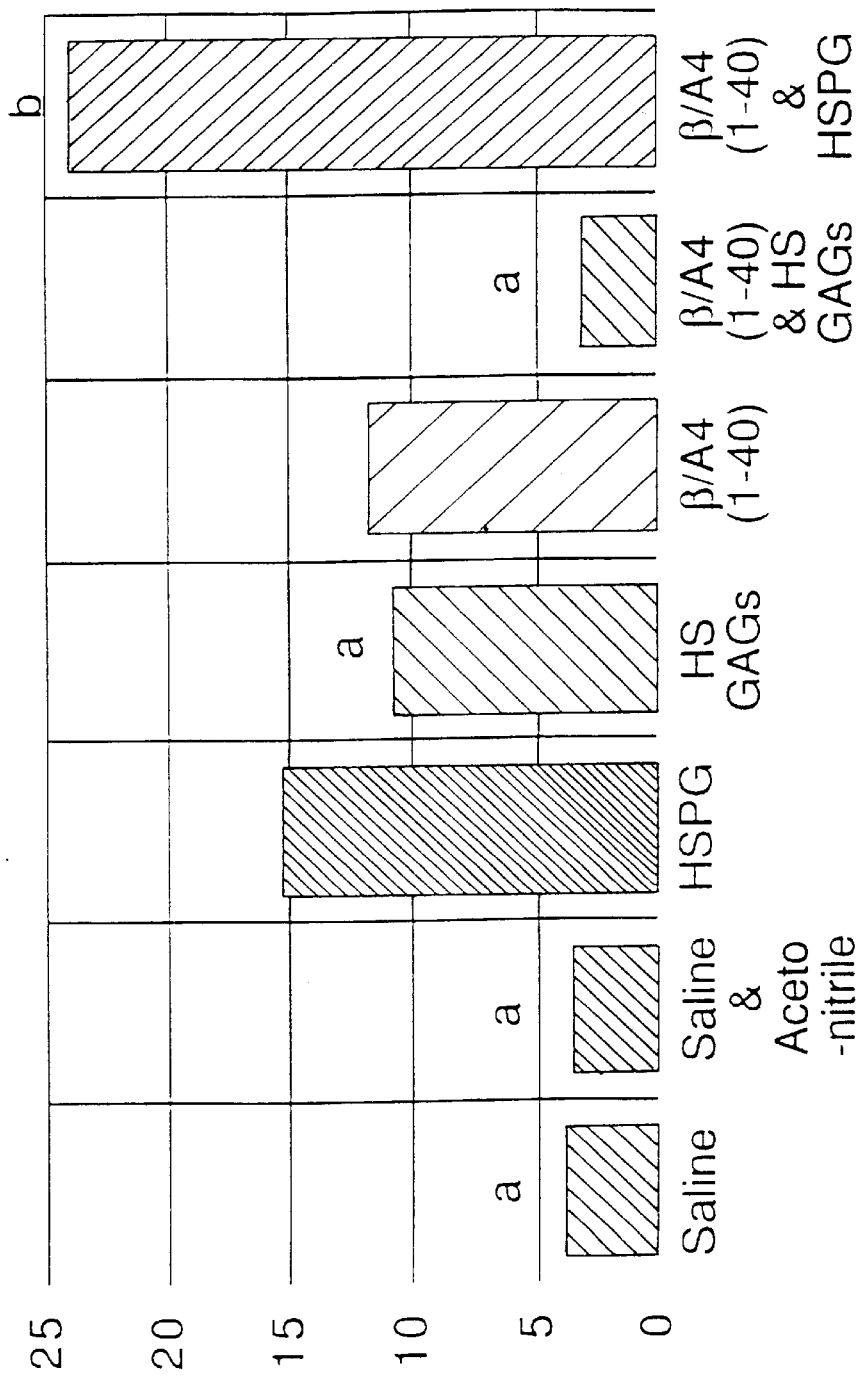
Figure 3I:
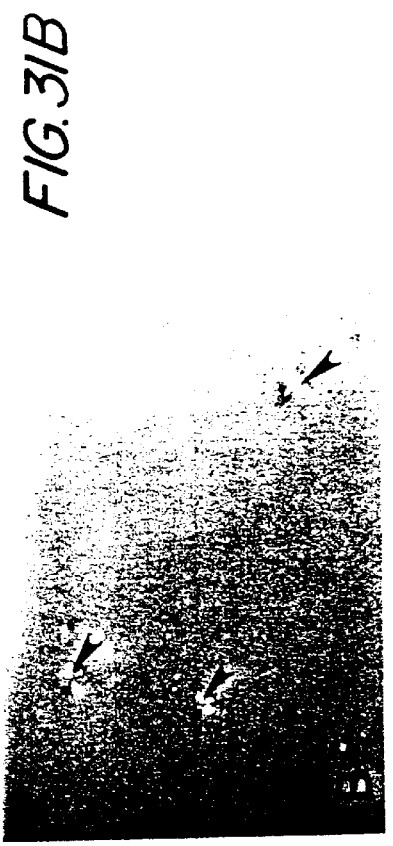
Figure 3I:
Figure 3I:
Figure 3I:
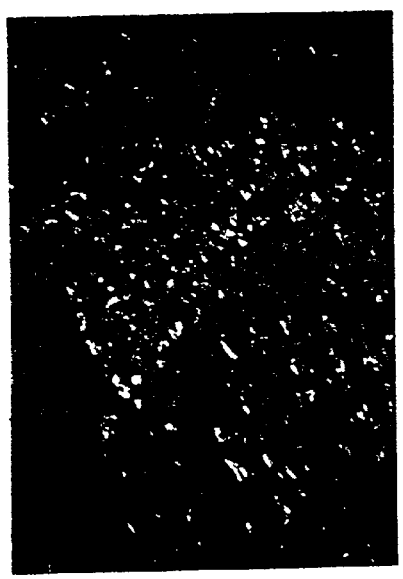

FIG. 29: Quantitation of Silver Positive Neurons in Rat Infusion Model.

Two independent investigators counted the number of silver stained (using modified Bielchowsky stain) neurons in each of the seven 1-week infusion groups (see below for details of scoring criteria and statistical evaluation). A significant increase in silver 6 positive neurons was found in the group infused with β/A4 (1–40) & HSPG in comparison to the other groups.

FIG. 30: Scoring of ED1 Immunostaining in Rat Infusion Model.

Two independent investigators scored slides immunostained with ED1 in each of the seven 1-week infusion groups (see below for details of scoring criteria and statistical evaluation). All groups infused with any type of macromolecule (i.e., β/A4, HSPG, HS GAGs, or combinations thereof) demonstrated positive ED1 immunostaining indicative of microglia/macrophage infiltration.

FIG. 31: Congophilic Amyloid Deposition 1 Week and 7 Weeks Following Co-Infusion of β/A4 (1–40) and Perlecan.

A: Congo red staining of neurofibrillary tangles (arrowheads) in hippocampus of patient with Alzheimer's disease as viewed under polarized light.

B: Congo red staining of amyloid plaque cores (arrowheads) in hippocampus of patient with Alzheimer's disease as viewed under polarized light. Note spherical shape of amyloid plaques.

C: Congo red staining of amyloid deposits (arrowheads) adjacent to infusion site following 1 week co-infusion of β/A4 (1–40) & perlecan. Note flame-shaped appearance of amyloid deposits is similar to flame-shaped appearance of neurofibrillary tangles (FIG. 31A).

D: Congo red staining of spherical amyloid plaques (arrowheads) adjacent to infusion site following 7 weeks (2-week infusion, and 5-week non-infusion) co-infusion of β/A4 (1–40) & perlecan. Note that the amyloid plaque are identical in appearance and morphology to amyloid plaque present in Alzheimer's disease brain (FIG. 31B).

Figure 32A:
Figure 32B:
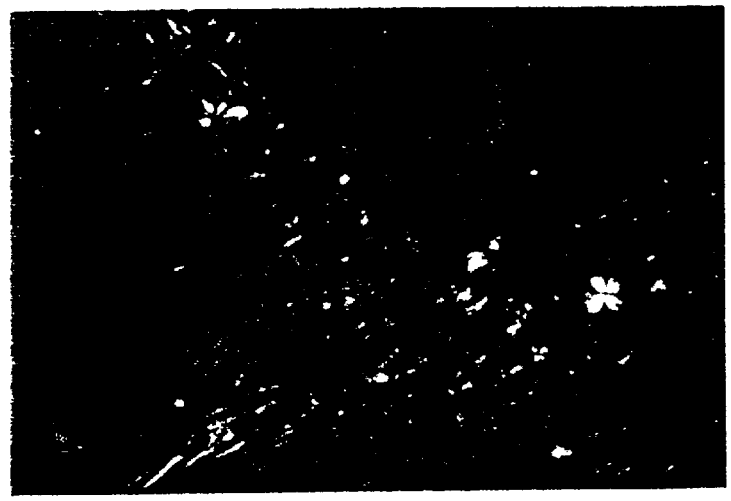
Figure 32C:

FIG. 32: Congophilic Amyloid Deposition in Rat Hippocampus 7 Weeks Following Co-Infusion of β/A4 (1–40) and Perlecan.

Animals were infused for 2 weeks with β/A4 (1–40) & perlecan, and then sacrificed 5 weeks later (total time=7 weeks).

A: Low magnification of hippocampus demonstrating massive amyloid deposition (arrows) adjacent to infusion site (i), as demonstrated by positive congo red staining as viewed under polarized light.

B: Higher magnification adjacent to infusion site (i) demonstrating spherical amyloid plaques (arrowhead).

C: In an area further away from the infusion site, spherical amyloid plaques (arrowheads) are also demonstrated by positive congo red staining as viewed under polarized light.

FIG. 33: High Magnification of Extracellular Amyloid Plaque in Rat Hippocampus 7 Weeks Following Co-Infusion of β/A4 (1–40) and Perlecan.

Animals were infused for 2 weeks with β/A4 (1–40) & perlecan, and then sacrificed 5 weeks later (total time=7 weeks).

A: Extracellular amyloid plaque (arrowhead) as demonstrated by congo red staining viewed under polarized light.

B: Rotation of the polarizer from FIG. 33A shows a classic shift in colors. Areas that were once red (in FIG. 33A) are now green, and areas that were once green (in FIG. 33A) are now red. This phenomenon is known as red/green birefringence and is indicative of amyloid and its characteristic predominant beta-pleated sheet secondary structure.

FIG. 34: Current Classification of Amyloidoses.

This figure shows the current classification of amyloidoses and their associated diseases.

FIG. 35: Highly Sulfated Proteoglycans (i.e., Heparan Sulfate): A Common Constituent of All Amyloids.

This figure demonstrates evidence (histochemical, immunocytochemical and/or biochemical data) for the presence of highly sulfate proteoglycans/glycosaminoglycans in all amyloids regardless of the nature of the amyloid protein present. Numbers refer to reference numbers in manuscript by Snow and Wight, Neurobiol. Aging 10:481–497, 1989.

FIG. 36: Outlines Screening for Determining Which Agents (e.g., GAGs, Peptides) Are Capable of Inhibiting HSPG-β/A4 Binding.

FIG. 36: Quantitative Analysis of Staining, Immunostaining and Silver-Positive Neurons in the Various Infusion Groups Table 1).

Groups of animals were continuously infused for 1 week into hippocampus with saline, saline & acetonitrile, or β/A4 (1–40) in the presence of absence of specific PGs or GAGs. Two investigators blindly scored an average of 3–5 slides per stain/immunostain per animal in order to quantitate possible differences between the various infusion groups. Approximately every 10th 6 μm serial section was identically stained or immunostained to allow for an assessment spanning the entire infusion area. Four animals per infusion group were scored with the exception of the saline and acetonitrile group where two animals were scored. Immunostaining with antibodies to β/A4 (1–40), HS GAGs (HK-249), HSPG core protein, Alz-50 and ED1 were all scored at the area adjacent to the infusion site (at magnifications of 25X and 100X). Congo red and thioflavin S staining was also evaluated at the areas adjacent to the infusion site (at a magnification of 100X). Scoring for staining/immunostaining was as follows: 0=negative; 1=slightly positive; 2=moderately positive; 3=strongly positive; both staining/immunostaining intensity and the extent of staining/immunostaining adjacent to the infusion area were taken into account for scoring. Quantitation of the number of Bielchowsky silver positive neurons in the hippocampus was scored at a magnification of 25X and 100X. Neurons were identified by Nissl staining on adjacent serial sections. All measures except Bielchowsky stained cells were statistically analyzed using nonparametric tests (Kruskal-Wallis test for overall effects followed by Wilcoxon-Mann-Whitney test for individual group comparisons). For Bielchowsky stained cells, ANOVA was followed by Newman-Keul's test for individual group comparisons.

FIG. 37: Outlines Testing of Potential GAG Inhibitors or Peptides for Their Conformational Effects on Various β/A4 Peptides.

FIG. 38: Outlines Tests Using the Rapid Animal Model of β/A4 Amyloid Deposition to Determine the In Vivo Effects of Candidate Macromolecules Identified in the FIG. 36 and FIG. 38 Protocols.

FIG. 39: Outlines Testing of the Candidate Macromolecules for Non-Toxicity.

FIG. 40: Outlines Representative Human Testing of the Candidate Macromolecules.

FIG. 41 is "Table 1" as described in the specification.

DETAILED DESCRIPTION OF THE PREFERRED EMBODIMENT

I. Summary of Data Establishing the Rapid Animal Model of β/A4 Amyloid Deposition in Brain.

For infusion studies, all reagents were dissolved and stored at 4° C. the night prior to surgery. β/A4 (residues 1–40; Bachem California Inc., Torrance, Calif.; Lot #ZJ209) was initially dissolved at 10 mg/ml in 35% acetonitrile (stock solution), with the final diluted concentration of acetonitrile less than 3% in animals infused with β/A4 or its vehicle (see below). Perlecan (basement membrane derived HSPG) and heparan sulfate (HS) GAGs were isolated and purified from the mouse Engelbreth-Holm-Swarm (EHS) sarcoma as described (6), and dissolved in sterile saline at 5 mg/ml and 10 mg/ml, respectively. Male Sprague-Dawley rats (250–300 gms; 3 months old; Harlan Sprague Dawley) were implanted with Alzet 2002 minipumps delivering the following solutions directly into hippocampus at a flow rate of 0.5 μl per hour for one week (7); 1) β/A4 (7.5 μl stock) & HSPG (92.5 μl stock), 6 animals; 2) β/A4 (7.5 μl stock) & HS GAGs (92.5 μl stock), 4 animals; 3) β/A4 (7.5 μl stock) & saline (92.5 μl), 6 animals; 4) HSPG only (100 μl), 4 animals; 5) HS GAGs only (100 μl), 4 animals; 6) saline only (100 μl), 4 animals; and 7) 35% acetonitrile (β/A4 vehicle, 7.5 μl) & saline (92.5 μl), 2 animals. High concentrations of these reagents were chosen to maximize possible effects following infusion into brain. The approximate quantity of β/A4 peptide infused into brain by the end of 1 week in each animal having β/A4 (1–40) as part of the infusate was 75 μg, at least 5 times the amount previously reported in rat models employing single acute injections (8, 9). After one week of continuous infusion, rats were sacrificed by overdose with pentobarbital and perfused with 100 ml of saline followed by 150 ml of 4% paraformaldehyde buffered with phosphate (pH 7.4), postfixed for 24 hours and transferred to phosphate buffered saline for paraffin embedding. Once embedded, consecutive 6 μm serial sections were cut and placed on poly-D-lysine coated slides. Two additional animals in the β/A4 only and the β/A4 & HSPG groups were processed for electron microscopy as described (10).

Consecutive serial sections revealed that the infusion site (on hematoxylin and eosin stained sections) spanned an average of twenty to forty 6 μm serial sections. Amyloid deposition was demonstrated by 1) congo red staining (11), 2) thioflavin S fluorescence (12), and 3) electron microscopy. Detection of infused macromolecules was monitored using two polyclonal antibodies against synthetic β/A4 (either against β/A4 1–28 or 1–40) (13), and two monoclonal antibodies recognizing either HS GAGs (HK-249) (14) or the core protein of perlecan (HK-102) (15). Additionally, two polyclonal antibodies recognizing the core protein of perlecan (17) assessed effects of infused macromolecules (16) on endogenous brain HSPGs. Detection of other AD-like markers included Alz-50 antibody immunostaining (18), and silver staining by the modified Bielschowsky method (19). Possible inflammation-associated amyloid protein involvement was monitored by AA amyloid protein immunostaining (20). The presence of other cell types such as astrocytes was detected by immunostaining with a polyclonal antibody to glial fibrillary acidic protein (GFAP) (1:10,000 dilution; Dako), whereas microglia/macrophage infiltration was detected using a rat monoclonal antibody known as ED1 (1:2500 dilution; Serotec). For all immunostaining, negative controls consisted of using Tris-buffered saline (TBS) instead of the primary antibody, and/or preabsorption experiments using the primary antibody in the presence of excess antigen. In order to quantify possible staining and/or immunostaining differences between the various infusion groups, slides were scored blindly by two independent investigators as described (21) (Table 1; see FIG. 35).

Figure 2A:
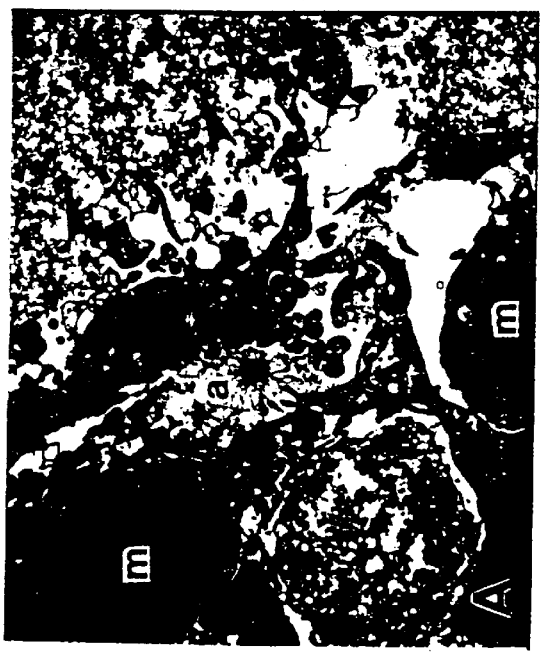
Figure 2B:
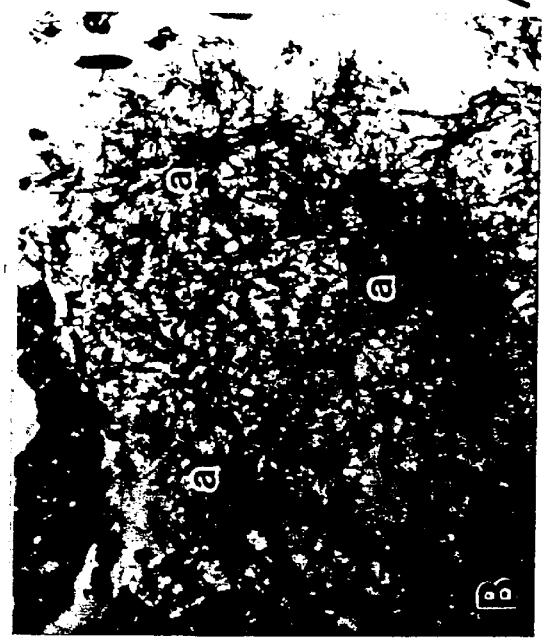
Figure 2C:
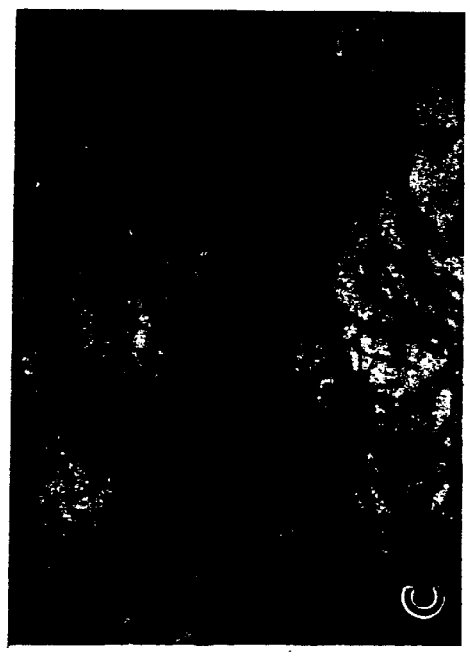
Figure 2D:
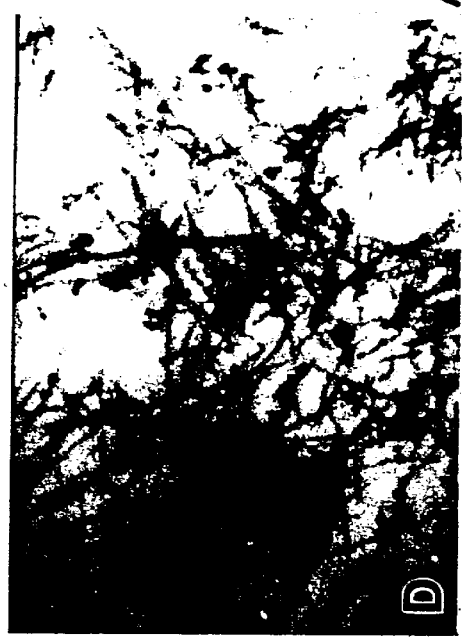

100% (6 of 6) of animals in the group receiving β/A4 (1–40) & HSPG, within 1 week of infusion, demonstrated deposition of congophilic material in brain characteristic of amyloid (FIG. 1A). In comparison, 4 of 6 animals in the group receiving only β/A4 demonstrated deposition of congophilic amyloid material in brain. The congophilic material was similar in appearance to congo red staining of intracellular and/or extracellular NFTs in the brains of AD patients (22). These congo red positive areas also stained with thioflavin S (FIG. 1B), showing fluorescent staining similar to extracellular amyloid deposits in human AD brain (23). The location and nature of the amyloid deposited in the β/A4 & HSPG and the β/A4 only groups was confirmed at the ultrastructural level by electron microscopy (FIG. 2). Amyloid deposits consisting of fibrils with a diameter of 10–12 nm were observed extracellularly, adjacent to the infusion site, usually surrounded by microglia/macrophages (FIGS. 2A–B). Amyloid fibrils were occasionally observed within the cytoplasm of microglia/macrophages, most likely indicative of phagocytosis of amyloid by these cells. In addition to extracellular accumulation of fibrillar amyloid, amorphous material was observed adjacent to the infusion site (FIG. 2A, arrowheads). Immunogold labelling with an antibody to β/A4 (1–40) demonstrated gold particles specifically localized to fibrils (FIG. 2C) and to extracellular amorphous material. Little to no immunogold labelling was observed in these areas when the same β/A4 antibody was used in the presence of excess β/A4 (1–40) peptide (FIG. 2D).

Congo red and thioflavin S positive sites were also immunopositive for β/A4 (1–40) (FIGS. 1C–D; Table 1) and β/A4 (1–28) (not shown). β/A4 immunostaining adjacent to the infusion site was not observed in other groups when β/A4 (1–40) was not part of the infusate (FIG. 1; Table 1). Two of six animals co-infused with β/A4 & HSPG also demonstrated diffuse β/A4 (1–40) immunoreactive deposits in thalamus (FIG. 1F) approximately 2.5 mm from the center of the infusion site. These β/A4 diffuse deposits were congo red and thioflavin S negative, and closely resembled diffuse plaques present in AD brain (3). None of the other groups displayed similar diffuse β/A4 deposits. β/A4 immunostaining was not observed in the contralateral hemisphere of animals infused with β/A4 as part of the infusate, or in normal rat brain.

Figure 1G:
Figure 1L:
Figure 1K:
Figure 1J:
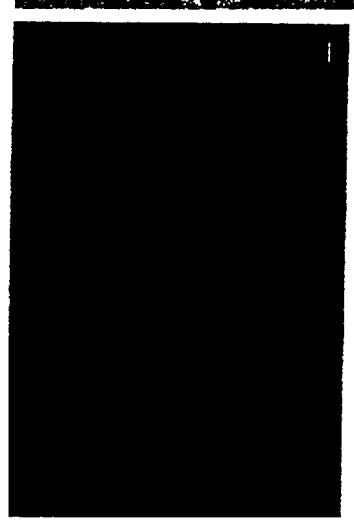

In the β/A4 & HSPG group, the infused HSPG was specifically co-localized to β/A4 immunopositive sites adjacent to the infusion site (FIG. 1G). Importantly, HSPG immunostaining was also found in four animals infused with β/A4 (1–40) only, even though HSPG was not part of the infusate (FIG. 1I). This HSPG immunostaining co-localized with β/A4 immunostaining and with congo red and thioflavin S (FIG. 1H) staining in these rats. The HSPG immunostaining was abolished when the identical antibodies were used in the presence of excess HSPG antigen (FIG. 1J). In two other animals receiving β/A4 only, neither HSPG immunostaining nor congo red/thioflavin S positive areas were observed, implying that HSPG accumulation at the β/A4 infusion site may be necessary for congo red staining and/or amyloid persistence in vivo.

Surprisingly, the group of animals infused with β/A4 & HS GAGs failed to deposit congophilic and thioflavin S amyloid after 1 week. Although immunostaining revealed that both β/A4 (FIG. 1K) and HS GAGs (not shown) were deposited adjacent to the infusion site, inclusion of HS GAGs in the infusate appeared to diminish or prevent congo red (FIG. 1L) and thioflavin S staining, as well as decrease the number of silver positive neurons (Table 1). These observations imply that highly sulfated GAGs such as HS may prevent amyloid fibril assembly and/or its persistence in brain. Since previous data suggest that highly sulfated GAGs such as heparin are competitive inhibitors for β/A4 binding to HSPG (4), it is feasible that HS GAG inclusion in the β/A4 infusate may serve as a competitive inhibitor for β/A4 binding to endogenous brain HSPG.

Figure 3A:
Figure 3D:

Animals infused with β/A4 & HSPG also demonstrated a number of silver positive neurons and/or dystrophic neurites in the cerebral neocortex approximately 2 mm dorsal and 2 mm medial from the center of the infusion site (FIG. 3A). These silver positive neurons appeared similar in appearance to Bielchowsky stained NFTs and/or dystrophic neurites in human AD brain (24). Quantitation of silver positive neurons demonstrated a significant difference (p<0.05) between the number found in the β/A4 & HSPG group, in comparison to saline, saline & acetonitrile, and groups using HS GAGs (Table 1).

Two animals infused with β/A4 & HSPG also demonstrated Bielchowsky positive staining in the walls of capillaries and small arterioles in the cerebral neocortex (FIG. 3B) (2 mm from the center of the infusion site), similar in appearance to Bielchowsky silver staining of amyloid-laden vessels in human AD brain (19). None of the other groups demonstrated silver positive vessels.

All animals infused with β/A4 (1–40) as part of the infusate demonstrated strong Alz-50 immunostaining (FIG. 3C) co-localized to β/A4 deposition sites on adjacent serial sections (see FIG. 1C) irrespective of whether congophilic amyloid was present, suggesting induction of abnormally phosphorylated tau protein (18). Alz-50 immunostaining was not observed when tissues were immunostained using TBS instead of the primary antibody. All groups infused with β/A4 (as part of the infusate) demonstrated a significant greater (p<0.01) Alz-50 immunostaining adjacent to the infusion site in comparison to other groups (FIG. 3D) (Table 1).

Increased GFAP immunostaining was generally observed in all groups adjacent to the infusion site. In animals with congophilic β/A4 amyloid deposits GFAP immunostaining was observed in the vicinity of the infusion site, close to, but not within, areas of amyloid deposition (FIG. 1E). The majority of cells localized within the β/A4 amyloid deposition sites were identified using the ED1 antibody as microglia/macrophages (FIG. 1F). This agrees with previous studies of microglia/macrophage localization at the site of injection of various macromolecules (4,5). Microglia/macrophage infiltration at the infusion site was observed to some extent in all groups with significant lower scores (p<0.05; Table 1) in the vehicle groups, in comparison to other groups (Table 1). The pattern of glial reactivity (surrounding but not internal to amyloid deposits), with phagocytes internal to amyloid deposits, is remarkably similar to the cellular organization in and near AD amyloid (25).

To conclude, congophilic, fibrillar β/A4 amyloid can be deposited in rat brain within 1 week. A specific HSPG (perlecan) appears critical for congophilic β/A4 amyloid deposition in vivo based upon 1) co-infusion of HSPGs with β/A4 (1–40) consistently produces congophilic and fibrillar amyloid, 2) animals infused with β/A4 only apparently induce endogenous HSPG accumulation at β/A4 sites and 3) perlecan binds β/A4 with high affinity (4). Whereas other AD plaque components probably play crucial roles in the pathogenesis of this disease, they do not appear critical for amyloid formation. The present success in consistently producing congophilic amyloid deposits in rat brain provides the basis for a rat model to study effects of β/A4 amyloid on neighboring brain tissue. Advantages of this model include rapidity, the use of defined components, and the capacity to deposit amyloid in selected brain regions. Such a model serves in elucidating the role of congophilic fibrillar β/A4 amyloid in the pathogenesis of AD, to screen potential therapeutics for this disorder.

MATERIALS AND METHODS

1. G. G. Glenner and C. W. Wong, Biochim. Biophys. Res. Comm. 120, 885 (1984); C. W. Wong, V. Quaranta and G. G. Glenner, Proc. Natl. Acad. Sci. 82, 8729 (1985); C. L. Masters et al., ibid, p. 4245; K. Beyreuther and C. L. Masters, Neurobiol. Aging 11, 66 (1990).

2. D. M. Noonan et al., J. Biol. Chem. 263, 16379 (1988); ibid 266, 22939 (1991).

3. A. D. Snow et al., Am. J. Path. 133, 456 (1988); ibid 137, 1253 (1990).

4. A. D. Snow et al., J. Neuropath. Exp. Neurol. 48, 352 (1989); ibid, Soc. Neurosc. 21st Ann.Meet., New Orleans, Nov. (1991) abstract 439.12.

5. S. Narindrasorasak et al., J. Biol. Chem. 266, 12878 (1991).

6. Perlecan was isolated from the basement membrane producing mouse tumor as described by Kato et al., J. Biol. Chem. 262, 7180 (1987). This particular HSPG had a $M_r$ of >700,000, was digestible with heparitinase yielding a core protein of $M_r$~400,000. The HSPG preparation showed no contamination by other macromolecules as determined by Alcian blue-silver staining as described in R. C. Krueger Jr. and N. B. Schwartz, Anal. Biochem. 167, 295 (1987). Heparan sulfate GAGs were isolated from the EHS tumor as described in H. Habuchi et al., Biochem. J. 285, 805 (1992).

7. Rats were anesthetized with pentobarbital (50 mg/kg) and a 27 gauge steel cannula was stereotactically implanted into the hippocampus using bregma as reference point (AP −4.8; ML 3.5; DV 4), and secured to the skull by machine screws and dental acrylic. The cannula was connected via a 15 cm coil of vinyl tubing to a model 2002 osmotic minipump (Alzet Inc.) placed subcutaneously beneath the shoulder blades. The infused solution was contained entirely within the coil of vinyl tubing and separated from saline in the pump (dyed blue with food coloring) by a 3 cm air spacer. Successful performance of the pumps was confirmed after perfusion by measuring movement of the air spacer and blue saline solution.

8. N. W. Kowall et al., Proc. Natl. Acad. Sci., 88, 7247 (1991).

9. S. A. Frautschy, A. Baird and G. M. Cole, ibid 88, 8362 (1991); ibid, Am. J. Path. 140, 1389 (1992).

10. Animals were initially perfused with 100 ml of sterile saline, followed by perfusion with 150 ml of 3% glutaraldehyde/1.5% paraformaldehyde in 0.1M cacodylate buffer (pH 7.4), followed by 0.15M Tris-HCl (pH 7.4). After careful dissection of tissue adjacent to the infusion site, tissue was further postfixed for 1 hour at room temperature with 2% paraformaldehyde/2.5% glutaraldehyde in 0.1M phosphate buffer (pH 7.4). The rest of the procedure for preparation of the tissues for electron microscopy is as described in A. D. Snow et al., Am. J. Path. 133, 456 (1988).

11. H. Puchtler, F. Sweat and M. Levine, J. Histochem. Cytochem. 10, 355 (1962).

12. M. T. Elghetany and A. Saleem, Stain Tech. 63, 201 (1988).

13. Polyclonal antibody against β/A4 1–40 (gift of Dr. C. Masters) was used at a dilution of 1:400 for light microscopy and 1:500 for immunogold labelling as described in A. D. Snow et al., Am. J. Path. 133, 456 (1988). Polyclonal antibody against β/A4 1–28 (gift of Dr. D. Selkoe) was used at a dilution of 1:250.

14. HK-249 is a rat monoclonal antibody (used as undiluted hybridoma supernatant) which recognizes a glucosamine sulfate alpha 1 4 glucuronic acid determinant on HS GAGs as previously described in Y. Koike et al., IX International Symposium on Glycoconjugates, B8, abstract, 1987; A. D. Snow et al., Am. J. Path. 137, 1253 (1990);

15. HK-102 is a rat monoclonal antibody, used as undiluted hybridoma supernatant as previously described in M. Kato et al., J. Cell Biol. 106, 2203, 1988.

16. Since HK-102 and HK-249 are monoclonal antibodies made in rat, they do not recognize endogenous HSPGs in normal rat brain. However, since we used a basement membrane HSPG derived from mouse cells (EHS sarcoma) for HSPG or HS infusion, these antibodies served as excellent markers for localization of infused HSPG or HS GAGs in this model.

17. One polyclonal antibody was a gift from Dr. J. Hassell (J. R. Hassell et al, Proc. Natl. Acad. Sci. 77, 4494 (1980)). The other polyclonal antibody was raised in a rabbit by injecting the perlecan antigen into popliteal lymph node. The perlecan antigen was prepared as described in reference #6, and no contamination by other macromolecules was confirmed as described in reference #6.

18. Alz-50 antibody (gift of Dr. P. Davies) was used at an optimal dilution of 1:200. B. L. Wolozin et al., Science 232, 648 (1986); B. Wolozin and P. Davies, Ann. Neurol. 22, 521 (1987); B. T. Hyman et al., ibid 23, 371 (1988).

19. T. Yamamoto and A. Hirano, Neuropath. Appl. Neurobiol. 12, 3 (1986).

20. AA amyloid polyclonal antibody (gift of Dr. R. Kisilevsky) was used at a dilution of 1:20. R. Kisilevsky et al., Lab. Invest. 37, 544 (1977).

21. Two investigators blindly scored an average of 3–5 slides per stain/immunostain per animal in order to quantitate possible differences between the various infusion groups. Approximately every 10th 6 μm serial section was identically stained or immunostained to allow for an assessment spanning the entire infusion area. Four animals per infusion group were scored with the exception of the saline and acetonitrile group where two animals were scored. Immunostaining with antibodies to β/A4 (1–40), HS GAGs (HK-249), HSPG core protein, Alz-50 and ED1 were all scored at the area adjacent to the infusion site (at magnifications of 25X and 100X). Congo red and thioflavin S staining was also evaluated at the areas adjacent to the infusion site (at a magnification of 100X). Scoring for staining/immunostaining was as follows: 0=negative; 1=slightly positive; 2=moderately positive; 3=strongly positive; Both staining/immunostaining intensity and the extent of staining/immunostaining adjacent to the infusion area were taken into account for scoring. Quantitation of the number of Bielchowsky silver positive neurons in the hippocampus was scored at a magnification of 25X and 100X. Neurons were identified by Nissl staining on adjacent serial sections. All measures except Bielchowsky stained cells were statistically analyzed using nonparametric tests (Kruskal-Wallis test for overall effects followed by Wilcoxon-Mann-Whitney test for individual group comparisons). For Bielchowsky stained cells, ANOVA was followed by Newman-Keul's test for individual group comparisons.

22. M. T. Elghetany and A. Saleem, Stain Tech. 63, 201 (1988).

23. H. M. Wisniewski et al., Acta Neuropath. 78, 22 (1989).

24. T. Suennaga et al., Acta Neuropath. 80, 280 (1990).

25. T. I. Mandybur and C. C. Chuirazzi, Neurology 40, 635 (1990); H. M. Wisniewski and J. Weigel, Neurobiol. Aging 12, 593 (1991); V. K. Vijayan et al., Exp. Neurol. 112, 72 (1991); R. C. A. Frederickson, Neurobiol. Aging 13, 239 (1992).

II. Detailed Description of the Animal Model of β/A4 Amyloid Deposition.

The following is a detailed description of the animal model of rapid β/A4 amyloid in brain.

Detailed Description of Surgical Procedure

The surgical procedure is modified from the method of Vahlsing et al. (1989). These authors demonstrated that the linings of the osmotic mini-pumps impart neurotoxins to the infusate. One key feature of their method and the present modification is that solutions infused into the brain are contained within the vinyl tubing connecting the pump to the cannula, and never contact solutions that are contained within the mini-pump chambers.

For all experiments 3 month male Sprague-Dawley rats are used. The night before surgery, model 2002 osmotic minipumps (Alzet Inc.) are filled with sterile saline colored with blue food coloring. A 5 cm length of V4 vinyl tubing (Bolab, Lake Havasu Ariz.) is attached to each pump and immersed in sterile saline at 37° C. If no blue fluid is in the tubing by the next morning, the pump is discarded. On the day of surgery, the rat is anesthetized with Nembutal (50 mg/kg), the skull and a small portion of the back just below the shoulder blades is shaved and washed with Betadine antiseptic. The rat is mounted in a stereotaxic apparatus and an incision is made down the middle of the skull.

Cannulae are constructed of 28 g stainless steel tubing, beveled at the tip, and bent twice at 90° angles (once medially and once posteriorly). The bends help anchor the tubing in the dental acrylic. The cannula is clamped onto the positioning arm of the micromanipulator via an extra piece of tubing attached to the cannula with Superglue, and the cannula is positioned over the hippocampus using bregma as reference point (AP −4.8; ML 3.5; DV 4).

Once the position of the cannula is determined, a burr hole several times larger than the size of the cannula is drilled. Two additional holes are then drilled for the insertion of small machine screws to act as anchors. A 5 cm length of V2 vinyl tubing is inserted into a 15 cm length of V4 vinyl tubing and sealed with Superglue gel. The V2 end of this tubing is then slid over the posterior end of the cannula and sealed with Superglue gel. A syringe is inserted into the V4 end of the tubing, the tip of the cannulae is placed into a 1.5 ml tube of 100% ethanol and the ethanol is rinsed through the inside of the entire cannula/tubing assembly to clean and sterilize the assembly. The cannula tip is next transferred to sterile saline solution to rinse out the ethanol, a small air bubble is drawn up into the tubing through the cannula (to act as a spacer, typically 1 cm in the V4 tubing, or 4 cm of the V2 tubing in length). Finally, the cannula is placed into the freshly prepared injectate and 100 μl of this solution is drawn into the cannula tubing assembly through the cannula.

The cannula is then repositioned over the hippocampus and slowly lowered into position. A dental acrylic plug is then formed around the cannula and anchoring screws. While the acrylic hardens, an incision of 2–4 cm is made in the animals shaved back just below the shoulder blades, and a subcutaneous pocket is formed by pulling up the skin with forceps and carefully snipping away any connective tissue between the skin and the body wall. A forceps is then be carefully slid up the back of the animal beneath the skin until it emerges at the back of the skull incision. The V4 tubing end is placed in the forceps and pulled through the subcutaneous passage. The location of the front of the air bubble is marked on the tubing with a black marking pen, and the tubing is cut about 3 cm behind this point in the portion filled with saline. The tubing is coiled into a circle 2–3 cm in diameter and the end looped through the coil (wrapped around it) to hold the coil in place. The minipump is attached to the end of the tubing. The tubing coil and pump is then inserted into the pocket formed subcutaneously in the back, and the incision closed with wound clips or sutures.

By this time, the acrylic will have cured adequately. The small piece of stainless steel tubing attaching the cannula to the micromanipulator arm is cut as close to the acrylic assembly on the skull as possible, and a small amount of wax (paraffin) is placed over the sharp point left by the cut tubing, and any rough edges of the acrylic assembly. The skin is pulled up and over the dental acrylic assembly and the incision closed with wound clips or suture, with care taken not to damage the vinyl tubing running out the back of the dental acrylic assembly.

Rats are placed in individual cages until recovery (1–2 hours) on isothermal pads to aid in body temperature regulation. Rats are typically active and vigorous the next day.

Detailed Description of Preparation of Infused Macromolecules for β/A4 Amyloid Deposition in Brain.

A detailed description of the solutions contained within the Alzet 2002 minipumps for delivery into brain is described. For best results, β/A4 (residues 1–40; Bachem Inc., Torrence, Calif.) is initially dissolved at 10 mg/ml in 35% acetonitrile (stock solution). Perlecan (basement membrane derived HSPG) is isolated from the mouse Engelbreth-Holm-Swarm sarcoma as described by Kato et al., J. Biol. Chem. 262, 7180 (1987). This particular HSPG has a $M_r$ of >700,000, is digestible with heparitinase yielding a core protein of $M_r$~400,000. The HSPG preparation showed no contamination by other macromolecules as determined by Alcian blue-silver staining as described in R. C. Krueger Jr. and N. B. Schwartz, Anal. Biochem. 167, 295 (1987). Perlecan can also be purchased from Collaborative Research Incorporated. Initial biochemical studies suggest that this commercial preparation contains both the low and high density forms of the HSPG, and further in vivo analysis are now underway to test this commercial preparation for its effectiveness in producing β/A4 amyloid deposition in brain, when co-infused with β/A4 (1–40). Perlecan should be dissolved in sterile saline at 5 mg/ml. For infusion studies, all reagents are dissolved and stored at 4° C. the night prior to surgery. Prior to placement of solution in os, otic pumps, 7.5 μl of β/A4 stock solution is mixed with 92.5 μl of HSPG stock solution (total volume=100 μl). The final concentration of acetonitrile is<than 3% when diluted as described above.

β/A4 amyloid deposition in brain may also occur with β/A4 (1–40) only, however the number of animals affected is variable in comparison to animals infused with β/A4 & HSPG. For β/A4 only infusion, β/A4 (1–40; Bachem Inc., Torrence, Calif.) is initially dissolved at 10 mg/ml in 35% acetonitrile (stock solution). Prior to placement in the osmotic pumps, 7.5 μl of β/A4 (stock solution) is mixed with 92.5 μl of sterile saline.

Alzet 2002 minipumps deliver the solutions described above at a flow rate of 0.5 ul/hour for one week. After one week of continuous infusion, rats are sacrificed by overdose with pentobarbital and perfused with 100 ml of saline followed by 150 ml of 4% paraformaldehyde buffered with phosphate (pH 7.4), postfixed for 24 hours and transferred to phosphate buffered saline for paraffin embedding. Once embedded, consecutive 6 μm serial sections were cut and placed on poly-D-lysine coated slides.

III. Heparin, Heparan Sulfate Glycosaminoglycans and Related Macromolecules as Potential Therapeutic Agents for Amyloid Deposition in Alzheimer's Disease Brain and Other Amyloidoses.

In vitro evidence is presented which demonstrates a high binding affinity between the basement membrane derived heparan sulfate proteoglycan (HSPG) (known as "perlecan") and β/A4 (residues 1–28). This binding interaction can be displaced by heparin, heparan sulfate glycosaminoglycans (GAGs) and related analogues suggesting potential in vivo intervention and potential therapeutic implications in patients containing excessive accumulation of β/A4 amyloid (i.e. patients with Alzheimer's disease). This is confirmed in vivo in an animal model of β/A4 amyloid deposition in brain, when inclusion of heparan sulfate GAGs in the β/A4 (1–40) infusate, abolishes congo red and thioflavin S staining indicative of loss of amyloid deposition and/or persistence in brain. In addition, since sequence analysis suggests that a putative heparin binding domain resides at residues 11–17 of β/A4 (Cardin and Weintraub, 1989), a potential inhibitor of HSPG-β/A4 binding and/or β/A4 amyloid deposition in brain may consist of a small 6 amino acid peptide having the sequence of -valine-histidine-histidine-glutamine-lysine-leucine-.

Background and Significance

Previous histochemical (Snow et al., 1989) and immunocytochemical (Snow et al., 1988a; 1990a) studies have demonstrated that a basement membrane derived heparan sulfate proteoglycan (HSPG) is specifically associated with the beta-amyloid protein (BAP) containing extracellular amyloid deposits in the brains of patients with Alzheimer's disease (AD). The BAP is a 39–43 amino acid peptide (Mr ~4,000)(Glenner and Wong, 1984; Wong et al., 1985; Masters et al., 1985) derived from a larger precursor molecule known as the beta-amyloid precursor protein (BAPP). Recent studies also indicate that a small dermatan sulfate proteoglycan (DSPG) is also associated with BAP-containing extracellular amyloid deposits (Snow et al., 1992). In addition, SDS-extracted amyloid cores derived from AD brain contain immunoreactivity for both HSPGs and DSPGs (Snow et al., 1990c). The apparent reasons for the co-association of these two specific PGs to amyloid deposits containing BAP is not known, but a specific binding interaction may be involved (Snow et al., 1989). Recent biochemical studies indicate that the basement membrane form of HSPG isolated from the Engelbreth-Holm-Swarm (EHS) sarcoma binds with high affinity to baculovirus-derived BAPPs (Narindrasorasak et al., 1991). However, it is not known whether HSPG or other PGs bind to the BAP region itself.

In the present study, we determined whether the extracellular domain of the BAP (residues 1–28) binds with differential affinities to PGs/GAG isolated from metabolically labeled endothelial cells (ECs) and smooth muscle cells (SMCs). We demonstrate that the extracellular domain of the BAP has both high and low affinity binding sites for a high $M_r$ HSPG derived from vascular ECs. In addition, two small DSPGs bind with low affinity, whereas a large chondroitin sulfate proteoglycan (CSPG) from SMCs, does not bind to BAP (1–28). These results indicate that specific classes of PGs interact with the extracellular domain of the BAP.

In-Vitro Studies: Abstract

Proteoglycans (PGs) are complex macromolecules which interact with a variety of other proteins and influence the processing, accumulation and function of these proteins in a variety of tissues. Both heparan sulfate (Snow et al., 1988. Am. J. Path. 133:456; Snow et al., 1990. Am. J. Path. 137:1253) and dermatan sulfate proteoglycans (Snow et al., 1992. J. Histochem. Cytochem. 40:105) co-localize to sites of extracellular amyloid deposits in the brains of patients with Alzheimer's disease (AD). However, the nature of these interactions is not understood nor is it clear whether different classes of PGs interact with the major protein component found in brain amyloid deposits, a 39–43 amino acid peptide termed the beta-amyloid protein (BAP). In the present study, we examined whether specific PGs bound to the extracellular domain of the BAP (residues 1–28). Firstly, pretreatment of splenic and liver tissue sections with a synthetic peptide to BAP (1–28) produced strong immunoreactivity with BAP antibodies at tissue sites enriched in heparan sulfate proteoglycans (HSPGs). The BAP immunoreactivity was partially removed by pretreatment of the sections with nitrous acid or heparitinase, but not by chondroitinase ABC, suggesting that heparan sulfate GAG chains are involved in BAP binding. Secondly, $^{35}$S-sulfate labeled PGs derived from cultured bovine aortic endothelial cells (ECs) and smooth muscle cells (SMCs) preferentially bound to an affinity column containing BAP (1–28), whereas virtually no binding was observed to affinity columns containing residues 410–429 of the beta-amyloid precursor protein or bovine serum albumin. Characterization of BAP bound and non-bound fractions eluted with a linear salt gradient revealed strong binding by a high $M_r$ HSPG ($M_r$~600,000–800,000), weak binding by two dermatan sulfate proteoglycans (DSPGs)($M_r$~120,000 and 220,000), and lack of binding by a large chondroitin sulfate proteoglycan (CSPG) of SMCs ($M_r$~1–2×10$^{-6}$). Binding of $^{125}$I-labeled HSPGs to the BAP was strongly inhibited by isolated basement membrane HSPG and to a lesser extent by heparin, but not by chondroitin-6-sulfate or unsulfated dextran sulfate. Heparitinase treated $^{125}$I-labeled HSPGs also bound to BAP (1–28) suggesting a HSPG core protein interaction. Finally, Scatchard analysis of the interaction of BAP (1–28) and high $M_r$ HSPGs isolated from ECs indicated high affinity ($K_d$=8.3× 10$^{-11}$ M) and low affinity ($K_d$=4.2×10$^{-8}$ M) binding sites for the BAP, with approximately 1 mole of HSPG binding 1.8 moles of BAP. These results indicate that specific classes of PGs differentially bind to the extracellular domain of the BAP which may play an important role in the abnormal accumulation of this particular peptide.

In Vitro Studies—Materials and Methods

Tissue Sections

Six micron sections of paraffin-embedded AA amyloidotic spleen and liver (gift of Dr. Robert Kisilevsky, Kingston, Canada) were used for the in situ binding studies. AA amyloid was induced in CBA/J female mice (6–8 weeks old) using amyloid enhancing factor and silver nitrate, as previously described (Axelrad et al., 1982; Snow and Kisilevsky, 1985).

A polyclonal antibody against the AA amyloid protein (used at dilutions of 1:10 and 1:100) (gift of Dr. Robert Kisilevsky, Kingston, Canada) was used for immunocytochemical identification and localization of AA amyloid protein. HSPG accumulation was detected using either 1) a monoclonal antibody (HK-249) (used as undiluted hybridoma supernatant) which recognizes a glucosamine sulfate alpha 1 - - - 4 glucuronic acid determinant in the glycosaminoglycan (GAG) chains of the basement membrane derived HSPG (Koike et al., 1987; Snow et al., 1990a) (gift of Dr. Koji Kimata, Aichi, Japan) or 2) a polyclonal antibody (used at dilutions of 1:10 and 1:50) against the protein core of the basement membrane derived HSPG (gift of Dr. John Hassell, Pittsburgh, U.S.A.) (Hassell et al., 1980). Detection of the BAP was accomplished using a polyclonal antibody against residues 1–28 of the BAP (used at dilutions of 1:100 and 1:250) (gift of Dr. Dennis Selkoe, Boston, U.S.A.) or a polyclonal antibody against residues 1–42 of the BAP (used at dilutions of 1:100 and 1:250) (gift of Dr. Colin Masters, Perth, Australia).

Immunostaining of tissue sections was accomplished using the avidin-biotin-immunoperoxidase method, employing the appropriate biotin-labeled secondary antibodies, followed by incubation with avidin-conjugated horseradish peroxidase complex (Vector Labs, Burlingame, Calif.). Peroxidase activity was produced by treatment with 3,3-diaminobenzidine as previously described (Snow et al., 1988a). For immunocytochemical staining, the primary antibody was used initially through a series of dilutions to obtain the best specificity with the least background staining. Only results using the optimal dilutions of primary antibody are reported.

Paraffin sections of mouse AA amyloidotic liver or spleen (obtained 4 days after initial AEF+silver nitrate induction) were treated overnight at 4° C. with a 0.3 mg/ml or 0.5 mg/ml solution of a peptide corresponding to the extracellular domain of BAP (residues 1–28 of BAP or residues 597–624 of BAPP) (Bachem Inc., Torrance, Calif.) in Tris-buffered saline (TBS). After 18 hours, non-bound BAP was removed by extensive washing in 4 changes of TBS. Bound-BAP was then detected by immunostaining tissue sections with either of two BAP polyclonal antibodies as described above. In order to demonstrate specificity of BAP binding to specific PG sites, tissue sections were also treated with GAG degrading enzymes prior to incubation with BAP peptide. These treatments included: 1) 0.50 units/ml of chondroitin ABC lyase (Seikagaku Kogyo Co. Ltd., through ICN Biomedicals) in 0.1M enriched Tris-acetate buffer (pH 8.0) at 37° C. for 6 hours (Saitoh et al., 1968), 2) a solution of 20% nitrous acid: 33% acetic acid (1:1, volume/volume) incubated at room temperature for 6 hours (Snow et al., 1987) and 3) 10 units/ml of heparinase I and heparitinase I (Sigma, St. Louis, Mo.) in 0.20M Tris-HCl buffer (pH 7.0) with 20 mM calcium acetate added, at 37° C. for 6 hours. All solutions contained protease inhibitors including 0.1M 6-aminohexanoic acid, 5 mM benzamidine, 5 mM phenyl-methanesulfonyl fluoride and 10 mM N-ethylmaleimide. The activity of the heparinase/heparitinase mixture was tested by treating tissue sections from AA amyloidotic spleen, which demonstrate positive heparan sulfate immunostaining in the perifollicular area (using HK-249), with the heparinase/heparitinase mixture. The activity of chondroitin ABC lyase was tested by treating tissue sections of meningeal vessels which demonstrate positive chondroitin sulfate immunostaining with MAB-941, a monoclonal antibody directed against the GAG chains of CSPG (Lark et al., 1988).

Preparation of Proteoglycans for Binding Assays

Cultures of ECs, isolated from calf thoracic aortas, and monkey (*Macaca nemestrina*) aortic SMCs, prepared and maintained as previously described (Wight and Hascall, 1983; Kinsella and Wight, 1986; 1988) were labeled near confluent density with 100 uCi/ml $^{35}$S-sulfate for 48 hours. For most experiments, PGs were purified from labeled media using a 1 ml DEAE-Sephacel column, followed by extensive washing with 8M urea buffer (8M urea in 50 mM Tris-HCl, pH 7.5, with 2.5 mM EDTA and 0.5% Triton X-100) containing 0.25M NaCl, and elution in the same buffer containing 3M NaCl (Kinsella and Wight, 1988a). Samples eluted were dialyzed against TBS with 0.1% Triton X-100 prior to affinity chromatography (see below).

HSPGs and DSPGs were also prepared separately from cultured ECs. For these preparations, cultured media extracts equilibrated in urea buffer containing 0.25M NaCl were applied to DEAE-Sephacel (5 ml) and 2 peaks of bound radioactivity were eluted with a linear gradient of 0.25–0.70M NaCl in urea buffer (total volume of 60 ml) (Kinsella and Wight, 1986). The first peak, which consists primarily of HSPGs (Kinsella and Wight, 1988a), and the second peak, which contains primarily DSPGs (Kinsella and Wight, 1988b) were pooled and concentrated by applying the diluted sample to an 0.6–0.8 ml DEAE-Sephacel mini-column. After washing the column with urea buffer, bound radioactivity was eluted with sequential washes of 8M urea buffer containing 3M NaCl. Recovery of applied radioactivity exceeded 90%. HSPGs were further purified by chondroitin ABC lyase digestion, followed by chromatography on a 1 ml DEAE-Sephacel column as described above. Essentially, all the radioactivity eluted in the bound fraction from this column was degraded by nitrous acid (see below). Greater than 95% of the labeled PGs isolated from the second peak was degraded with chondroitin ABC lyase (see below) indicating the presence of DS/CSPGs.

Cultured media derived HSPGs, purified low density HSPG isolated from the EHS sarcoma (gift of Dr. Koji Kimata, Aichi, Japan), and BAP (1–28) were all iodinated with $^{125}$-I by the chloramine T method as described by Lories et al. (1987). For all iodinations, labeled macromolecules were separated from unincorporated label by chromatography on PD-10 columns (Pharmacia-LKB) in 8M urea buffer, and rechromatographed on DEAE-Sephacel and dialyzed into TBS with 0.1% Triton X-100 prior to use. Iodinated high $M_r$ HSPGs ran as a single band just entering a 4–12% SDS-PAGE gel (see FIG. 6B, lane 1), which was completely degraded by nitrous acid (see FIG. 6B, lane 2). A Bio-Rad protein assay was used to determine the amount of core protein present in the labeled HSPGs, whereas the quantities of GAGs was determined by an Alcian blue dot blot assay (Seno et al., 1970).

Affinity Column Chromatography. 0.5 mg or 1.0 mg of ligands consisting of 1) BAP (1–28) (Bachem Inc., Torrance, Calif.), 2) a peptide corresponding to residues 410–429 of the BAPP (gift of Dr. Dennis Selkoe, Boston, U.S.A.) or 3) bovine serum albumin (BSA fraction V, Boehringer, Mannheim Biochemical) were dissolved initially in 400 µl of double distilled water to which was added an equal volume of 0.2M HEPES buffer (pH 7.5) containing 160 mM calcium chloride. The ligand solutions were added to 0.8–1.0 ml of Affi-gel 10 (Biorad, Richmond, Calif.) and coupling was allowed to proceed for 4 hours at 4° C., after which 1/10 volume of 1M ethanolamine (pH 8.0) was added and incubation continued for an additional 1–2 hours to block remaining unreacted ester groups. Gel coupled ligand was then transferred to Biorad Econo-columns and washed with TBS in 0.1% Triton-X 100. To assess the amount of bound ligand, soluble (nonbound) protein remaining in the wash buffer was assayed. The affinity columns coupled approximately 90% of ligand initially applied (i.e. 0.45 mg or 0.90 mg). $^{35}$S-sulfate labeled PGs isolated from the culture media (360,000 dpm) of ECs and SMCs were applied to Affi-gel 10 columns containing 1) BAP (residues 1–28), 2) BAPP (residues 410–429) or 3) Bovine serum albumin. The labeled PGs were allowed to interact with the affinity gel for 1 hour (preliminary experiments indicated maximum binding efficiency at 1 hour) and non-bound radiolabelled PGs were eluted with 25 ml of TBS+0.1% Triton X-100 (TBS-TX 100). Bound PGs were eluted with either a single-step gradient using 15 mls of 4M MgCl$_2$ in TBS-TX 100 or a linear gradient of 0 to 4M MgCl$_2$ in TBS-TX 100. In some experiments, columns were further eluted with 15 ml of 8M urea in 50 mM Tris-HCl (pH 7.5), with 0.5% Triton X-100 and 3M NaCl. The radioactivity per fraction was determined by scintillation counting. Most experiments were repeated a minimum of three times. Recoveries of applied radioactivity from the affinity columns ranged from 80–95%.

Characterization of Affinity Bound and Non-Bound Proteoglycans

Bound and non-bound PGs were resolved on 4–12% gradient SDS-PAGE slab gels (Lammeli, 1970) and enhanced for autoradiography with Enlightening (NEN, Boston, Mass.) before exposure at −70° C. on Kodak XAR-2 film. Some samples were digested with either 1) 0.50 units/ml of chondroitin ABC Lyase (Seikagaku Kogyo Co. Ltd., through ICN Biomedicals) in 0.1M enriched Tris-acetate buffer (pH 8.0) at 37° C. for 6 hours (Saito et al., 1968), or 2) 10 units/ml of heparinase I and heparitinase I (Sigma, St. Louis, Mo.) in 0.2M Tris-HCl buffer (pH 7.0) with 20 mM calcium acetate added, at 37° C. for 6 hours or 3) by deaminative cleavage with nitrous acid at pH 1.5 (Lindahl et al., 1973).

In order to test the specificity of HSPG binding to BAP (1–28), competitive inhibition experiments were also performed. $^{125}$-I labeled HSPGs (100,000–200,000 dpm) were mixed with (a) HSPG from EHS sarcoma ($M_r$ approximately 700,000) (Kato et al., 1988) (gift of Dr. Koji Kimata, Aichi, Japan), (b) heparin from porcine intestinal mucosa ($M_r$~11,000; Sigma, St. Louis, Mo.), (c) chondroitin-6-sulfate from shark cartilage ($M_r$~59,000; Sigma, St. Louis, Mo.), or (d) unsulfated dextran sulfate ($M_r$~110,000; Pharmacia Fine Chemicals, Uppsala, Sweden). The samples were incubated on a rotator for 2 hours at room temperature and then applied to the BAP (1–28) column. Columns were run and eluted with step gradients (1 to 4M $MgCl_2$) as described above.

Solid Phase Binding Assay $^{125}$I-HSPG (specific activity=1,104 cpm/ug) isolated from EC culture media was used to determine the amount of HSPG which bound to microtiter wells. Polyvinyl microtiter wells were coated with 100 $\mu$l of nitrocellulose solution (Schleicher and Schuell) (10 $cm^2$ of BA85 nitrocellulose in 10 ml of methanol) and allowed to dry at room temperature for 4 hours. Wells were coated overnight at room temperature with unlabeled HSPG to give 0.12 $\mu$g or 0.28 $\mu$g of bound HSPG per well, and blocked overnight at room temperature with 200 $\mu$l of 5% non-fat dried milk (Carnation Co., Los Angeles, Calif.). Various quantities of $^{125}$I-BAP (residues 1–28) (specific activity=6,683 cpm/pm) diluted in 100 $\mu$l of TBS/0.05% Tween 20 were added in triplicate to wells and incubated for 2.5 hours at room temperature on an orbital shaker. At the end of the incubation period, free $^{125}$I-BAP was then removed with 6 washes of TBS/0.05% Tween 20. Bound $^{125}$I-BAP was extracted from wells by incubation with 100 $\mu$l of 1N NaOH at room temperature for 1 hour, and "bound" versus "free" radioactivity was quantitated by liquid scintillation counting. Recovery of $^{125}$I-BAP as free and bound radioactivity exceeded 90%. A set of controls using 5% BSA-coated wells was also included in all experiments. In all cases, the binding of $^{125}$I-BAP to BSA was less than 5% of comparable binding to the HSPG.

In Vitro Studies—Results

In Situ Binding in Tissue Sections

The AA amyloidotic mouse model was used to determine whether the extracellular domain of the BAP (residues 1–28) bound to tissue sites enriched in HSPGs. As previously described (Snow et al., 1987; 1988b), four days after AEF+ silver nitrate treatment, large amounts of AA amyloid protein accumulated in the perifollicular area of the spleen (FIG. 4A, arrowheads). On adjacent serial sections, this tissue site contained HSPGs as demonstrated using a polyclonal antibody directed against the protein core (not shown) or a monoclonal antibody directed against an epitope on the GAG chains (FIG. 4B). As expected, little to no immunostaining of the same AA amyloidotic spleen was observed using polyclonal antibodies against residues 1–28 (FIG. 4C) or residues 1–42 (not shown) of BAP. However, pretreatment of tissue sections overnight at 4° C. with a synthetic BAP (residues 1–28) produced strong positive immunoreactivity with BAP antibodies at sites of HSPG accumulation (FIG. 4D).

In order to determine whether BAP immunoreactivity reflected the binding of BAP to tissue sites enriched in HSPGs, specific GAG-degrading enzymes or treatments were employed. AA amyloidotic tissue sections of spleen, pretreated with either acetic acid (used as a control for nitrous acid treatment, not shown) or chondroitin ABC lyase (FIG. 4E) showed little to no decrease in BAP immunostaining, whereas pretreatment with nitrous acid (FIG. 4F) or heparitinase/heparinase (not shown) prior to BAP peptide incubation, demonstrated some loss of BAP immunoreactivity (compare FIGS. 4F and 4D). The decrease in BAP immunostaining following pretreatment with nitrous acid or heparitinase/heparinase suggests that the binding of BAP peptide in the spleen is in tissues sites enriched in HSPGs. Similar results were observed in HSPG-positive sites in AA amyloidotic liver (not shown). In these tissues, BAP (1–28) binding was also localized throughout the lining of the sinusoids, a site normally enriched in EC HSPGs (Soroka and Farquhar, 1991).

Affinity Column Chromatography

As shown in FIG. 5 (top panel), 13.6% of $^{35}$S-sulfate labeled PGs isolated from ECs bound to the affinity column containing residues 1–28 of BAP and were subsequently removed with 4M $MgCl_2$. In contrast, when the same mixture of PGs were applied to an affinity column containing residues 410–429 of the BAPP, only 2.2% bound (FIG. 5, middle panel), whereas only 0.4% bound to the affinity column containing BSA (FIG. 5, bottom panel). Similarly, 12.5% of $^{35}$S-sulfate labeled PGs isolated from the culture media of SMCs also bound to BAP (1–28) column and were subsequently removed with 4M $MgCl_2$ (not shown).

SDS-PAGE was used to characterize the PGs which demonstrated affinity to the extracellular domain of the BAP. As shown in FIG. 6A, lane 1, the majority of non-bound EC PGs ran as a broad band with an apparent $M_r$ greater than 200,000, most of which was degraded by chondroitin ABC lyase (FIG. 6A, lane 2). This suggested that the unbound PGs primarily consisted of DS/CSPGs. The $^{35}$S-sulfate labeled EC PGs that were bound to the column containing residues 1–28 of BAP were separated into three distinct populations by SDS-PAGE (FIG. 6A, lane 3). One band just entered the gradient gel (apparent $M_r$>400,000) and was insensitive to chondroitin ABC lyase (FIG. 6A, lane 4). The two lower $M_r$ bands (approximately 220,000 and 120,000) (FIG. 6A, lane 3) were sensitive to chondroitin ABC lyase digestion (FIG. 6A, lane 4), consistent with their identification as small DS/CSPGs (Kinsella and Wight, 1988a).

Proteoglycans isolated from the culture media of SMCs were also tested for their ability to bind BAP (1–28). In comparison to EC PGs, SDS-PAGE analysis of the non-bound PG population from SMCs revealed a band present in the 3% stacking gel, a band just entering the gel (apparent $M_r$>400,000), and bands with apparent $M_r$ of ~200,000–300,000 and ~150,000 (FIG. 6B, lane 1). Chondroitin ABC lyase digestion removed the major band in the stacking gel, as well as the two bands just above and below the 200,000 Mr marker (FIG. 6B, lane 2). These results indicate that these bands contain CSPGs or DSPGs in agreement with previous studies (Chang et al., 1983; Schonherr et al., 1991).

The SMC PGs which bound to BAP (1–28) consisted primarily of a band just entering the gel, and broad bands above and below $M_r$ of ~200,000 (FIG. 6B, lane 3). These results indicate that 1) a similar high $M_r$ PG (just entering the gel) from both ECs and SMCs bind to BAP (1–28) (i.e. compare FIG. 6A, lane 4 and FIG. 6B, lane 4), and 2) a high $M_r$ CSPG present in SMCs does not bind to BAP (1–28) (FIG. 6B, lanes 1 versus 3).

To determine if there are differences in the relative binding affinities of these different labeled PGs for BAP (1–28), labeled culture media bound to BAP was eluted with a linear salt gradient of 0 to 4M $MgCl_2$. PGs (from ECs) that eluted with <1M $MgCl_2$ (FIG. 4A), contained three bands; a band just entering the gel and two lower $M_r$ bands of 150,000 and 200,000–300,000 (FIG. 7B, lane 1). With increasing concentrations of $MgCl_2$, SDS-PAGE revealed an increase in the proportion of the high $M_r$ band relative to the lower $M_r$ bands (FIG. 7B, lanes 2–4). The population of PGs that were present at the end of the salt gradient, when the column was further washed with 4M $MgCl_2$, consisted entirely of the high $M_r$ band (FIG. 7B, lane 4). These results indicate that although both a high $M_r$ (i.e. HSPG) and lower $M_r$ (i.e. DSPGs) PGs bind to BAP (1–28), the high $M_r$ PG elutes at higher salt concentrations suggesting that it binds with a higher affinity to BAP (1–28) than the lower $M_r$ PGs.

Figure 7C:
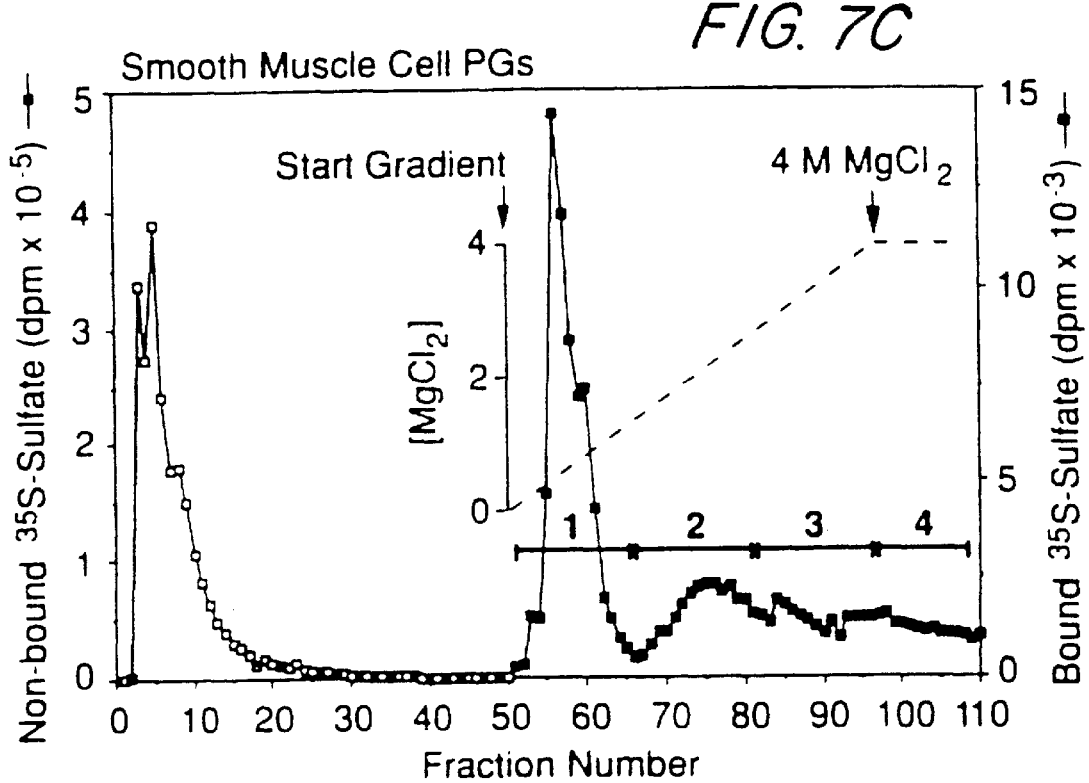

As shown in FIG. 7C, the majority of SMC PGs that bound to the BAP column eluted in one peak at the beginning of the salt gradient (<1M $MgCl_2$), indicating weak binding to BAP. The SMC PGs bound by BAP that were eluted with <1M $MgCl_2$, consisted of three bands; a band just entering the gel ($M_r$>400,000), a second band just above the 200 kDa marker and a faint band with an apparent $M_r$ of ~150,000 (FIG. 7D, lane 1). With increasing $MgCl_2$ concentrations, a relative increase in the proportion of the high $M_r$ band (just entering the gel) was observed. The population of PGs that were present at the end of the salt gradient, when the column was further washed with 4M $MgCl_2$, consisted entirely of the high $M_r$ band (FIG. 7D, lane 4).

Figure 8A:
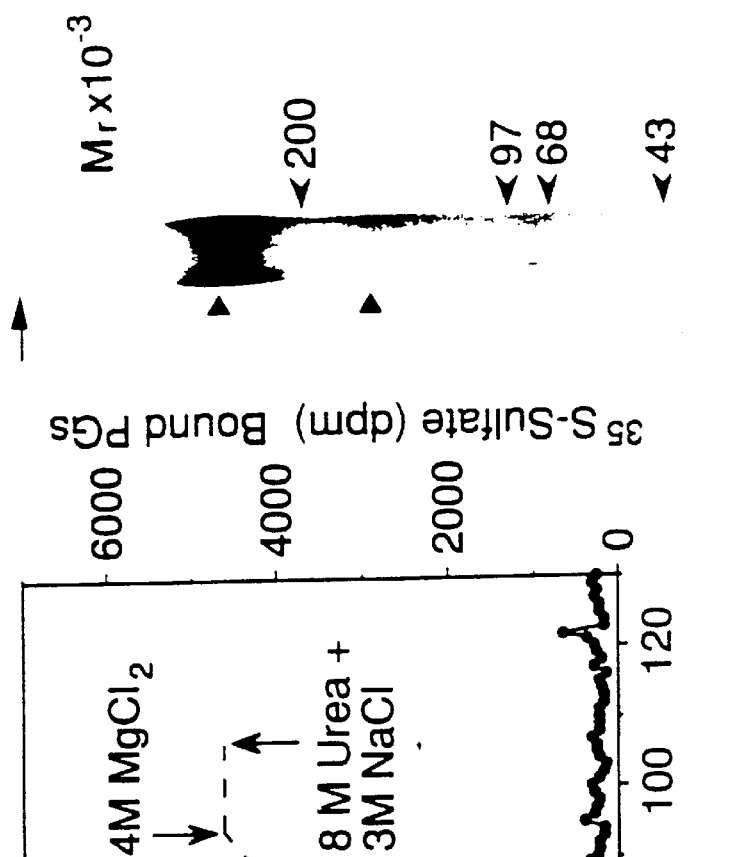
Figure 8B:
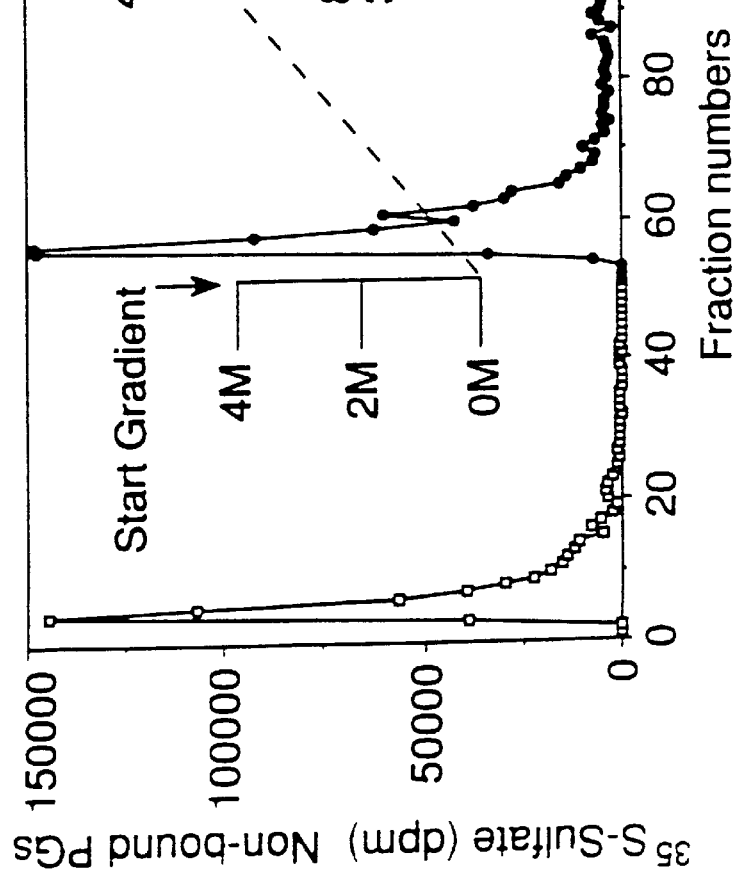

To confirm the identity of PGs which bind with different relative affinities to BAP (1–28), $^{35}$S-sulfate labeled HSPGs and DSPGs were isolated from the culture media of ECs and their binding affinities for BAP were compared. When isolated $^{35}$S-sulfate labeled DSPGs (FIG. 8B), which were sensitive to chondroitinase ABC but not degraded with nitrous acid (not shown), were applied to the BAP column, the majority of bound PGs eluted from the column at the beginning of the salt gradient (FIG. 8A). Little radioactivity was recovered at the end of the salt gradient, or after the column was washed with either 4M $MgCl_2$, followed by 8M Urea+3M NaCl.

On the other hand, isolated $^{35}$S-sulfate labeled high $M_r$ HSPG (FIG. 9B, lane 1) which was degradable with nitrous acid (confirming the presence of HSPG) (FIG. 9B, lane 2), bound tightly to the BAP column (FIG. 9A). Little radioactivity was recovered from the column during the 0 to 4M $MgCl_2$ linear gradient, or following further washing with 4M $MgCl_2$. The majority of bound HSPGs were eluted from the BAP column with 8M urea +3M NaCl (FIG. 9A), suggesting strong binding between the high $M_r$ HSPG and BAP.

Competitive Inhibition Studies

Purified iodinated HSPGs were combined with various concentrations of unlabeled competing ligands and applied to a BAP (1–28) affinity column (FIG. 10). In the absence of unlabeled competing ligand, 21.6+/−4.4% (n=5) of $^{125}$I-HSPG bound to the BAP column. EHS basement-membrane HSPG competed more effectively with $^{125}$I-HSPG for binding to BAP (<1.0 uM at 50% inhibition) than did heparin (10 uM at 50% inhibition) (FIG. 10).

Chondroitin-6-sulfate (at all concentrations except 100 uM) and unsulfated dextran sulfate (used at 12.3 uM) were unable to compete for the binding of $^{125}$I-labeled HSPG to BAP. The apparent competition by heparin for HSPG binding sites on the BAP column suggests that the heparan sulfate GAG chains are involved to some extent in the binding to BAP (1–28).

To assess whether the core protein of HSPG was also involved in binding to BAP (1–28), an aliquot of $^{125}$I-labeled HSPG was digested with a heparitinase/heparinase mixture (see methods) prior to affinity chromatography on the BAP column. In comparison to undigested controls, 61% of heparitinase-digested $^{125}$I-labeled HSPGs were still able to bind to the BAP column. These results suggest that the core protein of the high $M_r$ HSPG is important in binding to BAP (1–28).

Solid Phase Binding Assay

To quantitate the interaction between the high $M_r$ HSPG and BAP (1–28), 0.12 μg or 0.28 μg of the HSPG (isolated from the culture media of ECs; see FIG. 9B, lane 1) were immobilized on nitrocellulose coated wells and incubated with increasing concentrations of $^{125}$I-BAP. FIG. 11 shows the Scatchard analysis of the binding data from three experiments with wells coated with 0.28 μg of HSPG. Scatchard analysis indicated that both high affinity and low affinity binding sites exist on the high $M_r$ HSPGs. The $K_d$ of the high affinity binding site was $8.3 \times 10^{-11}$ M, whereas the $K_d$ of the low affinity binding site was $4.2 \times 10^{-8}$ M. Assuming molecular weights for the high $M_r$ HSPG and BAP of, 700,000 and 2,800, respectively, our data indicates that 1 mole of high $M_r$ HSPG bound 1.8 moles of BAP.

In Vitro and Binding Studies—Discussion

The present study used a variety of different experimental approaches to demonstrate that a ~600–800 kDa HSPG synthesized by vascular cells specifically binds with high affinity to the extracellular domain of the BAP. This HSPG was of the same approximate $M_r$ as the large HSPG produced by the EHS sarcoma in mouse (Kato et al., 1988). A similar HSPG has been shown to be synthesized by a number of different cell types including ECs (Oohira et al., 1983; Kinsella and Wight, 1988b; Lindblom et al., 1989; Saku and Furthmayr, 1989), fibroblasts (Stow and Farquhar, 1988; Heremans et al., 1990) and human colon carcinoma cells (Iozzo, 1984; Iozzo and Hassell, 1989). Additionally, antibodies against the core protein or GAG chains of a similar HSPG isolated from the EHS sarcoma immunolabel neurons (Snow et al., 1990a) and astrocytes (Snow et al., 1990a). The high $M_r$ HSPG has previously been referred to as the basement membrane derived HSPG (Hassell et al., 1980; Paulsson et al., 1987; Kato et al., 1988) although cells which do not produce basement membrane (i.e. fibroblasts) are also capable of synthesizing a similar HSPG (Stow and Farquhar, 1988; Heremans et al., 1990). The deduced amino acid sequence of the core protein is known from the analysis of corresponding cDNA sequences in both mouse (Noonan et al., 1988; 1991) and human (Iozzo et al., 1991; Kallunki and Tryggvason, 1992; Murdoch et al., 1992), and the gene for this HSPG is localized to chromosome 1 in both of these species (Wintle et al., 1990; Iozzo et al., 1991).

The present study demonstrates that both the GAG chains and the protein core of the high $M_r$ HSPG are involved in binding to the extracellular domain of the BAP. Evidence for the binding of heparan sulfate GAG chains to the BAP include partial removal of positive BAP immunoreactivity in tissues enriched in HSPG by pretreatment with nitrous acid or heparitinase/heparinase. Additionally, unlabeled heparin competitively inhibited binding of $^{125}$I-HSPG to BAP (see FIG. 7). Evidence for the HSPG core protein binding to the BAP (1–28) include a particularly high affinity constant (8.3×10-$^{11}$ M) for the high affinity binding site, consistent with protein-protein interaction, as well as the requirement of 8M urea +3M NaCl for elution of $^{35}$S-sulfate labeled HSPGs from the BAP affinity column. Additionally, intact low density EHS HSPG competed with $^{125}$I-HSPG for BAP binding more effectively than did heparin (FIG. 10). Persistent binding of heparitinase-digested $^{125}$I-labeled HSPGs to the BAP also indicated a core protein interaction.

A number of studies have previously demonstrated that the high $M_r$ HSPG is capable of binding to other macromolecules either via its protein core, GAG chains or both. For example, Carey et al. (1990) demonstrated that the high $M_r$ HSPG made by Schwann cells preferentially bound laminin via the GAG chains of the PG with a binding affinity constant ($K_d$) of 1.0×10-$_6$ M. Vigny et al. (1988) showed that the binding of the high $M_r$ HSPG (isolated from the EHS sarcoma) to basic fibroblast growth factor was primarily mediated by the heparan sulfate GAG chains with a $K_d$=3× 10-$^5$ M. On the other hand, Heremans et al. (1990) found that the high $M_r$ HSPG of human lung fibroblasts bound fibronectin via the core protein with a $K_d$=2×10-$^9$M.

In another investigation, Clement et al. (1989) demonstrated that the core protein of the high $M_r$ HSPG bound to proteins on the surface of hepatocytes, with these proteins primarily eluted from an HSPG-core protein affinity column with 1M NaCl. In comparison to the binding of the high $M_r$ HSPG to macromolecules reported in all these latter studies, the affinity of the large HSPG to the extracellular domain of the BAP is high (high affinity site: $K_d$=3×10-$^{11}$, low affinity site: $K_d$ 4.2×10-$^8$ M, and requires extremely high salt concentrations for elution of bound HSPGs from the BAP affinity column).

Although the precise binding site for HSPG on BAP (1–28) was not determined in the present study, residues 12–17 of BAP (-valine-histidine-histidineglutamine-lysine-leucine-) conform to a consensus sequence (—X—B—B—X—B—X— where B represents a basic residue and X represents a hydropathic residue) of a heparin/heparan sulfate binding domain in several proteins (Cardin and Weintraub, 1989). Since recent studies (Esch et al., 1990; Sisodia et al., 1990) also demonstrate that one of the putative cleavage sites in normal BAPP processing is located at positions 15–17 of the BAP, it is possible that the binding of the high $M_r$ HSPG within this region prevents normal proteolysis from occurring, leading to abnormal processing and eventual accumulation of the BAP fragment. A high $M_r$ HSPG synthesized by ECs has been shown to bind basic fibroblast growth factor and protect it from proteolytic degradation by the protease plasmin (Saksela et al., 1988). Similarly, heparan sulfate GAGs once bound to interferon-gamma protects interferon-gamma against protease attack (Lortat-Jacob and Grimaud, 1991).

Besides residues 12–17 of the BAP, other possible heparan sulfate binding domains may exist in the BAPP. Schubert et al. (1989) demonstrated that residues 176–186 of the BAPP (a region in the extracellular domain of the BAPP) binds to heparin Sapphires columns. Other potential heparan sulfate binding sites within the BAPP lie at residues 98–104 and 324–331 based on the consensus sequences of heparin binding domains (Cardin and Weintraub, 1989; Kisilevsky, 1989). In a more recent study (Narindrasorasak et al., 1991), the basement membrane form of HSPG isolated from the EHS sarcoma was analyzed for its binding properties to the entire 695, 751 and 770-amino acid BAPP proteins. Single binding sites for the HSPG on BAPP-695 ($K_d$=9×10-$^{10}$ M), BAPP-751 ($K_d$10×10-$^9$ M), and BAPP-770 ($K_d$=9×10-$^9$ M) were identified. However, the exact region of the binding sites on the BAPP molecules were not identified. The present study has now extended these initial observations using metabolically labeled PGs derived from vascular cells, and demonstrated that the BAP itself shows high affinity binding to a specific high $M_r$ HSPG.

The high $M_r$ HSPG once bound to BAP or BAPP, may actually induce a conformational change in the secondary structure of the BAP or BAPP. Previous studies have demonstrated that highly sulfated GAGs such as heparin (which is structurally similar to heparan sulfate) can influence the folding of mixed basic polypeptides to form a beta structure rather than an alpha helix. Additionally, heparan sulfate has been shown to significantly increase the beta-pleated sheet conformational structure in the AA amyloid (the major amyloid protein found in inflammation-associated amyloidosis) precursor, known as $SAA_2$.

The demonstration that vascular cells are capable of producing a high $M_r$ PG which binds tightly to the BAP has other implications. Since both ECs and SMCs are present in blood vessels in the brain, they represent a potential source of HSPG which accumulates in conjunction with BAP during cerebrovascular amyloid deposition (Snow et al., 1988a).

The present study also demonstrated a weak binding of two DSPGs to BAP (1–28). Vascular ECs and SMCs are known to synthesize two small DSPGs known as PG-I/biglycan ($M_r$~200,000–300,000) and PG-II/decorin ($M_r$~150,000) (Kinsella and Wight, 1988; Jarvelainen et al. , 1991). Recent studies using immunocytochemical probes against the core protein of PG-II/decorin suggest that decorin is primarily localized to the periphery of BAP-containing amyloid plaques in Alzheimer's brain (Snow et al., 1992). Additionally, SDS-extracted amyloid cores derived from the cortex of Alzheimer's brain remain immunoreactive with decorin antibodies (Snow et al., 1990c). The presence of decorin in the periphery of BAP-containing amyloid deposits and in SDS-extracted amyloid cores may also be due to its binding affinity for the extracellular domain of the BAP as determined by the present study.

In summary, a variety of methods have shown the specific high affinity binding of a high $M_r$ HSPG, and low affinity binding of two DSPGs, to the extracellular domain of the BAP. These studies reconfirm the concept that particular classes of PGs are capable of interacting with specific protein ligands. In the specific case of BAP-PG interactions, the high affinity binding of the HSPG to BAP raises the possibility that HSPGs may play an important role in abnormal BAPP processing, leading to the accumulation of the BAP fragment.

In Vitro Studies—Citations

Axelrad, M. A., R. Kisilevsky, J. Willmer, S. J. Chen, and M. Skinner. 1982. Further characterization of amyloid-enhancing factor. Lab. Invest. 47:139–146.

Balduyck, M., S. Laroui, C. Mizon, and J. Mizon. 1989. A proteoglycan related to the urinary trypsin inhibitor (UTI) links the two heavy chains of inter-alpha-trypsin inhibitor. Biol. Chem. 370:329–336.

Bernfield, M., and R. D. Sanderson. 1990. Syndecan, a developmentally regulated cell surface proteoglycan that binds extracellular matrix and growth factors. Phil. Trans. R. Soc. Lond. 327:171–186.

Brown, D. C., and K. G. Vogel. 1989. Characteristics of the vitro interaction of a small proteoglycan (PG II) of bovine tendon with type I collagen. Matrix 9:468–478.

Camejo, G., S. Olofsson, F. Lopez, P. Carlsson, and G. Bondjers. Identification of apo B-100 segments mediating the interaction of low density lipoproteins with arterial proteoglycans. Arteriosclerosis 8:368–377.

Cardin, A. D., C. J. Randall, N. Hirose, and R. L. Jackson. 1987. Physical-chemical interaction of heparin and human plasma low-density lipoproteins. Biochem. 26:5513–5518.

Cardin, A. D., and H. J. R. Weintraub. 1989. Molecular modeling of protein-glycosaminoglycan interactions. Arteriosc. 9:21–32.

Carey, D. J., D. M. Crumbling, R. C. Stahl, and D. M. Evans. 1990. Association of cell surface heparan sulfate proteoglycans of Schwann Cells with extracellular matrix proteins. J. Biol. Chem. 265:20627–20633.

Chang, J. Y. 1989. Binding of heparin to human antithrombin III activates selective chemical modification at lysine 236. J. Biol. Chem. 264:3111–3115.

Chang, Y., M. Yanagishita, V. C. Hascall, and T. N. Wight. 1983. Proteoglycans synthesized by smooth muscle cells derived from monkey (Macaca nemestrina) aorta. J. Biol. Chem. 258:5679–5688.

Cheifetz, S., and J. Massague. 1989. Transforming growth factor-beta (TGF-b) receptor proteoglycan. J. Biol. Chem. 264:12025–12028.

Clement, B., S. Bartolome, J. R. Hassell, G. R. Martin, and Y. Yamada. 1989. Identification of a cell surface-binding protein for the core protein of the basement membrane proteoglycan. J. Biol. Chem. 264:12467–12471.

Dodge, G. R., I. Kovalszky, M. Chu, J. R. Hassell, O. W. McBride, H. F. Yi, and R. V. Iozzo. 1991. Heparan sulfate proteoglycan of human colon: partial molecular cloning, cellular expression and mapping of the gene (HSPG2) to the short arm of human chromosome 1. Genomics 10:673–680.

Dow, K. E., R. J. Riopelle, and R. Kisilevsky. 1991. Domains of neuronal heparan sulphate proteoglycans involved in neurite growth on laminin. Cell Tissue Res. 265:345–351.

Esch, F. S., P. S. Keim, E. C. Beattie, R. W. Blancher, A. R. Culwell, T. Oltersdorf, D. McClure, and P. J. Ward. 1990. Cleavage of amyloid beta peptide during constitutive processing of its precursor. Science 248:1122–1124.

Glenner, G. G. and C. W. Wong. 1984. Alzheimer's disease: Initial report of the purification and characterization of a novel cerebrovascular amyloid protein. Biochem. Biophys. Res. Comm. 120:885–890.

Hassell, J. R., P. G. Robey, H. Barrach, J. Wilczek, S. I. Rennard, and G. R. Martin. 1980. Isolation of a heparan sulfate-containing proteoglycan from basement membrane. Proc. Natl. Acad. Sc. 77:4494–4498.

Heremans A, B. DeCock, J. J. Cassiman, H. Van Den Berghe, and G. David. 1990. The core protein of the matrix-associated heparan sulfate proteoglycan binds to fibronectin. J. Biol. Chem. 265:8716–8724.

Iozzo, R. V. 1984. Biosynthesis of heparan sulfate proteoglycan by human colon carcinoma cells and its localization at the cell surface. J. Cell Biol. 99:403–417.

Iozzo, R. V. and J. R. Hassell. 1989. Identification of the precursor protein for the heparan sulfate proteoglycan of human colon carcinoma cells and its post translational modifications. Arch. Biochem. Biophys. 269:239–249.

Jarvelainen, H. T., M. G. Kinsella, T. N. Wight, and L. J. Sandell. 1991. Differential expression of small chondroitin/dermatan sulfate proteoglycans, PG-I/biglycan and PG-II/decorin, by vascular smooth muscle and endothelial cells in culture. J. Biol. Chem. 266:23274–23281.

Kallunki, P., and K. Tryggvason. 1992. Human basement membrane heparan sulfate proteoglycan core protein: A 467-kD protein containing multiple domains resembling elements of the low density lipoprotein receptor, laminin, neural cell adhesion molecules, and epidermal growth factor. J. Cell Biol. 116:559–571.

Kato, M., Y. Koike, S. Suzuki, and K. Kimata. 1988. Basement membrane proteoglycan in various tissues: characterization using monoclonal antibodies to the Engelbreth-Holm-Swarm mouse tumor low density heparan sulfate proteoglycan. J. Cell Biol. 106:2203–2210.

Kinsella, M. G., and T. N. Wight. 1986. Modulation of sulfated proteoglycan synthesis by bovine aortic endothelial cells during migration. J. Cell Biol. 102:679–687.

Kinsella, M. G., and T. N. Wight. 1988a. Isolation and characterization of dermatan sulfate proteoglycans synthesized by cultured bovine aortic endothelial cells. J. Biol. Chem. 263:19222–19231.

Kinsella, M. G., and T. N. Wight. 1988b. Structural characterization of heparan sulfate proteoglycan subclasses isolated from bovine aortic endothelial cell cultures. Biochem. 27:2136–2144.

Kisilevsky, R. 1989. Glycosaminoglycans and amyloid proteins. In Cerebrovascular Diseases. M. D. Ginsberg and W. D. Dietrich, editors. Raven Press, New York, 223–229.

Koike, Y., M. Kato, S. Susuki, and K. Kimata. 1987. A monoclonal antibody against the heparan sulfate of EHS-tumor proteoglycan. IX International Symposium on Glycoconjugates, B8. Abstract.

Kokkonen, J. O., and P. T. Kovanen. 1987. Low-density-lipoprotein binding by mast-cell granules. Demonstration of binding of apolipoprotein B to heparin proteoglycan of exocytosed granules. Biochem. J. 241:583–589.

Lammeli, U. K. 1970. Cleavage of structural proteins during the assembly of the head of bacterio phage T4. Nature 227:680–685.

Lark, M. W., T. Yeo, H. Mar, S. Lara, I. Helrstrom, K. Helistrom, and T. N. Wight. 1988. Arterial chondroitin sulfate proteoglycan: localization with a monoclonal antibody. J. Histochem. Cytochem. 36:1211–1221.

LeBaron, R. G., A. Hook, J. D. Esko, S. Gay, and M. Hook. 1989. Binding of heparan sulfate to type V collagen. J. Biol. Chem. 264:7950–7956.

Linblom, A., I. Carlstedt, and L. Fransson. 1989. Identification of the core proteins in proteoglycans synthesized by vascular endothelial cells. Biochem. J. 261:145–153.

Lindahl, U., G. Backstrom, L. Jansson, and A. Hallen. 1973. Biosynthesis of heparin, II. Formation of sulfamino groups. J. Biol. Chem. 248:7234–7241.

Lindahl, U., and G. Pejler. 1987. Heparin-like polysaccharides in intra-and extravascular coagulation reactions. Acta Med. Scand. 715:139–144.

Lories, V., H. DeBoeck, G. David, J. Cassiman, and H. Van den Berghe. 1987. Heparan sulfate proteoglycans of human lung fibroblasts. Structural heterogeneity of the core proteins of the hydrophobic cell-associated forms. J. Biol. Chem. 262:854–859.

Lortat-Jacob, H., and J. Grimaud. 1991. Interferon-gamma binds to heparan sulfate by a cluster of amino acids located in the C-terminal part of the molecule. FEBS 280:152–154.

Masters, C. L., G. Simms, N. A. Weinman, G. Multhaup, B. L. McDonald, and K. Beyreuther. 1985. Amyloid plaque core protein in Alzheimer's disease and Down's syndrome. Proc. Natl. Acad. Sc. 82:4245–4249.

Narindrasorasak, S., D. Lowery, P. Gonzalez-DeWhitt, R. A. Poorman, B. Greenberg, and R. Kisilevsky. 1991. High affinity interactions between the Alzheimer's beta-amyloid precursor proteins an d the basement membrane form of heparan sulfate proteoglycan. J. Biol. Chem. 266:12878–12883.

Murdoch, A. D., G. R. Dodge, I. Cohen, R. S. Tuan, and R. V. Iozzo. 1992. Primary structure of the human heparan sulfate proteoglycan from basement membrane (HSPG2/perlecan): A chimeric molecule with multiple domains homologous to the low density lipoprotein receptor, laminin, neural cell adhesion molecules and epidermal growth factor. In Press, J. Biol. Chem.

Noonan, D. M., E. A. Horigan, S. R. Ledbetter, G. Vogeli, M. Sasaki, Y. Yamada, and J. R. Hassell. 1988. Identification of cDNA clones encoding different domains of the basement membrane heparan sulfate proteoglycan. J. Biol. Chem. 263:16379–16387.

Noonan, D. M., A. Fulle, P. Valente, S. Cai, E. Horigan, M. Sasaki, Y. Yamada, and J. R. Hassell. 1991. The complete sequence of perlecan, a basement membrane heparan sulfate proteoglycan, reveals extensive similarity with laminin A chain, low density lipoprotein-receptor, and the neural cell adhesion molecule. J. Biol. Chem. 266:22939–22947.

Oohira, A., T. N. Wight, and P. Borstein. 1983. Sulfated proteoglycans synthesized by vascular endothelial cells in culture. J. Biol. Chem. 258:2014–2021.

Pasternack, R. D., S. J. Hubbs, R. G. Caccese, R. L. Marks, J. M. Conaty, and G. Dipasquale. 1986. Interleukin-1 stimulates the secretion of proteoglycan and collagen-degrading proteases by rabbit articular chondrocytes. Clin. Immun. Immunopath. 41:351–367.

Paulsson, M., P. D. Yurchenco, G. C. Ruben, J. Engel, and R. Timpl. 1987. Structure of low density heparan sulfate proteoglycan isolated from a mouse tumor basement membrane. J. Mol. Biol. 197:297–313.

Rosenberg, R. D. 1985. Role of heparin and heparin-like molecules in thrombosis and atherosclerosis. Fed. Proc. 44:404–409.

Saito, H, T. Yamagata, and S. Suzuki. 1968. Enzymatic methods for the determination of small quantities of isomeric chondroitin sulfates. J. Biol. Chem. 243:1536–1542.

Saksela, O., D. Moscatelli, A. Sommer, and D. B. Rifkin. 1988. Endothelial cell-derived heparan sulfate binds basic fibroblast growth factor and protects it from proteolytic degradation. J. Cell Biol. 107:743–751.

Sauvage, F. and Octave, J. N. Science 245:651, 1989.

Saksela, O., and D. B. Rifkin. 1990. Release of basic fibroblast growth factor-heparan sulfate complexes from endothelial cells by plasminogen activator-mediated proteolytic activity. J. Cell Biol. 110:767–775.

Schmidt, G., H. Robenek, B. Harrach, J. Glossl, V. Nolte, H. Hormann, H. Ritcher, and H. Kresse. 1987. Interaction of small dermatan sulfate proteoglycan from fibroblasts with fibronectin. J. Cell Biol. 104:1683–1691.

Schonherr, E., H. T. Jarvelainen, L. J. Sandell, and T. N. Wight. 1991. Effects of platelet-derived growth factor and transforming growth factor-beta1 on the synthesis of a large versican-like chondroitin sulfate proteoglycan by arterial smooth muscle cells. J. Biol. Chem. 266:17640–17647.

Schubert, D., R. Schroeder, M. Lacorbiere, T. Saitoh, and G. Cole. 1988. Amyloid beta protein precursor is possibly a heparan sulfate proteoglycan core protein. Science 241:223–226.

Schubert, D., M. Lacorbiere, T. Saitoh, and G. Cole. 1989. Characterization of an amyloid beta precursor protein that binds heparin and contains tyrosine sulfate. Proc. Natl. Acad. Sc. 86:2066–2069.

Scott, J. E. 1980. Collagen-proteoglycan interactions. Localization of proteoglycans in tendon by electron microscopy. Biochem. J. 187:887–891.

Scott, J. E., and M. Haigh. 1986. Proteoglycan-collagen interactions in intervertebral disc. A chondroitin sulphate proteoglycan associated with collagen fibrils in rabbit annulus fibrosis at the d-e bands. Biosc. Rep. 6:879–888.

Scott, J. E. 1991. Proteoglycan: collagen interactions in connective tissue. Ultrastructural, biochemical, functional and evolutionary aspects. Int. J. Biol. Macromol. 13:157–162.

Seno, N., K. Anno, K. Kondo, S. Nagase, and S. Saito. 1970. Improved method for electrophoretic separation and rapid quantitation of isomeric chondroitin sulfates on cellulose acetate strips. Anal. Biochem. 37;197–202.

Sisodia, S. S., E. H. Koo, K. Beyreuther, A. Unterbeck, and D. L. Price. 1990. Evidence that beta-amyloid protein in Alzheimer's disease is not derived by normal processing. Science 248:492–495.

Snow, A. D. and R. Kisilevsky. 1985. Temporal relationship between glycosaminoglycan accumulation and amyloid deposition during experimental amyloidosis. A histochemical study. Lab. Invest. 53:37–44.

Snow, A. D., R. Kisilevsky, C. Stephens, and T. Anastassiades. 1987. Characterization of tissue and plasma glycosaminoglycans during experimental AA amyloidosis and acute inflammation. Qualitative and quantitative analysis. Lab. Invest. 56:665–675.

Snow, A. D., H. Mar, D. Nochlin, K. Kimata, M. Kato, S. Suzuki, J. Hassell, and T. N. Wight. 1988a. The presence of heparan sulfate proteoglycans in the neuritic plaques and congophilic angiopathy in Alzheimer's disease. Am. J. Path. 133:456–463.

Snow, A. D., R. Kisilevsky, and T. N. Wight. 1988b. Immunolocalization of heparan sulfate proteoglycans to AA amyloid deposition sites in spleen and liver during experimental amyloidosis. In Amyloid and Amyloidosis. T. Isobe, S. Araki, F. Uchino, S. Kito and E. Tsubura, editors. Plenum Publishing Corp., New York, 87–93.

Snow, A. D., S. Lara, D. Nochl en, and T. N. Wight. 1989. Cationic dyes reveal proteoglycans structurally integrated within the characteristic lesions of Alzheimer's disease. Acta Neuropath. 78:113–123.

Snow, A. D., H. Mar, D. Nochlin, R. T. Sekiguchi, K. Kimata, Y. Koike, and T. N. Wight. 1990a. Early accumulation of heparan sulfate in neurons and in the beta-amyloid protein containing lesions of Alzheimer's disease and Down's syndrome. Am. J. Path. 137:1253–1270.

Snow, A. D. 1990c. The possible involvement of specific proteoglycans in the pathogenesis of Alzheimer's disease, Down's syndrome and other amyloidoses. In Aging of the Brain: Cellular and Molecular Aspects of Brain Aging and Alzheimer's Disease. T. Nagatsu, O. Hayaishi, editors. Japan Scientific Societies Press, Tokyo, 185–204.

Snow, A. D., H. Mar, D. Nochlin, H. Kresse, and T. N. Wight. 1992. Peripheral distribution of dermatan sulfate proteoglycans (decorin) in amyloid-containing plaques and their presence in neurofibrillary tangles of Alzheimer's disease. J. Histochem. Cytochem. 40:105–113.

Sommer A., and D. B. Rifkin. 1989. Interaction of heparin with human basic fibroblast growth factor: protection of the angiogenic protein from proteolytic degradation by a glycosaminoglycan. J. Cell Phys. 138:215–220.

Soroka, C. J., and M. G. Farquhar. 1991. Characterization of novel heparan sulfate proteoglycan found in the extracellular matrix of liver sinusoids and basement membranes. J. Cell Biol. 113:1231–1241.

Srinivasan, S. R., P. Vijayagopal, K. Eberle, E. R. Dalferes, B. Radhakrishnamuthy, and G. S. Berenson. 1988. Low density lipoprotein binding affinity of arterial wall isomeric chondroitin sulfate proteoglycans. Atherosclerosis 72:1–9.

Stow, J. L., and M. G. Farquhar. 1988. Distinctive populations of basement membrane and cell membrane heparan sulfate proteoglycans are produced by cultured cell lines. J. Cell Biol. 105:529–539.

Vallen, E. A., K. A. Eldridge, and L. A. Culp. 1988. Heparan sulfate proteoglycans in the substratum adhesion sites of human neuroblastoma cells: modulation of affinity binding to fibronectin. J. Cell Phys. 135:200–212.

Vigny, M., M. P. Ollier-Hartmann, M. Lavigne, N. Fayein, J. C. Jeanny, M. Laurent, and Y. Courtois. 1988. Specific binding of basic fibroblast growth factor to basement membrane-like structures and to purified heparan sulfate proteoglycan of the EHS tumor. J. Cell. Phys. 137:321–328.

Vogel, K. G., M. Paulsson, and D. Heinegard. 1984. Specific inhibition of type I and type II collage n fibrillogenesis by the small proteoglycan of tendon. Biochem. J. 223:587–597.

Weidemann, A., G. Konig, D. B unke, P. Fisher, J. M. Salbaum, C. L. Masters, and K. Beyreuther. 1989. Identification, biogenesis and localization of precursors of Alzheimer's disease A4 amyloid protein. Cell 57:115–126.

Wight, T. N., and V. C. Hascall. 1983. Proteoglycans in primate arteries. III. Characterization of the proteoglycans synthesized by arterial smooth muscle cells in culture. J Cell Biol. 96:167–176.

Wight, T. N., Cell biology of arterial proteoglycans. 1989. Arteriosclerosis 9:1–20.

Wight, T. N., D. K. Heinegard, and V. C. Hascall. 1991. Proteoglycans. Structure and function. In Cell Biology of Extracellular Matrix. E. D. Hay, editor. Plenum Press, New York, 45–78.

Wintle, R. F., R. Kisilevsky, D. Noonan, and A. M. V. Duncan. 1990. In situ hybridization to human chromosome 1 of a cDNA probe for the gene encoding the basement membrane heparan sulfate proteoglycan (HSPG). Cytogen. Cell Genet. 54:60–61.

Wong, C. W., V. Quaranta, and G. G. Glenner. 1985. Neuritic plaques and cerebrovascular amyloid in Alzheimer's disease are antigenetically related. Proc. Natl. Acad. Sc. 82:8729–8732.

Summary and Importance of In-Vitro Studies

The in vitro studies described above suggest that heparin and related highly sulfated GAGs (such as heparan sulfate or related analogues) and similar highly charged macromolecules (i.e. dextran sulfate) may be used as potential inhibitors of HSPG-β/A4 amyloid interactions. Inhibition of HSPG-β/A4 interaction may be a potential target therapy for β/A4 amyloid accumulation in vivo. In addition, a putative heparin binding domain within the β/A4 peptide having the sequence of -valine-histidinehistidine-glutamine-lysine-leucine-, which may be also used as a potential competitive agent for β/A4-HSPG interactions and ultimately to prevent the deposition and/or persistence of β/A4 amyloid in brain in patients with Alzheimer's disease.

In Vivo Studies Demonstrating Inhibition of β/A4 Amyloid Deposition in Brain by Heparan Sulfate Glycosaminoglycans The rapid animal model of β/A4 amyloid deposition in brain (described above) was used to assess the role of HSPG accumulation in β/A4 amyloid deposits and potential inhibition of deposition and/or β/A4 amyloid persistence by inclusion of highly sulfated GAGs such as heparan sulfate. Infusion of β/A4 (1–40) only into rat hippocampus demonstrate thioflavin S (FIG. 12, top left) and congo red staining (FIG. 12, top right) indicative of amyloid, only when endogenous brain HSPG accumulation occurs at these sites (FIG. 12, bottom). These observations suggest that endogenous brain HSPGs localize to infused β/A4 and/or fibrillar amyloid within 1 week of infusion.

Animals infused with β/A4 only demonstrated positive β/A4 immunostaining adjacent to the infusion site (FIG. 13, top), but were negative for congo red (FIG. 13, middle) and thioflavin S staining. Importantly, these animals were negative for endogenous HSPG immunostaining (FIG. 13, bottom) implying that HSPG accumulation at the β/A4 infusion site may be necessary for congo red staining and/or amyloid persistence in vivo.

Inhibition of fibrillar β/A4 amyloid deposition and/or its persistence in brain was demonstrated in animals infused with β/A4 & HS GAGs. Although immunostaining revealed both β/A4 (FIG. 14, top) and HS GAGs (FIG. 14, middle) were deposited adjacent to the infusion site, inclusion of HS GAGs in the infusate appeared to diminish or prevent congo red (FIG. 14, bottom) and thioflavin S staining indicative of amyloid. These observations imply that highly sulfated GAGs such as HS may prevent amyloid fibril assembly and/or its persistence in brain. Since previous data suggest that highly sulfated GAGs such as heparin are competitive inhibitors for β/A4 binding to HSPG (described above), it is feasible that HS GAG inclusion in the β/A4 infusate, may serve as a competitive inhibitor for β/A4 binding to endogenous brain HSPG. In addition, a 6 amino acid peptide to the putative heparin binding domain of β/A4, having the amino acid sequence of -valine-histidine-histidine-glutamine-lysine-leucine-, may theoretically also serve as a competitive inhibitor for β/A4 binding to HSPG, and therefore serve as a potential therapeutic agent.

These studies therefore imply that highly sulfated GAGs such as heparan sulfate, heparin and related analogues may have potential therapeutic value for β/A4 amyloid deposition in the brains of patients with AD. Potential inhibitors of HSPG-β/A4 amyloid interactions can be assayed in vitro using affinity column chromatography and solid phase binding assays (as described above). Potential inhibitors in vitro can then be tested in vivo using the rapid animal model of β/A4 amyloid deposition.

IV. New Animal Models of Amyloidosis

Based on the discovery that an animal model of β/A4 amyloidosis can be formed by the co-infusion of a specific amyloid protein (i.e. β/A4) in the presence of basement membrane derived heparan sulfate proteoglycan (i.e. "perlecan"), it is feasible that several other animal models of specific amyloidoses can be now be formulated using similar concepts. Below, other potential animal models addressing specific amyloidoses are described.

A New Animal Model of AA Amyloidosis

Previously, the only animal model of amyloidosis involved specifically the AA amyloid protein. This animal model of AA amyloidosis was derived by essentially two different methods. The first method involved daily subcutaneous injections of azocasein in mice (usually CBA/J mice) as described by Snow and Kisilevsky, 1985. In this model, AA amyloid accumulation initially occurs in the perifollicular area of the spleen at approximately 7 days after initial injection (i.e. day 1), followed by AA amyloid deposits in liver and kidney at 7–10 days. The other animal model of AA amyloidosis involved a single subcutaneous injection of 2% silver nitrate (the inflammatory agent) and a single tail vein injection of an extract known as amyloid enhancing factor (AEF) (Axelrad et al., 1982). In this latter model, AA amyloid deposition occurred rapidly in these animals, with the first appearance of AA amyloid in the perifollicular area of the spleen within 48 hours, followed by amyloid deposition in liver and kidney a few days later. In both these models, it has been clearly shown (Snow and Kisilevsky, 1985; Snow et al., 1991) that heparan sulfate proteoglycans (HSPGs) accumulate at the same time and in the same locales as the AA amyloid protein.

Since the entire sequence of AA amyloid protein is known in a variety of different animal species (Dwulet and Benson, 1987; Westermark et al., 1986; Gruys, 1984) the AA amyloid protein can be commercially synthesized in mg quantities. On the other hand, mg quantities of purified AA amyloid protein can be isolated from AA amyloid fibrils derived from animal tissues using the isolation method of Pras et al. (1968). Once the isolated AA amyloid protein is obtained, the new model of AA amyloidosis would involve one of the following methods:

1) AA amyloid protein is dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 $\mu$l of AA amyloid protein stock solution is mixed with 92.5 $\mu$l of perlecan stock solution (total volume=100 $\mu$l; for 1 week infusion).

2) The AA amyloid-perlecan mixture can then be either
   a) injected into the tail vein of mice or rats by daily injections or
   b) by using a 1 week (100 $\mu$l volume) or 2 week (200 $\mu$l volume) Alzet 2002 osmotic pump placed in the back of the animal (similar to the protocol used for $\beta$/A4 amyloid infusion -see page of patent) and infusing directly into the bloodstream by surgically positioning the cannulae into the bloodstream of the animal at one of a number of different sites (ex. through exterior jugular vein to superior vena cava) (Harmsand Ojeda, 1974).

3) Similarly for tail vein multiple injections, daily injections could consist of an initial injection of dissolved AA amyloid protein, followed by a tail vein injection of perlecan.

Controls should consist of animals that were either injected or infused with vehicle only. For all injection and/or infusion experiments, a dose response curve for either AA amyloid protein, perlecan, or the mixture of perlecan plus AA amyloid protein should be set up to determine the best dosage to be used in this animal model. Screening for fibrillar AA amyloid protein deposition and the best dosage response should be assessed as described below.

At the end of various time periods (i.e. 1 week, 2 weeks, 4 weeks etc.) each animal would be sacrificed and the organs (i.e. spleen, liver, kidney, heart, lungs and brain) would be analyzed by congo red staining (Puchtler et al., 1962) for deposition of fibrillar AA amyloid. Electron microscopy could be used to confirm fibrillar deposition at the ultrastructural level. Additionally, since good monoclonal and polyclonal commercially available antibodies are available which specifically recognize the AA amyloid protein, these can be used to screen the various organs also for AA amyloid protein deposition.

Axelrad, M. A., R. Kisilevsky, J. Willmer, S. J. Chen and M. Skinner. Further characterization of amyloid-enhancing factor. Lab. Invest. 47;139, 1982.

Dwulet, F. E. and M. D. Benson. Primary structure of amyloid fibril protein AA in azocasein-induced amyloidosis of CBA/J mice. J. Lab. Clin. Med. 110:322–329, 1987.

Gruys, P. R. H. E. Amyloid A proteins in different species. Appi. Path. 2:316–327, 1984.

Harms, P. G. and S. R. Ojeda. A rapid and simple procedure for chronic cannulation of the rat jugular vein. J. Appl. Physiol. 36:391–392, 1974.

Puchtler, H., F. Sweat and M. Levine. On the binding of congo red by amyloid. J. Histochem. Cytochem. 10:355–364, 1962.

Pras, M., M. Schubert, D. Zucker-Franklin, A Rimon and E. C. Franklin. The characterization of soluble amyloid prepared in water. J. Clin. Invest. 47:924–932, 1968.

Westermark, P., K. H. Johnson, G. T. Westermark, K. Sletten and D. W. Hayden. Bovine amyloid protein AA: isolation and amino acid sequence analysis. Comp. Biochem. Physiol. 85:609–614, 1986.

Snow, A. D. and R. Kisilevsky. Temporal relationship between glycosaminoglycan accumulation and amyloid deposition during experimental amyloidosis. A histochemical study. Lab. Invest. 53:37, 1985.

Snow, A. D., R. Bramson, H. Mar, T. N. Wight and R. Kisilevsky. A temporal and ultrastructural relationship between heparan sulfate proteoglycans and AA amyloid in experimental amyloidosis. J. Histochem Cytochem. 39:1321–1330, 1991.

A New Animal Model of AL Amyloidosis

Currently, there is no animal model available to study AL amyloidosis. Based on the $\beta$/A4 amyloid deposition model, an animal model of AL amyloidosis could also be formulated.

AL amyloid consists of the deposition of the variable region of immunoglobulin light chains, either lambda or kappa chains. In human conditions, the immunoglobulin light chains are deposited and found in the urine (referred to as "Bence Jones proteins"). Therefore, for this new animal model of AL amyloidosis, the variable region of Bence Jones proteins will be isolated from the urine (using the method of Eulitz et al., 1987) of different human patients who have developed AL amyloid deposition.

Since AL amyloid deposits in humans accumulate in most systemic organs (i.e. spleen. liver, kidney, heart, lung), a protocol for AL amyloidosis would involve the following:

1) Isolated Bence Jones proteins (referred to as "AL amyloid protein") is dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 $\mu$l of AL amyloid protein stock solution is mixed with 92.5 $\mu$l of perlecan stock solution (total volume=100 $\mu$l; for 1 week infusion).

2) The AL amyloid-perlecan mixture can then be either
   a) injected into the tail vein of mice or rats by daily injections or
   b) by using a 1 week (100 $\mu$l volume) or 2 week (200 $\mu$l volume) Alzet 2002 osmotic pump placed in the back of the animal (similar to the protocol used for $\beta$/A4 amyloid infusion and infusing directly into the bloodstream by surgically positioning the cannulae into the bloodstream of the animal at one of a number of different sites (ex. through exterior jugular vein to superior vena cava) (Harms and Ojeda, 1974).

3) Similarly for tail vein multiple injections, daily injections could consist of an initial injection of dissolved AL amyloid protein, followed by a tail vein injection of perlecan.

Controls should consist of animals that were either injected or infused with vehicle only. For all injection and/or infusion experiments, a dose response curve for either AL amyloid protein, perlecan, or the mixture of perlecan plus AL amyloid protein should be set up to determine the best dosage to be used in this animal model. Screening for fibrillar AL amyloid protein deposition and the best dosage response should be assessed as described below.

At the end of various time periods (i.e. 1 week, 2 weeks, 4 weeks etc.), each animal would be sacrificed and the organs (i.e. spleen, liver, kidney, heart, lungs and brain) would be analyzed by congo red staining (Puchtler et al., 1962) for deposition of fibrillar AL amyloid. Electron microscopy could be used to confirm fibrillar deposition at the ultrastructural level. Additionally, since good monoclonal and polyclonal commercially available antibodies are available which specifically recognize the AL amyloid protein, these can be used to screen the various organs also for AL amyloid protein deposition.

Eulitz, M., M. Breuer and R. P. Linke. Is the formation of AL-type amyloid promoted by structural peculiarities of immunoglobulin L-chains? Biol. Chem. 368:863–870, 1987.
Harms, P. G. and S. R. Ojeda. A rapid and simple procedure for chronic cannulation of the rat jugular vein. J. Appl. Physiol. 36:391–392, 1974.
Puchtler, H., F. Sweat and M. Levine. On the binding of congo red by amyloid. J. Histochem. Cytochem. 10:355–364, 1962.

A New Animal Model of Prealbumin/Transthyretin Amyloidosis

Currently, no animal model exists for prealbumin/transthyretin amyloid deposition in peripheral or autonomic nerve. However, since the prealbumin/transthyretin amino acid sequence is known (consisting of 127 amino acids) (Duan et al., 1989), mg quantities of normal prealbumin/transthyretin can be synthesized. Since single amino acid substitutions have been identified at position 30, 33, 60, 77, 84, 111 and 122 of the prealbumin/transthyretin molecule, these mutated prealbumin/transthyretin proteins could also be synthesized to be used to develop an appropriate animal models.

For this animal model, mg quantities of each of the mutated proteins and normal protein (as a control) should be used according to the following protocol:

1) Various normal and Mutated Prealbumin/transthyretin proteins are dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 $\mu$l of the prealbumin/transthyretin amyloid protein stock solution is mixed with 92.5 $\mu$l of perlecan stock solution (total volume=100 $\mu$l).

2) The prealbumin/transthyretin-perlecan mixture can then be either
   a) injected directly into the sciatic nerve, dorsal root ganglion or autonomic ganglion of mice or rats by daily injections, or
   b) by using a 1 week (100 $\mu$l volume) or 2 week (200 $\mu$l volume) Alzet 2002 osmotic pump placed in the back of the animal (similar to the protocol used for $\beta$/A4 amyloid infusion) and infusing within the area of either sciatic nerve, dorsal root ganglion or autonomic ganglion.

Controls should consist of animals that were either injected or infused with vehicle only. For all injection and/or infusion experiments, a dose response curve for either prealbumin/transthyretin protein, perlecan, or the mixture of perlecan plus prealbumin/transthyretin protein should be set up to determine the best dosage to be used in this animal model. Screening for fibrillar prealbumin/transthyretin amyloid protein deposition and the best dosage response should be assessed as described below.

At the end of various time periods (i.e. 1 week, 2 weeks, 4 weeks, etc.), each animal would be sacrificed and the peripheral nerves at the site of injection or infusion plus other systemic organs (i.e. spleen, liver, kidney, heart, lungs and brain) would be analyzed by congo red staining (Puchtler et al., 1962) for deposition of fibrillar prealbumin/transthyretin amyloid. Electron microscopy could be used to confirm fibrillar deposition at the ultrastructural level. Additionally, since good monoclonal and polyclonal commercial antibodies are available which specifically recognize prealbumin/transthyretin (ICN Immunobiologicals, p. 681, Prod. Number 68-218-1, 68-218-2, 68-218-3) these can be used to screen the various organs also for prealbumin/transthyretin protein deposition.

Duan, W., T. Cole and G. Schreiber. Cloning and nucleotide sequencing of transthyretin (prealbumin) cDNA from rat choroid plexus and liver. Nucl. Acids Res. 17:3979, 1989.
Puchtler, H., F. Sweat and M. Levine. On the binding of congo red by amyloid. J. Histochem. Cytochem. 10:355–364, 1962.

A New Animal Model of Beta$_2$-Microglobulin Amyloidosis

A large % of patients on long term hemodialysis develop carpal tunnel syndrome in which amyloid deposits containing beta$_2$-microglobulin are deposited. Additionally, beta$_2$microglobulin amyloid deposition is observed in the synovia of many joints. Since the complete amino acid sequence (100 amino acids) of the beta$_2$-microglobulin molecule is known, a new animal model of beta$_2$-microglobulin amyloidosis can be developed. For this new animal model, mg quantities of beta$_2$-microglobulin can be synthesized commercially and used according to the following protocol:

1) Beta$_2$-microglobulin is dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 $\mu$l of the beta$_2$-microglobulin protein stock solution is mixed with 92.5 $\mu$l of perlecan stock solution (total volume=100 $\mu$l).

2) The beta$_2$-microglobulin-perlecan mixture can then be
   a) injected directly into the tendon or hind leg (adjacent to medial nerve) of mice or rats using daily injections, or
   b) by using a 1 week (100 $\mu$l volume) or 2 week (200 $\mu$l volume) Alzet 2002 osmotic pump placed in the back of the animal (similar to the protocol used for $\beta$/A4 amyloid infusion) and infusing within the area of tendon or medial nerve or
   c) by using a 1 week (100 $\mu$l volume) or 2 week (200 $\mu$l volume) Alzet 2002 osmotic pump placed in the back of the animal and infusing directly into the bloodstream by surgically positioning the cannulae into the bloodstream of the animal at one of a number of different sites (ex. through exterior jugular vein to superior vena cava) (Harms and Ojeda, 1974).

Controls should consist of animals that were either injected or infused with vehicle only. For all injection and/or infusion experiments, a dose response curve for either beta$_2$-microglobulin, perlecan, or the mixture of perlecan plus beta$_2$microglobulin should be set up to determine the best dosage to be used in this animal model. Screening for fibrillar beta$_2$-microglobulin containing amyloid protein deposition and the best dosage response should be assessed as described below.

At the end of various time periods (i.e. 1 week, 2 weeks, 4 weeks, etc.), each animal would be sacrificed and the tendon and/or nerve at the site of injection or infusion plus other systemic organs (i.e. spleen, liver, kidney, heart, lungs and brain) would be analyzed by congo red staining (Puchtler et al., 1962) for deposition of fibrillar beta$_2$-microglobulin amyloid. Electron microscopy could be used to confirm fibrillar deposition at the ultrastructural level. Additionally, since a good monoclonal commercially available (Sigma, p. 1117; Product Number M 7398) antibody is available which specifically recognize beta$_2$-microglobulin, it can be used to screen the various organs also for beta$_2$-microglobulin protein deposition.

Harms, P. G. and S. R. Ojeda. A rapid and simple procedure for chronic cannulation of the rat jugular vein. J. Appl. Physiol. 36:391–392, 1974.

Puchtler, H., F. Sweat and M. Levine. On the binding of congo red by amyloid. J. Histochem. Cytochem. 10:355–364, 1962.

New Animal Models for Endocrine Type Amyloidoses

Several forms of isolated amyloid associated with endocrine tumors have been described. The amyloid is derived from a portion of the normal hormonal product secreted (or prehormone synthesized) by the cells from which the tumor arises. A variant of calcitonin is found in the amyloid of medullary carcinoma of the thyroid, as well as in the Islets of Langerhans in the pancreas of patients with type-II (non-insulin) diabetes. Since the amino acid sequence for calcitonin is known φ, animal models for both these types of amyloidoses can be derived. For these new animal models, mg quantities of calcitonin can be synthesized commercially and used according to the following protocol:

1) Calcitonin is dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 µl of the calcitonin protein stock solution is mixed with 92.5 µl of perlecan stock solution (total volume=100 µl).

2) The calcitonin-perlecan mixture can then be
   a) injected directly into the thyroid gland or pancreas of mice or rats using a single bolus injection, or
   b) by using a 1 week (100 µl volume) or 2 week (200 µl volume) Alzet 2002 osmotic pump placed in the back of the animal (similar to the protocol used for β/A4 amyloid infusion) and infusing directly into the thyroid gland or pancreas or
   c) by using a 1 week (100 µl volume) or 2 week (200 µl volume) Alzet 2002 osmotic pump placed in the back of the animal and infusing directly into the bloodstream by surgically positioning the cannulae into the bloodstream of the animal at one of a number of different sites (ex. through exterior jugular vein to superior vena cava) (Harms and Ojeda, 1974).

Controls should consist of animals that were either injected or infsed with vehicle only. For all injection and/or infusion experiments, a dose response curve for either calcitonin, perlecan, or the mixture of perlecan plus calcitonin should be set up to determine the best dosage to be used in this animal model. Screening for fibrillar calcitonin containing amyloid protein deposition and the best dosage response should be assessed as described below.

At the end of various time periods (i.e. 1 week, 2 weeks, 4 weeks etc.), each animal would be sacrificed and the thyroid gland and/or pancreas plus other systemic organs (i.e. spleen, liver, kidney, heart, lungs and brain) would be analyzed by congo red staining (Puchtler et al., 1962) for deposition of fibrillar calcitonin amyloid. Electron microscopy could be used to confirm fibrillar deposition at the ultrastructural level. Additionally, since good monoclonal and polyclonal (ICN immunobiologicals; p. 646, Prod. Number 68-805-1; Sigma; p. 2139, Cat. Number C7669) commercially available antibodies are available which specifically recognize calcitonin, these can be used to screen the various organs also for calcitonin protein deposition.

Harms, P. G. and S. R. Ojeda. A rapid and simple procedure for chronic cannulation of the rat jugular vein. J. Appl. Physiol. 36:391–392, 1974.

Puchtler, H., F. Sweat and M. Levine. On the binding of congo red by amyloid. J. Histochem. Cytochem. 10:355–364, 1962.

A New Animal Model of PrP Protein Amyloidosis

The prion diseases consists of an amyloid protein containing a 27,000–30,000 MW variant protein known as the PrP protein. Since the amino acid sequence for PrP 27–30 is known, animal models for PrP protein amyloidoses can be derived. For this new animal model, mg quantities of PrP protein can be synthesized commercially and used according to the following protocol:

1) PrP 27–30 is dissolved in either distilled water or in an appropriate solvent (i.e. 35% acetonitrile) at a concentration of 10 mg/ml (stock solution). Isolated Perlecan is dissolved in either distilled water or sterile saline at 5 mg/ml. Prior, to administration 7.5 µl of the PrP protein stock solution is mixed with 92.5 µl of perlecan stock solution (total volume=100 µl).

2) The PrP protein-perlecan mixture can then be
   b) infused directly (stereotaxically) into hippocampus of rats by using a 1 week (100 µl volume) or 2 week (200 µl volume) Alzet 2002 osmotic pump placed in the back of the animal (similar to the protocol used for β/A4 amyloid infusion) and infusing directly into hippocampus Controls should consist of animals that were either injected or infused with vehicle only. For all injection and/or infusion experiments, a dose response curve for either PrP protein, perlecan, or the mixture of perlecan plus PrP protein should be set up to determine the best dosage to be used in this animal model. Screening for fibrillar PrP amyloid deposition and the best dosage response should be assessed as described below.

At the end of various time periods (i.e. 1 week, 2 weeks, 4 weeks etc.), each animal would be sacrificed and the brain plus other systemic organs (i.e. spleen, liver, kidney, heart, lungs and brain) would be analyzed by congo red staining (Puchtler et al., 1962) for deposition of fibrillar PrP amyloid. Electron microscopy could be used to confirm fibrillar deposition at the ultrastructural level. Additionally, since good monoclonal and polyclonal antibodies are available which specifically recognize PrP 27–30, these can be used to screen the various organs also for PrP protein deposition.

Puchtler, H., F. Sweat and M. Levine. On the binding of congo red by amyloid. J. Histochem. Cytochem. 10:355–364, 1962.

Portions of Perlecan Core Protein for Use in New Amyloidosis Models

In the different new animal models described above, we are infusing or injecting the entire perlecan macromolecule. However, once we identify the high affinity binding domain of perlecan (methodology described elsewhere in patent application) which binds to each of the different amyloid proteins described above, we can use peptide derived portions of the perlecan binding domain for infusion and/or injection in these animal models. Alternate administration routes are also envisioned, such as via implanted delivery devices, microspheres, and transdermal delivery.

Proteoglycans/Glycosaminoglycans and Their Unique Components as Inhibitors of Amyloidosis Proteoglycans consist of a linear protein core backbone to which one or more GAG chains are covalently linked (Hascall and Hascall, 1981). The highly anionic GAG chains consist of repeating disaccharide units, containing 1) hexosamine (either D-glucosamine or D-galactosamine) and 2) hexuronic acid (either D-glucuronic acid or L-iduronic acid). The PGs are traditionally named according to the identification of the primary GAG present and seven major GAGs have been identified. These are hyaluronic acid, chondroitin-4-sulfate, chondroitin-6-sulfate, dermatan sulfate, heparan sulfate, heparin and keratan sulfate.

Usually the linkage region between the GAG chains and the protein core backbone of the PG consists of a xylose-galactose-galactose binding region with the xylose molecule covalently linked to the hydroxyl groups of a serine residue on the protein core. The exception is hyaluronic acid which has a backbone consisting of alternating D-glucuronic acid and D-glucosamine units with no protein component. Keratan sulfate is the one PG which lacks the typical xylose-serine linkage. It is linked to protein either via a N-acetylgalactosamine residue to either serine or threonine (in cartilage) or via a N-acetylglucosamine residue linked directly to an asparagine residue (in cornea). Cloning and sequencing of the cDNA encoding the core protein of PGs indicate that Ser-Gly regions in the protein core of the PG are potential binding sites for GAG chains.

V. Heparin and Heparan Sulfate Glycosaminoglycans as Inhibitors of Amyloid Deposition, Formation and/or Persistence in Alzheimer's Disease and Other Amyloidoses

In Vivo Inhibition of β/A4 Amyloid Deposition and/or Persistence in Rat Infusion Model Using the rat infusion model, evidence in this patent application is presented which clearly shows that heparan sulfate GAGs (derived from the Engelbreth-Holm-Swarm sarcoma) are capable of in vivo inhibition of β/A4 congophilic and fibrillar deposition and/or persistence in brain (see FIG. 25 and FIG. 26). In addition, in vitro evidence suggests that heparin is capable of competing with heparan sulfate proteoglycan for binding sites on β/A4 (FIG. 10). Since heparin and heparan sulfate are GAGs with similar structural sequences (composed of 1–4 linked alternating residues of alpha-D-glucosamine and alpha-L-iduronic acid or β-D-glucuronic acid), these macromolecules or derivatives thereof, may be effective as modifiers or inhibitors of β/A4 amyloid formation, deposition and/or persistence, based on the evidence described above. Heparin has previously been shown to alter the synthesis and modify the sulfation pattern of HSPGs (Nader et al., 1989), and similarly may modify the accumulation of HSPGs in amyloid deposits in a variety of amyloidoses. In addition, heparin has been shown to bind to proteins and cause distinct changes in secondary structure as determined by circular dichroism spectroscopy (Brotherton et al., 1989). Therefore, this patent application proposes that heparin, non-anticoagulant heparin, and heparan sulfate GAGs and their individual constituents may act as modifiers of amyloid deposition, formation and/or persistence and therefore prove to be effective inhibitors of amyloidosis. These potential inhibitors therefore include:

1) intact heparin
2) non-anticoagulant heparins with various modifying substitutions such as periodate oxidation, borohydride reduction, N-deacetylation, carboxylreduction or combinations thereof
3) heparan sulfate GAGs obtained commercially
4) heparan sulfate GAGs isolated from EHS sarcoma
5) heparin and/or heparan sulfate disaccharides derived by actions of heparinase and/or heparitinase enzymes
6) heparin and/or heparan sulfate derived tetrasaccharides derived by actions of heparinase and/or heparitinase enzymes
7) heparin and/or heparan sulfate derived hexasaccharides derived by actions of heparinase and/or heparitinase enzymes
8) heparin and/or heparan sulfate derived octasaccharides derived by actions of heparinase and/or heparitinase enzymes
9) heparin and/or heparan sulfate derived decasaccharides, or decasaccharides derived by actions of heparinase and/or heparitinase enzymes (see Sigma Catalogue, p. 515 beparin saccharides)
10) heparin like substances such as mesoglycan (Sigma, p. 515, prod. number H 0519), sulodexide (Sigma, p. 515, prod. number H 1642)
11) individual constituents of heparin or heparan sulfate including structural sequences or modifications of D-glucosamine, iduronic acid or glucuronic acid.
12) dextran sulfates of various molecular weights (as described in Sigma catalogue p. 325)

Botherton, T. W., M. V. Jagannadham, and G. D. Ginder. Heparin binds to intact mononucleosomes and induces a novel unfolded structure. Biochem. 28:3518, 1989.

Hascall, V. C. and G. K. Hascall. Proteoglycans. In: Hay, E. D., ed., Cell Biology of the Extracellular matrix. New York, Plenum Press: 1981.

Nader, H. B., V. Buonassisi, P. Colbum, and C. P. Dietrich. Heparin stimulates the synthesis and modified the sulfation pattern of heparan sulfate proteoglycan from endothelial cells. J. Cell Physiol. 140:305–310, 1989.

Noonan, D. M., E. A. Horigan, S. R. Ledbetter, G. Vogeli, M. Sasaki, Y. Yamada and J. R. Hassell. Identification of cDNA clones encoding different domains of the basement membrane heparan sulfate proteoglycan. J. Biol. Chem. 263:16379–16387, 1988.

Identification of the Carbohydrate Moiety(s) Involved in β/A4 Binding

In order to determine the precise carbohydrate moiety(s) involved in β/A4 binding we will pass labeled heparin and/or heparan sulfate GAGs through different affinity columns containing β/A4 amyloid protein or regions thereof Non-bound and bound GAGs fractions will be collected and analyzed using a variety of LPLC and NMR methods for precise carbohydrate analysis. It is hoped that these studies will reveal which portion of specific GAG chains are responsible for binding to the β/A4 of Alzheimer's disease. This same technique will be used to analyze the specific GAG components involved in binding to other amyloid proteins, which can also then be used as inhibitors in other amyloidoses.

β/A4 Heparin Binding Domain Peptide as an Inhibitor of β/A4 Amyloidosis

As described above, residues 12–17 of the β/A4 (-valine-histidine histidine-glutamine-lysine-leucine-) SEQ ID NO: 3 conform to a consensus sequence for a potential heparin/heparan sulfate binding domain. This has been recently confirmed by our studies, whereby comparisons were made using column affinity chromatography. One affinity column contained β/A4 (1–28), whereas the other affinity column contained β/A4 (1–28) with three amino acid substitutions of the putative heparin binding domain (i.e., SEQ. ID. NO: 4 where the basic amino acids histidine, histidine and lysine where changed to glycine, and therefore were now uncharged instead of basic amino acids). $^{125}$I-HSPG bound with high affinity to normal β/A4 (1–28) affinity column, whereas a 50–60% decrease in HSPG binding to the mutated β/A4 (1–28) was observed. This study demonstrates that the -valine-histidine-histidine-glutamine-lysine-leucine SEQ ID NO: 3 sequence on β/A4 is a heparin/heparan sulfate binding region and that this 6 amino acid peptide may serve as a potential inhibitor of HSPG-β/A4 binding and therefore β/A4 amyloid accumulation, formation and/or persistence.

Other potential heparin binding domains within the amyloid precursor protein (APP) of Alzheimer's disease based on consensus sequences lie at residues 98–104 (SEQ. ID. NO. 5) 176–186 (SEQ. ID. NO. 6) and 324–331 (SEQ. ID. NO. 7) of APP and may also serve as potential peptide inhibitors of β/A4 amyloidosis.
Therefore, peptide inhibitors include:

1) residues 12–17 of β/A4 with sequence of -valine-histidine-histidine- glutamine-lysine-leucine SEQ ID NO. 3
2) residues 98–104 (SEQ. I.D. NO. 5) of APP with sequence of -cysteine-lysine-arginine-glycine-arginine-lysine-glycine
3) residues 324–331 (SEQ. I.D. NO. 7) of APP with sequence of -glutamic acid-alanine-lysine histidine-arginine-glutamic acid-arginine-methionine
4) Other potential heparin binding domains may also be determined in other amyloid proteins which have a cluster of basic amino acids or a consensus sequence of —X—B—B—X—B—X— where —X— represents an uncharged amino acid and —B— represents a basic amino acid residue (SEQ. ID NO: 8).

Heparan Sulfate Proteoglycan Core Protein Domain Peptides as Inhibitors of Amyloidosis.

Our studies suggest that perlecan synthesized by endothelial cells and smooth muscle cells binds with high affinity (High affinity binding site $K_d=^{83}\times10^{-11}$; low affinity binding site $K_d=4.2\times10^{-11}$) to the β/A4 (1–28). Although the binding of the high Mr HSPG appears to interact with β/A4 (1–28) via both the core protein (likely high affinity site) and GAG chains (likely low affinity site), we do not know which specific part of the large HSPG core protein is involved in high affinity binding. We will further determine the exact site on the HSPG core protein that is involved in β/A4 binding using the following methodology. Tryptic fragments of the HSPG core protein will initially be used as a means to inhibit binding of the isolated HSPG (from endothelial cells or from the EHS sarcoma) to the β/A4. For this latter procedure, the amyloidogenic peptide column will be pre-incubated with the tryptic fragment to be tested before loading the intact labeled PGs. If a particular tryptic fragment is effective in inhibiting PG binding, smaller fragments will be generated by further partial protease digestions (i.e. using chymotrypsin or V8 protease) (Noonan et al., 1988). When a small sub-fragment is found to still inhibit binding, and if enough material is obtained, it will then be sequenced. Once sequence is known, synthetic peptides to portions of this sub-fragment will be made and used in binding studies to determine the exact amino acid sequence involved in the binding interaction. Similar experiments can be done with different PG core proteins that may be implicated in binding to the β/A4 or other amyloid proteins present in other amyloidoses, as described above. Additionally, in collaboration, with Dr. Renato Iozzo, at Jefferson Medical University in Philadelphia, we will test HSPG core protein isolates to each of the five HSPG core protein domains obtained from fusion proteins. Therefore, other peptide inhibitors of β/A4 amyloidosis or other amyloidoses would include:

1) peptide core protein domains of perlecan which demonstrate strong binding to β/A4 and/or APP, or to other amyloid proteins.

Xylosides as Potential Inhibitors of Proteoglycan Accumulation in Amyloidoses Beta-D-xylosides, which serve as an exogenous acceptor for initiation of GAG chains thereby decreasing intact PG synthesis (Johnson and Keller, 1979; Kanwar et al., 1984; Schwartz et al., 1974; Scwartz, 1977), estradiol beta-D-xyloside which primarily inhibits heparan sulfate synthesis (Lagemwa and Esko, 1991), and chlorate, an inhibitor of GAG chain sulfation (Keller et al., 1989), could be used also as potential inhibitors of Proteoglycan accumulation in β/A4 amyloid and other amyloidoses. Since xylosides have previously been shown to alter specific classes of PGs differently (Johnson and Keller, 1979; Kanwar et al., 1984; Schwartz et al., 1974; Scwartz, 1977), initial experiments will be designed to determine which classes of PGs are affected. In these studies, we will use P19 cells, which are embryonal carcinoma cells which upon stimulation with 0.3 μm retinoic acid, differentiate primarily into cholinergic neurons. These cells during neuronal differentiation also demonstrate marked increases in APP message and protein levels, corresponding with changes in HSPG synthesis (Snow, unpublished data). In these experiments, dose response to a range of concentrations of $p-NO_2$-phenyl-Beta-D-xyloside (to 5 mM), estradiol beta-D-xyloside (to 5 mM), and chlorate (to 40 mM) of incorporation of radiosulfate into GAG will first be assayed by CPC precipitation in extracts from cell layers and media of stem cells (day 0) and differentiated neurons (day 9). Altered incorporation into specific PG species will be monitored by SDS-PAGE to establish whether different levels of inhibition result in differential effects on specific PG species. Alpha-D-xyloside, which cannot serve as a false acceptor, will be used as a control for effects of xyloside not attributable to altered GAG chain initiation (Johnson and Keller, 1979). Once we determine, which PGs/GAGs are primarily affected, experiments will focus on alterations on APP metabolism and expression. APP metabolism in cell lysates and medium will be monitored by pulse labelling with $^{35}$S-methionine followed by immunoprecipitation and Western blotting by specific BAPP antibodies. We will look for alterations in the size of BAPP products (indicating altered BAPP cleavage). Changes in both PG and BAPP expression will also be monitored during P19 differentiation (days 0, 4, 9, 13) using Northern blotting and slot blotting. We will also look for the deposition of the BAP in a fibrillar form (i.e. amyloid) by staining with the amyloid specific dyes, congo red (Puchtler et al., 1962) and thioflavin S (Elghetany, 1988). In addition, we will look for amyloid fibril formation in these cultures by transmission electron microscopy as previously described (Snow et al., 1988). It is conceivable that altered PG synthesis, may cause the aberrant accumulation of the BAP peptide, which may then aggregate into a fibrillar form (Kirschner et al., 1987). These studies will determine whether xyloside or modifications thereof could be used as inhibitors of PG/GAG accumulation, and therefore potential inhibitors of amyloid accumulation, formation and/or persistence.

Therefore, other potential inhibitors of β/A4 amyloidosis or other amyloidoses would include: 1) xylosides and modifications thereof, 2) estradiol β-D-xyloside; and 3) chlorate.

Elghetany, M. T., A. Saleem. Methods for staining amyloid in tissues: a review. Stain Tech 63:201–212, 1988.

Johnston, L. S., J. M. Keller. The effect of beta-xylosides on heparan sulfate synthesis by SV-transformed Swiss mouse 3T3 cell. J. Biol Chem 254:2575–2578, 1979.

Kanwar, Y. S., V. C. Hascall, M. L. Jakubowdki, J. T. Gibbons. Effect of beta-D-xyloside on the glomerular proteoglycans. I. Biochemical studies. J. Cell Biol 99:715–722, 1984.

Keller, K. M., P. R. Brauer and J. M. Keller. Modulation of cell surface heparan sulfate structure by growth of cells in the presence of chlorate. Biochem 28:8100–8107, 1989.

Kirschner, D. A., H. Inouye, L. K. Duffy, A. Sinclair, M. Lind, D. J. Selkoe. Synthetic peptide homologous to beta protein from Alzheimer's disease forms amyloid-like fibrils in vitro. Proc Natl Acad Sc 84:6953–6957, 1987.

Lugemwa, F. N., J. D. Esko. Estradiol beta-D-xyloside, an efficient primer for heparan sulfate biosynthesis. J. Biol Chem 266:6674–6677, 1991.

Puchtler, H., F. Sweat, M. Levine. On the binding of Congo red by amyloid. J. Histochem Cytochem 10:355–364, 1962.

Schwartz, N. B., L. Galligani, P. Ho, A. Dorfman. Stimulation of synthesis of free chondroitin sulfate chains by beta-D-xylosides in cultured cells. Proc Natl Acad Sc 71:4047–4051, 1974.

Schwartz, N. B. Regulation of chondroitin sulfate synthesis. Effect of beta-xylosides on synthesis of chondroitin sulfate proteoglycan, chondroitin sulfate chains, and core protein. J. Biol Chem 252:6316–6321, 1977.

Snow, A. D., H. Mar, D. Nochlin, K. Kimata, M. Kato, S. Suzuki, J. Hassell, T. N. Wight. The presence of heparan sulfate proteoglycans in the neuritic plaques and congophilic angiopathy in Alzheimer's disease. Am J. Path 133:456–463, 1988.

Testing of Glycosaminoglycans and Related Macromolecules as Potential Inhibitors of β/A4 Amyloid Deposition, Formation and/or Persistence Our data suggests that macromolecules that are able to inhibit HSPG-β/A4 amyloid binding have the potential of inhibiting β/A4 amyloid deposition and/or persistence in brain. Initial data also suggests that highly sulfated GAGs such as heparan sulfate and heparin are capable of serving as competitive inhibitors of HSPG-β/A4 amyloid binding.

In this study we will sequentially use in vitro and in vivo methods to determine which macromolecules may serve as potential inhibitors of β/A4 amyloid deposition, formation and/or persistence in brain. These same screening techniques will be used to screen other potential GAG-related or peptide inhibitors in other amyloidoses.

GAGs and Related Molecules as Potential Inhibitors of HSPG-β/A4 Binding.

STAGE 1-TESTING (FIG. 36)

Initial studies for screening will consist of determining which agents (i.e., GAGs, peptides) are capable of inhibiting HSPG-β/A4 binding. Three primary methods which we have utilized in the past will be used to screen potential inhibitors of HSPG-β/A4 binding (FIG. 36). Slot blot assays, affinity column chromatography (using β/A4 peptides coupled to Affi-gel 10 or 15) (methodology described above) and solid phase binding assays (using isolated HSPG on the solid phase) (methodology described above) will be used to test various potential inhibitors of HSPG-β/A4 peptide binding. Potential HS and heparin GAGs and their modifications, non-anticoagulant heparins or their modifications, as well as synthetic GAGs and related macromolecules, and potential inhibitor peptides (described above) will be used. Potential inhibitors discovered in this study will then be used to assess conformational effects of β/A4 peptides and/or isolated amyloid fibrils (described below).

GAGs and Related Molecules as Potential Inhibitors of β/A4 Folding into a Beta-Pleated Sheet Structure.

STAGE 2 TESTING (FIG. 37)

β/A4 peptides (1–28, 1–40) have the ability to self-aggregate and fold into a specific beta-pleated sheet conformation. Congo red staining demonstrating a red/green birefringence under polarized light is indicative of the beta-pleated sheet conformation of amyloid. In this study, we will test potential GAG inhibitors or peptides (described above) on their conformational effects of various β/A4 peptides (FIG. 37). In vitro tests will consist of congo red assays, consisting of combining the potential inhibitor with β/A4 (1–40), and staining aliquots air dried on slides with congo red (Puchtler et al., 1962). Inhibition of congo red staining will suggest that the inhibitor has altered the secondary structure (i.e. beta-pleated sheet) of the amyloid protein. Further analysis will include conformational changes as determined by electron microscopy and/or circular dichroism spectroscopy (Cascio et al., 1989; Barrow and Zagorski, 1991). This latter technique can determine specific changes in beta-sheet, alpha helix and random coil in a given peptide and/or protein.

Barrow, C. J., and M. G. Zagorski. Solution structures of beta peptide and its constituent fragments: relation to amyloid deposition. Science 253:179–182, 1991.

Cascio, M., P. A. Glazer, and B. A. Wallace. The secondary structure of human amyloid deposits as determined by circular dichroism spectroscopy. Biochem. Biophys. Res. Comm. 162:1162–1166, 1989.

Puchtler, H., F. Sweat, M. Levine. On the binding of Congo red by amyloid. J. Histochem Cytochem 10:355–364, 1962.

A Rapid Animal Model of Fibrillar β/A4 Amyloid Deposition in Brain: An In Vivo Screen for Potential Therapeutic Intervention or Agents for Alzheimer's Disease and Related Disorders.

We have developed probably the best rapid animal model of congophilic and fibrillar β/A4 amyloid deposition in brain. This model can be used to screen potential agents found promising in studies #1 and #2. Preliminary data now suggests that highly sulfated GAGs such as heparan sulfate and/or heparin may inhibit amyloid formation in this animal model, by serving as a direct competitor for binding to the β/A4. Highly sulfated GAGs or heparin derivatives may be tested for possible amyloid inhibition in this model. If a particular GAG or carbohydrate is found to inhibit amyloid deposition and/or its persistence in brain, then we may then be able to test it in Alzheimer's disease patients (once proving that this compound is not toxic in humans). At the University of Washington, ongoing clinical trials involving many Alzheimer and control patients are underway for other potential drugs, most of which have been unsuccessful.

STAGE 3 TESTING (FIG. 38)

Once promising inhibitors are determined by in vitro assays described above, we will use the rapid animal model of β/A4 amyloid deposition to determine the in vivo effects of promising macromolecules found in stages #1 and #2. In stage 3 testing (FIG. 38), these molecules will be given at the same time as the protocol for β/A4 amyloid deposition. Alternatively, these potential inhibitors may be given at a later time, after β/A4 amyloid has appeared in the brain to determine whether these potential compounds are able to get rid of β/A4 amyloid in brain once deposited over various periods of time. We will determine using congo red and thioflavin S staining for congophilic amyloid formation, deposition and/or persistence, as well as electron microscopy for evidence of fibrillar amyloid, whether these potential inhibitors have altered the formation, deposition and/or persistence of β/A4 amyloid in vivo.

Non-Toxicity of Potential Inhibitors

STAGE 4 TESTING (FIG. 39)

Once a potential inhibitor is determined by stages 1–3 described above, it will be tested in a variety of in vitro and in vivo studies for non-toxicity. Non-toxic inhibitors derived from these studies will be ready for use in human patients as described below.

Human Clinical Trials with Amyloid Inhibitors

STAGE 5 TESTING (FIG. 40)

Non-toxic inhibitors determined in stage 4 studies will then be implemented for use in human Alzheimer and normal aged control patients at the University of Washington Alzheimer's Disease Research Center for clinical studies. These studies will include short term cognitive studies where improvement in memory tests (i.e. mini-mental test, Boston naming test) will be determined in double blind studies. In addition, promising inhibitors in short term studies will also be used in longer term studies.

PGs/GAGs as Potential Biochemical Indicators of Amyloidosis in Alzheimer's Disease and Related Disorders Currently, many labs around the world are trying to find potential diagnostic markers which may aid in the diagnosis of Alzheimer's disease. Currently, confirmation of diagnosis is made at autopsy by obtaining a piece of brain tissue (usually hippocampus or frontal cortex) and analyzing for the presence of amyloid plaques, neurofibrillary tangles and/or cerebrovascular amyloid deposits. A potential diagnostic test in a living patients would be extremely valuable to the patient (for early treatment). Current data by our lab demonstrates that there are specific changes in levels of particular PGs/GAGs in the cerebrospinal fluid (CSF) of Alzheimer's patients versus controls (described below).

Glycosaminoglycans in the Cerebrospinal Fluid, Blood, and Urine

With no apparent specific biochemical test to detect patients who will develop AD, many investigators have been analyzing tissue fluids (i.e. CSF and plasma) from AD and normal aged controls to determine if a biochemical monitor of pathogenetic changes in AD exists. We have proposed testing the possibility that altered levels and/or types of GAGs/PGs in tissue fluids may serve as an indicator of GAG/PG and/or amyloid accumulation in the brains of AD patients. We have quantitated and identified GAGs present in the CSF of normal aged patients, providing the first evidence for the presence of GAGs in CSF (Snow et al., 1988). In our preliminary pilot study we determined hexuronic acid levels (a specific constituent and marker of GAGs) from the CSF obtained from 5 live normal aged controls to be 3.29+/−0.87 μg/ml. Additionally, preliminary evidence (Snow and Wight, unpublished data), using high voltage electrophoresis (Snow et al., 1987), suggests that both chondroitin sulfate and a highly sulfated form of heparan sulfate (in a ratio of 85% chondroitin sulfate and 15% heparan sulfate) are present in the CSF of both normal aged and AD patients. Preliminary data also suggests that changes in heparan sulfate and chondroitin sulfate in CSF occurs in Alzheimer's disease in comparison to other diseases and controls. These studies should provide useful information as to whether HS or other PG/GAG levels in the CSF reflect their level of accumulation in association with amyloid deposits in AD brain.

We have also found that the types of GAGs obtained from the lateral ventricles at autopsy (within 3–4 hours after death), where the diagnosis of AD is confirmed, are essentially the same (i.e. chondroitin sulfate and heparan sulfate) as those present in CSF fluid derived from live patients. This means that valuable data on the CSF GAG levels on confirmed cases of AD can be obtained with reliable accuracy. We are now routinely collecting the CSF from the lateral ventricles at autopsy (usually within 2–5 hours after death). Further studies are needed to evaluate the use CSF, plasma and/or urine GAGs as a potential biochemical marker of pathogenetic changes in AD. From an initial pilot study from 12 patients (7 AD and 5 controls) a proposed sample size of 36 subjects per group will be sufficient to detect a difference of 1.0 μg/ml (p<0.05). Whether PGs/GAGs can be used as potential biochemical indicators of pathogenetic changes in AD will be determined in this study.

We will determine the total levels and/or types of GAGs/PGs in the CSF of AD patients and normal aged controls, obtained in the living patient (i.e. spinal tap) and from the lateral ventricles at autopsy. In addition, we will determine total levels and/or types of GAGs/PGs in blood and urine from AD patients and normal aged controls. These studies will allow us to determine whether PG/GAG alterations occur in tissue fluids and whether changes in total levels and/or types of PGs/GAGs can be used as a potential biochemical indicator of pathogenetic changes in AD brain. In addition, we will determine these parameters in plasma and/or urine from the same patients to determine whether there is a correlation between levels and/or types of GAGs in the CSF, plasma and/or urine. A number of patients will also be followed during the course of the disease to determine if changes in types and/or quantities of GAGs in the CSF and/or blood correlate with severity of dementia in individual patients. The mini-mental test will be given to these patients at periodic intervals during the course of the disease to monitor changes in severity of dementia. Overall levels of GAGs will be determined by hexuronic acid analysis (Blumenkrantz and Asboe-Hansen, 1973). GAG recovery in each sample will be monitored by introducing 3H-labelled GAGs (approximately 100,000 dpm) in each sample at the beginning of the isolation procedure and the percent recovered determined from an aliquot at the end. GAG isolation and identification will be determined using high voltage electrophoresis and enzyme digestion followed by densitometry as previously described (Snow et al., 1987). In addition, CSF, plasma and/or urine samples (0.5 ml) will be put on DEAE nitrocellulose using a slot blot apparatus and various GAG and PG antibodies will be used to quantitate (using standard curves and scanning densitometry) different epitopes present in the CSF and/or plasma of AD versus normal aged patients. Immunostaining will be accomplished according to the PAP technique (Sternberger, 1986). Based on our initial pilot study using CSF obtained from 12 patients (7 AD and 5 controls), the proposed sample size of 36 subjects per group will be sufficient to detect a difference of 1.0 µg/ml ($p<0.05$).

Snow, A. D., M. Raskind and T. N. Wight. The potential significance for the presence of glycosaminoglycans in the cerebrospinal fluid of normal aged and Alzheimer's Patients. Alz. Dis. Assoc. Dis. 2 (3), p. 182, 1988. abstract.

Further Studies of a Rapid Animal Model of Fibrillar β/A4 Amyloid Deposition in Brain We will continually work on optimizing the rapid animal model of fibrillar β/A4 amyloid deposition in brain. We will optimize the procedure for β/A4 amyloid deposition, and determine the specificity of the reagents necessary for such deposition. These experiments will compare different β/A4 peptides, different components of the HSPG, and/or other PGs for their capacity to support congophilic amyloid formation. The optimal concentration of these agents and the minimum infusion period for amyloid formation will be determined. Detection of amyloid deposition will be evaluated by specific stains and immunocytochemical probes. Electron microscopy will determine the nature of the amyloid fibrils formed and their precise location.

We will also examine the long term anatomical and molecular consequences of β/A4 amyloid and/or PG deposition. A time course study ranging from 2 weeks to 1 year will be performed. Immunocytochemical, histological and in situ hybridization probes will be used to evaluate the capacity of β/A4 amyloid to induce changes in the host brain which resemble those of Alzheimer's Disease.

We will also examine the behavioral consequences of β/A4 amyloid and/or PG deposition in brain. Rats will be subjected to a behavioral test battery which will independently measure sensorimotor performance and learning and memory.

Success in these studies should provide additional and valuable information on the influence of β/A4 amyloid deposition on the structure, function and regulation of macromolecules within the brain. Additionally, it may provide a convenient means to assess the utility of novel therapeutic strategies designed to slow the rate of progression of Alzheimer's disease.

Citations

Abraham, C. R., D. J. Selkoe and H. Potter. Immunochemical identification of the serine protease inhibitor alphal-antichymotrypsin in the brain amyloid deposits of Alzheimer's disease. Cell 52:487–501, 1988.

Berenson, G. S., E. R. Dalferes, H. Ruitz and B. Radhakrishnamurthy. Changes of acid mucopolysaccharides in the heart involved by amyloidosis. Am J. Cardiol 24:358–364, 1969.

Bitter, T. and H. Muir. Mucopolysaccharides in amyloidosis. Lancet 1:819, 1965.

Bitter, T. and H. Muir. Mucopolysaccharides of whole human spleens in generalized amyloidosis. J. Clin Invest 45:963–975, 1966.

Camejo, G. The interaction of lipids and lipoproteins with the intercellular matrix of arterial tissue: its possible role in atherogenesis. Adv Lipid Res 19:1–53, 1982.

Castano, E. M., J. Ghiso, F. Prelli, P. D. Gorevic, A. Migheli and B. Frangione. In vitro formation of amyloid fibrils from two synthetic peptides of different lengths homologous to Alzheimer's disease beta-protein. Biochem Biophys Res Comm 141:782–789, 1986.

Conners, L. H., T. Shirahama, M. Skinner, A. Fenves and A. S. Cohen. In vitro formation of amyloid fibrils from intact beta2-microglobulin. Biochem Biophys Res Comm 131:1063–1068, 1985.

Dalferes, E. R., B. Radhakrishnamurthy and G. S. Berenson. Acid mucopolysaccharides of amyloid tissue. Arch Biochem Biophys 118:284–291, 1967.

Dalferes, E. R., B. Radhakrishnamurthy and G. S. Berenson. Glycosaminoglycans in experimental amyloidosis. Proc Soc Exp Biol Med 127:925–929, 1968.

Franklin, E. C. and D. Zucker-Franklin. Current concepts of amyloid. Adv Immun 15:249–304, 1972.

Friedrich, N. and A. Kekule. Zur amyloidfrage. Virch Arch Path Anat Physiol 16:50, 1859.

Gelman, R. A. and J. Blackwell. Heparin-polypeptide interactions in aqueous solution. Arch Biochem Biophys 159:427–433, 1973.

Gelman, R. A. and J. Blackwell. Interactions between mucopolysaccharides and cationic polypeptides in aqueous solution: chondroitin-4-sulfate and dermatan sulfate. Biopolymers 12:1959–1974, 1974.

Gelman, R. A. and J. Blackwell. Interactions between mucopolysaccharides and cationic polypeptides in aqueous solution: hyaluronic acid, heparan sulfate and keratan sulfate. Biopolymers 13:139–156, 1974.

Gelman, R. A. and J. Blackwell. Interactions of an intact proteoglycan and its fragments with basic homopolypeptides in dilute aqueous solution. Biochem J 141:445–454, 1974.

Glenner, G. G., D. Ein, E. D. Eanes, H. A. Bladen, W. Terry and D. L. Page. Creation of "amyloid" fibrils from Bence Jones proteins in vitro. Science 174:712–714, 1971.

Glenner, G. G. and D. L. Page. Amyloid, amyloidosis and amyloidogenesis. Int Rev Exp Path 15:1–92, 1976.

Gorevic, P. D., F. Gomi, B. Pons-Estel, F. Alvarez, N. S. Peress and B. Frangione. Isolation and partial characterization of neurofibrillary tangles and amyloid plaque core in Alzheimer's disease: immunohistological studies. J Neuropath Exp Neurol 45:647–664, 1986.

Gorevic, P. D., E. M. Castano, R. Sarma and B. Frangione. Ten to fourteen residue peptides of Alzheimer's disease protein are sufficient for amyloid fibril formation and its characteristic x-ray diffraction pattern. Biochem Biophys Res Comm 147:854–862, 1987.

Iqbal, K., T. Zaidi, C. H. Thompson, P. A. Merz and H. M. Wisniewski. Alzheimer paired helical filaments: bulk isolation, solubility and protein composition. Acta Neuropath 62:167–177, 1984.

Kirschner, D. A., H. Inouye, L. K. Duffy, A. Sinclair, M. Lind and D. J. Selkoe. Synthetic peptide homologous to beta protein from Alzheimer's disease forms amyloid-like fibrils in vitro. Proc Natl Acad Sc 84:6953–6957, 1987.

Mowry. R. W. and J. E. Scott. Observations on the basophilia of amyloids. Histochemie 10:8–32, 1967.

Okuyara, T. and K. Turumi. Acid mucopolysaccharides from a spleen of primary amyloidosis. Clin Chim Acta 8:140–142, 1963.

Pennock, C. A. Association of acid mucopolysaccharides with isolated amyloid fibrils. Nature 217:753–754, 1968.

Pennock, C. A., J. Burns and G. Massarella. Histochemical investigation of acid mucosubstances in secondary amyloidosis. J Clin Path 21:578–581, 1968.

Saksela, O., D. Moscatelli, A. Sommer and D. B. Rifkin. Endothelial cell-derived heparan sulfate binds basic fibroblast growth factor and protects it from proteolytic degradation. J Cell Biol 107:743–751, 1988.

Snow, A. D., and R. Kisilevsky. Temporal-relationship between glycosaminoglycan accumulation and amyloid deposition during experimental amyloidosis. A histochemical study. Lab Invest 53:37–44, 1985.

Snow, A. D., R. Kisilevsky, C. Stephens and T. Anastassiades. Characterization of tissue and plasma glycosaminoglycans during experimental AA amyloidosis and acute inflammation. Lab Invest 56:665–675, 1987.

Snow, A. D., J. Willmer and R. Kisilevsky. A close ultrastructural relationship between sulfated proteoglycans and AA amyloid fibrils. Lab Invest 57:687–698, 1987.

Snow, A. D., H. Mar, D. Nochlin, K. Kimata, M. Sato, S. Suzuki, J. Hassell and T. N. Wight. The presence of heparan sulfate proteoglycans in the neuritic plaques and congophilic angiopathy in Alzheimer's disease. Am J Path 133:456–463, 1988.

Snow, A. D., R. Kisilevsky and T. N. Wight. Immunolocalization of heparan sulfate proteoglycans to AA amyloid deposition sites in spleen and liver during experimental amyloidosis. In: Amyloid and Amyloidosis, edited by I Isobe, New York, Plenum Press, New York, pp. 87–93. 1988.

Snow, A. D., M. G. Kinsella, P. B. Prather, D. Nochlin, M. B. Podlisny, D. J. Selkoe, R. Kisilevsky, and T. N. Wight. A characteristic binding affinity between heparan sulfate proteoglycans and the A4 amyloid protein of Alzheimer's disease. J. Neuropath. Exp. Neurol. 48:352, 1989 (abstract).

Snow, A. D., H. Mar, D. Nochlin, R. T. Sekiguchi, K. Kimata, Y. Koike and T. N. Wight. Early accumulation of heparan sulfate in neurons and in the beta-amyloid protein containing lesions of Alzheimer's disease and Down's syndrome. Am. J. Path. 137:1253–1270, 1990.

Snow, A. D., R. Bramson, H. Mar, T. N. Wight and R. Kisilevsky. A temporal and ultrastructural relationship between heparan sulfate proteoglycans and AA amyloid in experimental amyloidosis. J. Histochem. Cytochem. 39:1321–1330, 1991.

Virchow, R., Zur cellulose-frage. Arch Pathol Anat 8:416, 1854.

---

The embodiments of the invention in which an exclusive property or privilege is claimed are defined as follows:

1. A method for preventing or treating Alzheimer's disease, comprising administering to a subject in need thereof a peptide within an amyloid protein associated with Alzheimer's disease, consisting of the amino acid sequence Val—His—His—Gln—Lys—Leu (SEQ ID NO:3), Cys—Lys—Arg—Gly—Arg—Lys—Gly (SEQ ID NO:5), or Glu—Ala—Lys—His—Arg—Glu—Arg—Met (SEQ ID NO:7).

2. The method according to claim 1, wherein the peptide consists of the amino acid sequence Val—His—His—Gln—Lys—Leu (SEQ ID NO:3).

3. The method according to claim 1, wherein the peptide consists of the amino acid sequence Val—His—His—Gln—Lys—Leu (SEQ ID NO:3) or Cys—Lys—Arg—Gly—Arg—Lys—Gly (SEQ ID NO:5).

4. The method according to claim 1, wherein the peptide consists of the amino acid sequence Cys—Lys—Arg—Gly—Arg—Lys—Gly (SEQ ID NO:5).

5. The method according to claim 1, wherein the peptide consists of the amino acid sequence Glu—Ala—Lys—His—Arg—Glu—Arg—Met (SEQ ID NO:7).

6. A method for preventing or treating a form of amyloidosis, comprising administering to a subject in need thereof a peptide within an amyloid protein consisting of consensus amino acid sequence of X—B—B—X—B—X wherein X represents an uncharged amino acid residue and B represents a basic amino acid residue, wherein the form of amyloidosis is associated with the amyloid protein from which the peptide is derived.

7. The method according to claim 6, wherein the peptide consists of six amino acid residues.

8. The method according to claim 6, wherein the peptide targets Aβ amyloidosis.

9. The method according to claim 6, wherein the peptide targets AA amyloidosis.

10. The method according to claim 6, wherein the peptide targets AL amyloidosis.

11. The method according to claim 6, wherein the peptide targets prealbumin/transthyretin amyloidosis.

12. The method according to claim 6, wherein the peptide targets Beta$_2$-microglobulin amyloidosis.

13. The method according to claim 6, wherein the peptide targets amyloid associated with medullary carcinoma of the thyroid.

14. The method according to claim 6, wherein the peptide targets PrP amyloidosis.

* * * * *